(12) United States Patent
Sale

(10) Patent No.: US 7,085,690 B2
(45) Date of Patent: Aug. 1, 2006

(54) UNSUPERVISED MACHINE LEARNING-BASED MATHEMATICAL MODEL SELECTION

(76) Inventor: Mark Edward Sale, 1013 Dickinson Cir., Raleigh, NC (US) 27614

( * ) Notice: Subject to any disclaimer, the term of this patent is extended or adjusted under 35 U.S.C. 154(b) by 771 days.

(21) Appl. No.: 09/878,686

(22) Filed: Jun. 11, 2001

(65) Prior Publication Data

US 2003/0088320 A1 May 8, 2003

Related U.S. Application Data

(60) Provisional application No. 60/210,672, filed on Jun. 10, 2000.

(51) Int. Cl.
*G06F 7/60* (2006.01)

(52) U.S. Cl. .............................. 703/2; 382/171; 370/342
(58) Field of Classification Search ..................... 703/2, 703/11, 12; 382/171; 422/68.1; 600/1, 310; 716/8; 370/342; 435/7.5, 288
See application file for complete search history.

(56) References Cited

U.S. PATENT DOCUMENTS

| | | | |
|---|---|---|---|
| 5,465,218 A * | 11/1995 | Handa .............................. | 716/8 |
| 5,857,462 A * | 1/1999 | Thomas et al. .............. | 600/310 |
| 6,031,984 A * | 2/2000 | Walser ........................... | 703/2 |
| 6,128,607 A | 10/2000 | Nordin et al. | |
| 6,197,575 B1 * | 3/2001 | Griffith et al. ............ | 435/288.4 |
| 6,236,894 B1 | 5/2001 | Stoisits et al. | |
| 6,240,399 B1 | 5/2001 | Frank et al. | |
| 6,368,813 B1 * | 4/2002 | Reznik et al. ................ | 435/7.5 |
| 6,432,361 B1 * | 8/2002 | Rothberg et al. .......... | 422/68.1 |
| 6,449,266 B1 * | 9/2002 | Hottinen et al. ............ | 370/342 |
| 6,530,873 B1 * | 3/2003 | Lee ................................ | 600/1 |
| 6,792,399 B1 * | 9/2004 | Phillips et al. ................. | 703/2 |
| 2002/0196975 A1 * | 12/2002 | Cahill ......................... | 382/171 |

OTHER PUBLICATIONS

Hanson KR, Ling R, Havir E., "A computer program for fitting data to the Michaelis Menten equation", Biochemical & Biophysical Research Communications. 29(2):194–7, Oct. 26, 1967.*

Krzyzanski W, Jusko WJ., "Mathematical formalism for the properties of four basic models of indirect pharmacodynamic responses", Journal of Pharmacokinetics & Biopharmaceutics. 25(1):107 23, Feb. 1997.*

"Applied Regression and Analysis", Draper NR, Smith H., John Wiley & Sons, Inc., New York, 1966.*

Guidance for Industry, Population pharmaco kinetics, US Department of Health and Human Services, Food and Drug Administration, Center for Drug Evaluation. Feb. 1999.*

Sheiner, LB, "Analysis of Pharmacokinetic data using parametric models–1: Regression models", J of Pharmacokinetics and Biopharmaceutics. 198912 (1), 93 118.*

(Continued)

Primary Examiner—Samuel Broda
Assistant Examiner—Kandasamy Thangavelu
(74) Attorney, Agent, or Firm—Elaine Sale

(57) ABSTRACT

The invention provides an automated method for identifying an optimal or near optimal mathematical model to describe observed data including: a) the definition of a candidate model search space, b) methods for searching said candidate model search space to identify the optimal or near optimal model within said candidate model search space. The present invention includes algorithms for writing the computer code needed to implement and evaluate candidate models in the software package NONMEM.

17 Claims, 122 Drawing Sheets

OTHER PUBLICATIONS

Mandema JW, Verotta D, Sheiner LB, "Building population pharmacokinetic pharmacodynantic models I. Models for covariate effects", Journal ofPhannacokinetics & Biopharmaceutics. 20(5):511 28, Oct. 1992.*

Mandema JW, Verotta D, Sheiner LB, "Building population pharmacokinetic pharmacodynamic models. Advanced topics in Pharmacokinetic Pharmacodynamic modeling", 1995, Biomedical Simulation Resource. Editor D D'Argenio.*

Akaike A, "Posterior probability for choosing a regression model", Annals of the Institute of Mathematical Statistics. 30: A9 14.*

Maitre PO. Buhrer M. Thomson D. Stanski DR. "A three step approach combining Bayesian regression and NONMEM population analysis: application to midazolam", Journal of Pharmacokinetics & Biopharmaceutics. 19(4):377–84, Aug. 1991.*

Jonsson EN, Karlsson MO, "Automated covariate model building within NONMEM", Pharmaceutical Research. 15(9) 1463–8 Sep. 1998.*

Wade JR, Beal SL, Sambol NC, Interaction between Structural, statistical and covariate models in population pharmacokinetic analysis. J Pharmacokinetics and Biopharmaceutics. 1994 vol. 22, (2), 165–177.*

"Genetic algorithms in optimization and machine learning". David Goldberg, Addison Wesley Publishing Company Inc. 1989.*

Glover, F. (1997). "A Template for Scatter Search and Path Relinking," in Lecture Notes in ComputerSdencre, 1363, J.K. Hao, E. Lutton, E. :Ronald, M. Schoenauer, D. Snyers (Eds.), pp. 13–54.*

Glover, F. and M. Laguna (1997). Tabu Searlh, Kluwer Academic Publishers.*

Glover, F. (1977). "Heuristics for Integer Programming Using Surrogate Constraints," Decision Sciences, vol. 8 No. 1, 156–166.*

Modern Heuristic Techniques for Combinatorial Problems, Glover, F. and M. Laguna (ed. Blackwell, Oxford, 70 150; 1993.*

Tabu search. C.R. Reeves, Metropolis N, Rosenbluth A, Rosenbluth M, Teller A, Teller E. 1953 Journal of Chemical Physics. vol. 21, pp. 1087–1092.*

En Jonsson, Automated Covariate Model Building Within NONMEM, Pharm Res, 1998 15(9) p. 1463–1469 Plenum Publishing.

* cited by examiner

Loop over the values in each dimension to examine all possible combinations of values. If there are two values (0,1) in each of three dimensions, there will be 8 possible combinations

| Dimension 1 | Dimension 2 | Dimension 3 |
|---|---|---|
| 0 | 0 | 0 |
| 0 | 0 | 1 |
| 0 | 1 | 0 |
| 0 | 1 | 1 |
| 1 | 0 | 0 |
| 1 | 0 | 1 |
| 1 | 1 | 0 |
| 1 | 1 | 1 |

File ga_omega.vbp

```
Type=Exe
Form=frm_main.frm
Reference=*\G{00020430-0000-0000-C000-
000000000046}#2.0#0#..\WINDOWS\SYSTEM\StdOle2.tlb#OLE Automation
Module=nmga; nm_gal.bas
Class=token_group; token_group.cls
Form=frm_tokens.frm
Form=frm_new_group.frm
Form=frm_edit_token.frm
Form=frm_options.frm
Object={B02F3647-766B-11CE-AF28-C3A2FBE76A13}#2.5#0; SS32X25.OCX
Object={02B5E320-7292-11CF-93D5-0020AF99504A}#1.0#0; MSCHART.OCX
Object={BDC217C8-ED16-11CD-956C-0000C04E4C0A}#1.1#0; TABCTL32.OCX
Object={6B7E6392-850A-101B-AFC0-4210102A8DA7}#1.2#0; COMCTL32.OCX
Form=frm_text.frm
Reference=*\G{0D452EE1-E08F-101A-852E-
02608C4D0BB4}#2.0#0#..\WINDOWS\SYSTEM\FM20.DLL#Microsoft Forms 2.0
Object Library
Form=frm_graphics.frm
Object={827E9F53-96A4-11CF-823E-000021570103}#1.0#0; GRAPHS32.OCX
Form=frm_histo.frm
Form=frm_sort_results.frm
Form=frm_debug.frm
Object={F9043C88-F6F2-101A-A3C9-08002B2F49FB}#1.1#0; Comdlg32.ocx
Object={D5EEA3C0-6216-11CF-BE62-0080C72EDD2D}#1.0#0; MARQUEE.OCX
IconForm="frm_main"
Startup="Sub Main"
HelpFile=""
ExeName32="NM_GA.exe"
Command32=" "
Name="nm_ga"
HelpContextID="0"
CompatibleMode="0"
MajorVer=1
MinorVer=0
RevisionVer=0
AutoIncrementVer=0
ServerSupportFiles=0
VersionCompanyName="MGA Software"
CompilationType=0
OptimizationType=0
FavorPentiumPro(tm)=0
CodeViewDebugInfo=0
NoAliasing=0
BoundsCheck=0
OverflowCheck=0
FlPointCheck=0
FDIVCheck=0
UnroundedFP=0
StartMode=0
Unattended=0
ThreadPerObject=0
```

FIG. 8A-2

```
MaxNumberOfThreads=1
```

FIG. 8A-3

File ga_omega_vbw

```
frm_main      = 7, 101, 900, 674, , 8, 12, 949, 661,
nmga          = -2, 23, 950, 688,
token_group   = 35, 60, 863, 536,
frm_tokens    = 224, 49, 903, 525, C, 55, 125, 945, 601, C
frm_new_group = 176, 176, 710, 652, C, 154, 154, 688, 630, C
frm_edit_token = 132, 132, 683, 608, C, 154, 154, 705, 630,
frm_options   = 183, 165, 734, 641, C, 25, 20, 649, 606,
frm_text      = 132, 132, 761, 608, Z, 91, 10, 836, 651, C
frm_graphics  = 42, 12, 746, 651, C, 36, 11, 824, 689, C
frm_histo     = 0, 0, 757, 476, C, 32, -9, 901, 688, C
frm_sort_results = 22, 22, 722, 591, C, 0, 0, 733, 476, C
frm_debug     = 132, 132, 633, 600, C, 110, 110, 678, 578, C
```

FIG. 8A-4

File nm_ga1.bas

Attribute VB_Name = "nmga"
Option Explicit
Private Declare Function nmv_exe Lib "c:\nmvexe\vc\nmv_exe.dll" _
    (ByRef theta As Single, ByRef lltheta As Single, ultheta As Single, _
    ByRef omega As Single, ByRef sigma As Single, ByRef obj As Single, _
    ByRef success As Single, ByRef setheta As Single, _
    ByRef seomega As Single, ByRef sesigma As Single, _
    ByRef rm As Single) As Long
Declare Sub Sleep Lib "kernel32" (ByVal dwMilliseconds As Long)
Public paused As Boolean
Public n_omega As Integer
Public non_omega_bits As Integer, omega_bits As Integer
Public n_non_omega_genes As Integer, omega_genes As Integer, n_genes As Integer
Public unique_fit() As Double ' use to list fitness by genome in order to check to see if model has already been run
Public n_unique As Integer
Public current_model As Integer
Public n_models As Integer
Public Const n_groups As Integer = 50
Public token_collection(1 To n_groups) As New token_group
Public n_token_groups As Integer
Public mutation_rate As Single
Public last_gen As Integer
Public cross_over_freq As Single
Public frame_shift_prob As Single
Public n_runs As Integer
Public theta_crit As Single
Public omega_crit As Single
Public sigma_crit As Single
Public cov_crit As Single
Public corr_crit As Single
Public pop_size As Integer
Public generation_limit As Integer
Public call_method As String
Public genome() As Boolean ' catenation of structural genome and omega genome
Public home_directory As String
Public home_drive As String
Public gen_directory As String
Public run_number As Integer
Public upper_fitness_limit As Single
Public lower_fitness_limit As Single
Public stop_run As Boolean
Public this_gen As Integer
Public this_run As Integer
Public success_crit As Single
Public save_control As Boolean
Public save_output As Boolean
Public start_files(1 To 4) As String
Public n_files As Integer
Public omega_block As Boolean
Public n_omega_block As Integer ' number of bits of the genome devoted to the omega block description
Public n_omega_sequence As Integer ' number of bits of the genome devoted to the omega sequence
Const max_theta = 52

FIG. 8A-5

```
Public seed_type As String
Public seed_value As Integer
Public save_best As Boolean Sub Main()
Dim this_file As Integer
n_files = GetSetting(appname:="NM_GA", section:="Startup", _
        Key:="N", Default:=0)
For this_file = 1 To n_files
start_files(this_file) = GetSetting(appname:="NM_GA", section:="Startup", _
        Key:="File" & str(this_file), Default:="")
frm_main.files(this_file).Visible = True
frm_main.files(this_file).Caption = start_files(this_file)
Next this_file
 home_directory = "c:\"

frm_main.Show
End Sub

Sub set_options()
With frm_options
.txt_mutation_rate = mutation_rate
.txt_cross_over_freq = cross_over_freq
.txt_frame_shift_prob = frame_shift_prob
.txt_theta_crit = theta_crit
.txt_omega_crit = omega_crit
.txt_sigma_crit = sigma_crit
.txt_cov_crit = cov_crit
.txt_generations = generation_limit
.txt_upper_limit = upper_fitness_limit
.txt_lower_limit = lower_fitness_limit
.txt_corr_crit = corr_crit
.txt_succ_crit = success_crit
If omega_block = False Then
 .chk_non_diag_omega = 0
Else
.chk_non_diag_omega = 1
End If
If save_control = False Then
.chk_save_control = 0
Else
.chk_save_control = 1
End If
If save_best = False Then
.chk_save_best = 0
Else
.chk_save_best = 1
End If
If save_output = False Then
.chk_save_output = 0
Else
.chk_save_output = 1
End If
Select Case seed_type
Case "clock"
```

FIG. 8A-6

```
.opt_rnd_clock = True
.txt_rnd_seed.Enabled = False
Case "user"
.opt_rnd_user = True
.txt_rnd_seed = seed_value
.txt_rnd_seed.Enabled = True
Case "default"
.opt_rnd_default = True
.txt_rnd_seed.Enabled = False
End Select
If call_method = "dll" Then .opt_dll = True
If call_method = "exe" Then .opt_exe = True
.txt_pop_size = pop_size
If n_runs = 1 Then .opt_1run = True
If n_runs = 2 Then .opt_2runs = True
If n_runs = 4 Then .opt_4runs = True
End With
End Sub Sub get_bin(ByVal in_num As Integer, ByRef bin_str() As Boolean)
Dim n_genes As Integer, remainder As Integer, i As Integer, base As Integer
n_genes = UBound(bin_str)
base = 2
For i = 1 To n_genes
remainder = in_num Mod base
If remainder > 0 Then
bin_str(n_genes - i + 1) = True
Else
bin_str(n_genes - i + 1) = False
End If
in_num = in_num - remainder
base = base * 2
Next i End Sub Sub grid_search()
this_gen = 1
this_run = 0
Dim n_pop As Double, this_group As Integer, this_set As Integer
Dim binary() As Boolean, values() As Integer, max_values() As Integer
Dim n_genes As Integer, this_gene As Integer, this_ind As Integer
Dim cur_gene As Integer
n_genes = count_omega_genes() + count_non_omega_genes()
n_pop = get_n_pop()
If n_pop < 1000000 Then
  Dim n_str As String
    If MsgBox("There will be " & n_pop & " runs" & vbCrLf & _
      "Do you want to continue?", vbOKCancel, "Full grid search") <> vbOK Then
      Exit Sub
    End If
Else
If n_pop > 1000000000 Then
n_str = Format(n_pop, "Scientific")
```

FIG. 8A-7

```
Else
  n_str = Format(n_pop, "0,000,000,000")
End If
  MsgBox ("There are " & n_str & " runs, cannot dimension genome this large, please use GA")
  Exit Sub
End If
' otherwise, continue
ReDim values(1 To n_genes, 1 To n_pop)
ReDim binary(1 To n_genes)
ReDim max_values(1 To n_genes)
ReDim fitness(1 To n_pop)

For this_gene = 1 To n_genes
  max_values(this_gene) = token_collection(this_gene).n_token_sets
Next this_gene
' first set up the first indiivdual, all 1's
For this_gene = 1 To n_genes
  values(this_gene, 1) = 1
Next this_gene
' next creat the population
' then increment each succesive individual, if you exceed max_values, increment the next
For this_ind = 2 To n_pop
  For this_gene = 1 To n_genes
    values(this_gene, this_ind) = values(this_gene, this_ind - 1)
  Next this_gene
  values(n_genes, this_ind) = values(n_genes, this_ind) + 1
  ' check to see if this is over max
  cur_gene = n_genes
  While values(cur_gene, this_ind) > max_values(cur_gene)
    values(cur_gene, this_ind) = 1
    values(cur_gene - 1, this_ind) = values(cur_gene - 1, this_ind) + 1
    cur_gene = cur_gene - 1
  Wend
Next this_ind
gen_directory = home_directory & "\1"
Dim test As String
test = Dir(gen_directory, vbDirectory)
If test <> "1" Then
  MkDir (gen_directory)
End If
  ChDir (home_directory & "\1")
' scaled fitness is dummy
Dim scaled_fitness() As Single
ReDim scaled_fitness(1 To n_pop)
' and run population
run_population scaled_fitness(), values(), False
End Sub Sub ga_runner(start_new_run As Boolean, check_out As Boolean)
Dim scaled_fitness() As Single
Dim n_pop As Double, this_group As Integer, this_set As Integer
Dim genes() As Integer, max_values() As Integer
Dim unmapped_values() As Integer, total_bits As Long
Dim n_bits() As Integer ' number of bits in each gene
Dim total_bit As Integer, this_bit As Integer
Dim n_omega_genes As Integer, this_gene As Integer, this_ind As Integer
```

FIG. 8A-8

```
Dim cur_gene As Integer
Dim n_rows As Integer, max_x As Single
' set random seed if needed
If seed_type = "clock" Then Randomize
If seed_type = "user" Then Randomize (seed_value)

' need to add genes for non-diagonal omega
n_non_omega_genes = count_non_omega_genes()
n_omega_genes = count_omega_genes()
n_genes = n_non_omega_genes + n_omega_genes
' n_pop is either the maximum number or the number selected
' we need to distiguish between genes (on genes) and bits (on genome).
' a gene is represented by one or more bits
' n_pop is the population size, first we'll see ho
n_pop = get_n_pop()
If n_pop > pop_size Then
  n_pop = pop_size
Else
  MsgBox ("Only " & n_pop & " combinations exist, will do grid search")
  grid_search
  Exit Sub
End If
' unmapped values are the "raw" values straight from the genome
' which is basically randomly generated
' you unmap them to get the "genes", which is used to create the control file.
ReDim unmapped_values(1 To n_genes, 1 To n_pop)
ReDim genes(1 To n_genes, 1 To n_pop)
ReDim n_bits(1 To n_genes) ' how many bits in each gene , only 1 if there are 2 possibilities, 2 if 3 or 4 etc
ReDim fitness(1 To n_pop)
ReDim scaled_fitness(1 To n_pop)
ReDim max_values(1 To n_genes)
ReDim fitness(1 To n_pop)
ReDim unique_fit(1 To n_pop * generation_limit, 1 To 7)
' genome_integer, fitness,generation,indivdual, obj, success, covar,
'   need success and covar to put into the table. Scaled fitness will be added later,
'   from a new calculation.
' find the maximum values that the gene can have, min value = 1?
non_omega_bits = count_non_omega_bits
omega_bits = count_omega_bits
total_bits = non_omega_bits + omega_bits
For this_gene = 1 To n_non_omega_genes ' do not include omega genes
    max_values(this_gene) = token_collection(this_gene).n_token_sets
    n_bits(this_gene) = get_nbits(max_values(this_gene))
Next this_gene
' next genes are block genes for omega, each is only 1 bit
For this_gene = n_non_omega_genes + 1 To n_non_omega_genes + n_omega - 1
    max_values(this_gene) = 2
    n_bits(this_gene) = 1
Next this_gene
' final genes are sequence genes for omega
Dim this_omega As Integer: this_omega = n_omega
For this_gene = n_non_omega_genes + n_omega To n_genes ' do not include omega genes
    max_values(this_gene) = this_omega
    this_omega = this_omega - 1
    n_bits(this_gene) = get_nbits(max_values(this_gene))
Next this_gene
```

FIG. 8A-9

```
' now that we know how many bits, we can define the size of the genome (a binary)
'if genomoe is not yet defined
frm_main.pgb_gen.max = generation_limit
  frm_main.pgb_gen.min = 0
If start_new_run = True Then
  ReDim genome(1 To total_bits, 1 To n_pop)
  ' next creat the population
  ' then increment each succesive individual, if you exceed max_values, increment the next
  For this_ind = 1 To n_pop
    For this_bit = 1 To total_bits
      genome(this_bit, this_ind) = (Rnd() > 0.5)
    Next this_bit
  Next this_ind
  frm_main.pgb_gen.value = 0
Else 'continue old run, first check to see if old genome is the right size
  this_gen = last_gen
  If UBound(genome, 1) <> total_bits Or UBound(genome, 2) <> n_pop Then
  MsgBox "Error in genome, starting new GA run"
    ReDim genome(1 To total_bits, 1 To n_pop)
    ' create the population anyway, can't use old genome
    ' then increment each succesive individual, if you exceed max_values, increment the next
    For this_ind = 1 To n_pop
      For this_bit = 1 To total_bits
        genome(this_bit, this_ind) = (Rnd() > 0.5)
      Next this_bit
    Next this_ind
    frm_main.pgb_gen.value = this_gen
End If End If
ReDim min_fitness(1 To generation_limit)
ReDim mean_fitness(1 To generation_limit)
ReDim max_fitness(1 To generation_limit)
n_rows = generation_limit
max_x = generation_limit
If start_new_run = True Then initialize_plot n_rows
While this_gen < generation_limit And stop_run = False
    this_gen = this_gen + 1
    frm_main.pgb_gen.value = this_gen
    Dim ok As String
    gen_directory = home_directory & "\" & this_gen
    ok = Dir(gen_directory, vbDirectory)
    If Trim(ok) = Trim(str(this_gen)) Then
      ok = Dir(gen_directory & "\control", vbNormal)
      If ok <> "" Then Kill gen_directory & "\*.*"
    Else
      MkDir gen_directory
      ChDir gen_directory
    End If
  ' uncode genome, write to unmapped values
  uncode unmapped_values(), n_bits()
  ' then unmap
  unmap genes(), max_values(), unmapped_values(), n_bits()
    run_population scaled_fitness, genes, check_out
    last_gen = this_gen
'   Dim test_str As String, i As Integer
```

FIG. 8A-10

```
' test_str = "before: "
' For i = 1 To UBound(genome, 1)
'   If genome(i, 1) = True Then
'     test_str = test_str & 1
'   Else
'     test_str = test_str & 0
'   End If
' Next i
  get_next_gen scaled_fitness 'only need genome, then goes back to uncode and unmap
' test_str = test_str & vbCrLf & "after: "
' For i = 1 To UBound(genome, 1)
'   If genome(i, 1) = True Then
'     test_str = test_str & 1
'   Else
'     test_str = test_str & 0
'   End If
' Next i
' MsgBox test_str, , "after"
  save_model "temp" & this_run & ".mdl" 'save a temp copy after every new genome defined
Wend
' frm_main.Show 1, frm_main End Sub
Private Sub get_next_gen(scaled_fitness)
Dim n_genes As Integer, this_ind As Integer, i As Integer
Dim cum_fitness() As Single 'cummulative fitness, sum = 1
Dim pairs() As Integer
Dim n_pop As Integer
n_genes = UBound(genome, 1)
n_pop = UBound(scaled_fitness)
ReDim cum_fitness(1 To n_pop)
Dim new_genome() As Boolean
ReDim new_genome(1 To n_genes, 1 To n_pop)
ReDim pairs(1 To 2, 1 To n_pop / 2)

If save_best = True Then
Dim saved_genome() As Boolean: ReDim saved_genome(1 To n_genes)
Dim max_fitness As Single, best_one As Integer
max_fitness = -9999999
For i = 1 To n_pop
  If scaled_fitness(i) > max_fitness Then
    max_fitness = scaled_fitness(i)
    best_one = i
  End If
Next i
For i = 1 To n_genes
  saved_genome(i) = genome(i, best_one)
Next i
End If
'calculate cumulative fitness, scaled to 1.
cum_fitness(1) = scaled_fitness(1)
For i = 2 To n_pop
cum_fitness(i) = cum_fitness(i - 1) + scaled_fitness(i)
Next i
'and divide all by the sum
For i = 1 To n_pop
```

FIG. 8A-11

```
cum_fitness(i) = cum_fitness(i) / cum_fitness(n_pop)
Next i select_pairs pairs, cum_fitness
' cross them over
cross_over_genes pairs
' and mutate
mutate_genes
frame_shift_genes
' and if we're saving the best
If save_best = True Then
  For i = 1 To n_genes
    genome(i, n_pop) = saved_genome(i)
  Next i
End If
End Sub
Private Sub frame_shift_genes()
' select which genes to frame shift
' for these randomly select two points,
' in the first place
Dim this_gene As Integer, this_ind As Integer
Dim start As Integer, last As Integer
Dim rand As Single For this_ind = 1 To UBound(genome, 2)
    rand = Rnd()
    If rand < frame_shift_prob Then
      start = Rnd() * UBound(genome, 1) + 1
      last = Rnd() * UBound(genome, 1) + 1
      If last > start Then
        If last >= UBound(genome, 1) Then last = UBound(genome, 1) - 1
        If start <= 1 Then start = 1
          For this_gene = start To last - 1
            genome(this_gene + 1, this_ind) = genome(this_gene, this_ind)
          Next this_gene
          genome(last, this_ind) = genome(start, this_ind)
        End If
        If start > last Then
        'last can't be 1 or you try to write to position 0
        If last <= 1 Then last = 2
        If start >= UBound(genome, 1) Then start = UBound(genome, 1)
          For this_gene = start To last Step -1
            genome(this_gene - 1, this_ind) = genome(this_gene, this_ind)
          Next this_gene
          genome(last, this_ind) = genome(start, this_ind)
        End If
      End If ' rand < frame_shift if
  Next this_ind
End Sub Private Sub cross_over_genes(pairs() As Integer)
' create new genome
' there are n_pop/2 pairs. each pair results in 2 individuals in the new_genome
Dim new_genome() As Boolean
Dim this_pair As Integer, n_pairs As Integer, length As Integer
Dim this_gene As Integer '
```

FIG. 8A-12

```
' genome is (gene,sub)
' pairs is (1 to 2,nsub/2)
n_pairs = UBound(pairs, 2)
length = UBound(genome, 1)
ReDim new_genome(length, n_pairs * 2)
Dim where As Integer, rand As Single
For this_pair = 1 To n_pairs
' new individuals are (this_pair-1)*2 +1 and this_pair *2 in new_genome
  If Rnd() < cross_over_freq Then
    where = Rnd() * length
    For this_gene = 1 To where
    ' write the left half of the gene, up to where
      new_genome(this_gene, (this_pair - 1) * 2 + 1) = genome(this_gene, pairs(1, this_pair))
      new_genome(this_gene, this_pair * 2) = genome(this_gene, pairs(2, this_pair))
    Next this_gene
    For this_gene = where + 1 To length
      new_genome(this_gene, (this_pair - 1) * 2 + 1) = genome(this_gene, pairs(2, this_pair))
      new_genome(this_gene, this_pair * 2) = genome(this_gene, pairs(1, this_pair))
    Next this_gene
  Else
    ' no cross over
    For this_gene = 1 To length
      new_genome(this_gene, (this_pair - 1) * 2 + 1) = genome(this_gene, pairs(1, this_pair))
      new_genome(this_gene, this_pair * 2) = genome(this_gene, pairs(2, this_pair))
    Next this_gene
  End If
Next this_pair
' then copy new_genome to genome
For this_gene = 1 To length
  For this_pair = 1 To n_pairs * 2
  genome(this_gene, this_pair) = new_genome(this_gene, this_pair)
  Next this_pair
Next this_gene
End Sub Private Sub mutate_genes()
Dim n_genes As Integer, this_gene As Integer
Dim n_pop As Integer, this_ind As Integer
Dim rand As Single
n_genes = UBound(genome, 1): n_pop = UBound(genome, 2)
For this_gene = 1 To n_genes
  For this_ind = 1 To n_pop
  rand = Rnd()
  If rand < mutation_rate Then genome(this_gene, this_ind) = Not (genome(this_gene, this_ind))
  Next this_ind
Next this_gene
End Sub
Function get_nbits(number As Integer) As Integer
If number = 0 Then
get_nbits = 0
Else
get_nbits = Log(number) / Log(2) + 0.4999
End If
End Function
Sub run_population(scaled_fitness() As Single, values() As Integer, check_out As Boolean)
Dim limit_str As String ' is theta at the upper or lower limit
```

FIG. 8A-13

```
Dim genome_integer As Double, old_fitness As Single
Dim old_gen As Integer, old_ind As Integer, old_dir As String
Dim already_run As Boolean
Dim fitness() As Single
Dim n_ind As Integer, control_code As String, i As Integer, ok As String
Dim n_genes As Integer, one_run_values() As Integer
Dim obj As Single, success As Integer, covar As Integer
n_ind = UBound(values, 2)
ReDim fitness(n_ind)
ReDim new_fitness(n_ind)
n_genes = UBound(values, 1)
ReDim one_run_values(1 To n_genes)
Dim this_run1 As Integer
this_run = 0
frm_main.pgb_ind.max = n_ind
'*****************************************************
'*************** TOP OF POPULATION LOOP ***************
'*****************************************************
For this_run1 = 1 To n_ind    ' this_run1 = local this_run
frm_main.pgb_ind.value = this_run1
frm_main.Refresh
DoEvents
Do While paused = True
 DoEvents
 Sleep 500
Loop
this_run = this_run + 1
frm_main.spr_result.col = 9
frm_main.spr_result.row = (this_gen - 1) * n_ind + this_run1
frm_main.spr_result.value = this_run1
frm_main.spr_result.col = 8
frm_main.spr_result.value = this_gen
DoEvents
If stop_run = True Then Exit Sub
 For i = 1 To n_genes
  one_run_values(i) = values(i, this_run1)
 Next i
 control_code = make_control(frm_main.txt_code, one_run_values(), token_collection())
 ok = Dir(gen_directory & "\" & this_run1, vbDirectory)
 If Trim(ok) = Trim(str(this_run1)) Then
  ok = Dir(gen_directory & "\" & this_run1 & "\control", vbDirectory)
  If ok <> "" Then Kill gen_directory & "\" & this_run1 & "\*.*"
 Else
  MkDir gen_directory & "\" & this_run1
  ChDir gen_directory & "\" & this_run1
 End If
 Open gen_directory & "\" & this_run1 & "\control" For Output As #1
 Print #1, control_code
 Close #1
 ' first check to see if this genome has been run
 already_run = False
 limit_str = ""    ' reset the string that describes whether theta is at the boundry to null
 genome_integer = make_int(this_run1)
 For i = 1 To n_unique
  If genome_integer = unique_fit(i, 1) Then
   fitness(this_run1) = unique_fit(i, 2)
```

FIG. 8A-14

```
    old_gen = unique_fit(i, 3)
    old_ind = unique_fit(i, 4)
    obj = unique_fit(i, 5)
    success = unique_fit(i, 6)
    covar = unique_fit(i, 7)
    run_number = run_number + 1
    already_run = True
    ' need to recalcuate limit_str for already run model NOT DONE YET
    Exit For
  End If Next i
Sleep 100 ' to clear file buffer before deleteing files.
If already_run = False Then
  fitness(this_runI) = call_nm("c:", gen_directory & "\" & this_runI, "control", obj, success, covar, limit_str, check_out)
On Error Resume Next 'don't ned to worry if you can't delete file
If Dir("fdata", vbNormal) <> "" Then Kill ("fdata")
If Dir("link.lnk", vbNormal) <> "" Then Kill ("link.lnk")
If Dir("prderr", vbNormal) <> "" Then Kill ("prderr")
If Dir("freport", vbNormal) <> "" Then Kill ("freport")
If Dir("fsubs", vbNormal) <> "" Then Kill ("fsubs")
If Dir("fsubs.for", vbNormal) <> "" Then Kill ("fsubs.for")
If Dir("nonmem.exe", vbNormal) <> "" Then Kill ("nonmem.exe")
If Dir("df.txt", vbNormal) <> "" Then Kill ("df.txt")
On Error GoTo 0
n_unique = n_unique + 1
frm_main.lbl_count = n_unique
unique_fit(n_unique, 1) = genome_integer: unique_fit(n_unique, 2) = fitness(this_runI)
unique_fit(n_unique, 3) = this_gen: unique_fit(n_unique, 4) = this_runI
unique_fit(n_unique, 5) = obj: unique_fit(n_unique, 6) = success
unique_fit(n_unique, 7) = covar
' need to write the results to the spreadsheet, usually done by call_nm
Else
  old_dir = home_directory & "\" & Trim(str(old_gen)) & "\" & Trim(str(old_ind)) & "\"
  ChDir (gen_directory & "\" & this_runI)
  If LCase(Dir(old_dir & "control")) = "control" Then
    FileCopy old_dir & "control", CurDir & "\control"
  End If
  If LCase(Dir(old_dir & "result")) = "result" Then
    FileCopy old_dir & "result", CurDir & "\result"
  End If
  If LCase(Dir(old_dir & "output")) = "output" Then
    FileCopy old_dir & "result", CurDir & "\output"
  End If
  If LCase(Dir(old_dir & "inputs")) = "inputs" Then
    FileCopy old_dir & "inputs", CurDir & "\inputs"
  End If
  If LCase(Dir(old_dir & "parms")) = "parms" Then
    FileCopy old_dir & "parms", CurDir & "\parms"
  End If
End If
' and write the results
With frm_main.spr_result
  .col = 2
  If success = 0 Then
```

FIG. 8A-15

```
            .text = "Yes"
         Else
            .text = "No"
         End If
         .row = run_number
         .col = 3
         If success = 0 And covar = 0 Then
            .text = "Yes"
         Else
            .text = "No"
         End If
         .col = 4
         .text = fitness(this_run1)
         .col = 1
         If obj < 999999999.9 Then
            .text = obj
         Else
            .text = "Crash"
            .col = 2
            .text = "No"
            .col = 3
            .text = "No"
            .col = 4
            .text = "Crash"
         End If
         .col = 11
         .text = limit_str
         .col = 1
         .Action = 0
      End With
      DoEvents: frm_main.Refresh
      If save_control = False Then Kill "control"
      If save_output = False Then
         If Dir(".\output", vbNormal) = "result" Then Kill "result"
      End If
      If stop_run = True Then Exit Sub
   Next this_run1
   scale_fitness scaled_fitness(), fitness()
   ' update plot
   update_plot fitness(), scaled_fitness()
End Sub
Sub update_plot(fitness() As Single, scaled_fitness() As Single)
   ' first append new fitness values onto all_fitness
   ' need to check to see if n generations is exceeded for time limited
   Dim i As Integer, n As Integer
   Dim this_min As Single, this_max As Single, this_mean As Single
   Dim sum As Single, count As Integer
   this_min = 999999999
   this_max = -99999999
   sum = 0
   count = 0
   For i = 1 To UBound(fitness)
      If fitness(i) < 9999999 Then
         If fitness(i) < this_min Then this_min = fitness(i)
         If fitness(i) > this_max Then this_max = fitness(i)
         sum = sum + fitness(i)
```

FIG. 8A-16

```
    count = count + 1
  End If
Next i
If count <> 0 Then
this_mean = sum / count
Else
this_mean = 1000000
End If
With frm_main.MSChart1
  .row = this_gen
  .Column = 1
  .Data = this_min
  .Column = 2
  .Data = this_mean
  .Column = 3
  .Data = this_max
  .DrawMode = VtChDrawModeDraw
End With With frm_main.spr_result
  .col = 10
  For i = 1 To pop_size
    .row = (this_gen - 1) * pop_size + i
    .text = Format(scaled_fitness(i), "0.000")
  Next i End With
End Sub
Sub initialize_plot(n_rows As Integer)
Dim i As Integer, n As Integer
' final 2 columns define upper limit of axis
With frm_main.MSChart1
  .RowCount = 0
  .ColumnCount = 0
  .RowCount = n_rows
  .ColumnCount = 3
  For i = 1 To n_rows
    .row = i
    .RowLabel = i
  Next i
    .DrawMode = VtChDrawModeDraw
    End With
End Sub
Function get_n_pop() As Double
Dim this_group As Integer, n_sets As Double
n_sets = 1
For this_group = 1 To n_token_groups
n_sets = n_sets * token_collection(this_group).n_token_sets
Next this_group
get_n_pop = n_sets
End Function
Function make_control(ga_code As String, values() As Integer, _
          token_collection() As token_group) As String
' so, search ga_code for each instance of stem(1) to stem(n_token_groups)
' thetas will be "{THETA(a)}" in the $PK, ERROR or pred and "{$THETA(A) =} (0,1,2) for the theta
```

FIG. 8A-17

```
'part. similarly for omega and sigma
'afterward, well need to sort out A, B etc and put the $THETA, $OMEGA and $SIMGA
'element in proper order
'and mover the {$THETA(A)= } TO AFTER THE VALUES
Dim done As Boolean, this_int As Integer
If this_run > 15 Then
MsgBox "Pause"
End If
Dim this_token_set As Integer
Dim this_token As Integer
Dim new_code As String, new_string As String, old_string As String
new_code = ga_code
Dim test_string As String
done = False
While Not (done) 'loop here until no more token_stem(*) is found
'this will loop trough the non-omega genes
For this_token_set = 1 To n_token_groups
  For this_token = 1 To token_collection(this_token_set).n_tokens
    old_string = token_collection(this_token_set).stem & "(" & this_token & ")"
    new_string = token_collection(this_token_set).get_token(values(this_token_set), this_token)
    new_code = sub_string(new_code, old_string, new_string)
'    frm_text.txt_text = new_code
'    frm_text.Show 1, frm_main
  Next this_token
Next this_token_set
'check to see if we are done
'loop over token_set stem to look for more tokens
'look for token_set.stem & (1-9)
done = True
For this_token_set = 1 To n_token_groups
  For this_int = 1 To max_theta
    test_string = token_collection(this_token_set).stem & "(" & Trim(str(this_int)) & ")"
'   if test_string is in code, then not done
   frm_text.txt_text = new_code
'   frm_text.Show 1, frm_main
   If InStr(1, new_code, test_string, vbTextCompare) <> 0 Then
     done = False
     Exit For
   End If
  Next this_int
  If done = False Then Exit For
Next this_token_set
Wend 'end of loop over
'now the final editting, replace the {crlf} with real crlf
  new_code = add_crlf(new_code)
If MsgBox(new_code, vbOKCancel, "before match_reference") = vbCancel Then End
  'match up the THETA(A) with correct THETA(1)'s
  new_code = match_references(new_code)
  'sort the resulting theta, etas, sigmas
  new_code = sorter(new_code)
'finally, swap $THETA= to end of line
  new_code = swapper(new_code)
If MsgBox(new_code, vbOKCancel, "final") = vbCancel Then End
'now, if omega_block is true, first remove the all omega parts and substitute the omega BLOCK(n) parts
If omega_block = True Then
'sustitute the BLOCK syngtax
```

FIG. 8A-18

```
frm_text.txt_text = new_code
frm_text.Show 1, frm_main
  new_code = sub_omega_block(new_code, values)
End If
make_control = new_code
MsgBox new_code
End Function
Function sub_omega_block(code As String, values() As Integer) As String
Dim block_part As String, n_etas As Integer
Dim omega_start As Integer, n As Integer
Dim omega_end As Integer, this_gene As Integer
Dim start_pos As Integer, end_pos As Integer
Dim init_omega() As Single: ReDim init_omega(1 To n_omega)
Dim sequences() As Integer: ReDim sequences(1 To n_omega - 1) 'sequence of omegas, all possible etas
(ie max omega, n_omega)
Dim new_sequences() As Integer 'the sequences specefic for this control
                'sequence will have max_omega values
Dim left_part_code As String, right_part_code As String 'left and right parts of code, without the omega
block
Dim covar_values() As Boolean: ReDim covar_values(1 To n_omega - 1) 'is this row in a block with the
row above? does not include first row
  'read in covar_values() go ahead an read in all , even though we'll only use some
For this_gene = 1 To n_omega - 1
  If values(this_gene + n_non_omega_genes) = 2 Then
    covar_values(this_gene) = True
  End If
Next this_gene
  ' while we're here, read in sequences
For this_gene = 1 To n_omega - 1
  sequences(this_gene) = values(this_gene + n_non_omega_genes + n_omega - 1)

' while we're here, read in sequences
Next this_gene
  'we'll need to compress the sequence of the first n sequence values into 1 to n
  'e.g. if we have 4 etas in this control, but max_omega = 7, and sequence is 5,6,3,1,24
  'we compress the first 4 into 3,4,2,1
  'so we need to figure out how many etas in this control file.
n_etas = count_etan(code)
  frm_text.txt_text = code
  frm_text.Show 1, frm_main
  ' first cut out the omega block
omega_start = InStr(1, code, "$OMEGA")
omega_end = InStr(1, code, "$SIGMA") - 1
left_part_code = Left(code, omega_start - 1)
frm_text.txt_text = left_part_code
frm_text.Show 1, frm_main
right_part_code = Right(code, Len(code) - omega_end)
frm_text.txt_text = right_part_code
frm_text.Show 1, frm_main
block_part = Mid(code, omega_start, omega_end - omega_start)
frm_text.txt_text = block_part
frm_text.Show 1, frm_main
  'remove $OMEGA
  block_part = Right(block_part, Len(block_part) - 7) '7 for the $OMEGA
frm_text.txt_text = block_part
frm_text.Show 1, frm_main
```

FIG. 8A-19

```
' remove all parts between ; and vbcrlf
While InStr(1, block_part, ";") <> 0
' If this_run = 4 Then
'   frm_text.txt_text = block_part
'   frm_text.Show 1, frm_main
' End If
  start_pos = InStr(1, block_part, ";") - 1
  ' find end of line
  end_pos = InStr(start_pos, block_part, vbCrLf)
  If end_pos = 0 Then end_pos = Len(block_part)
  'MsgBox Left(block_part, start_pos)
  block_part = Left(block_part, start_pos) & Right(block_part, Len(block_part) - end_pos)
  'MsgBox block_part
Wend
block_part = Trim(block_part)
' now get the values for omega' just read the (??) values
' find pairs between ( and ) and read into init_omega
start_pos = 1: n = 1
While InStr(start_pos, block_part, "(") <> 0
  start_pos = InStr(start_pos, block_part, "(") + 1
  end_pos = InStr(start_pos, block_part, ")")
  init_omega(n) = Val(Mid(block_part, start_pos, end_pos - start_pos))
  n = n + 1
Wend
' and resequence them
' if there are no etas exit, will cause a crash in nonmem, but that's ok
If n_etas > 0 Then
ReDim new_sequences(1 To n_etas)
Else
sub_omega_block = code
Exit Function
End If
' read in the new sequences from the sequenes
' loop over sequences, looking for values 1 to n_etas.
' note that sequences has n_omega - 1 elements, the final
' posiiton is determined by the others
Dim cur_eta_count As Integer ' count of non-zero elements
Dim n_etas_left As Integer ' how many etas are left to fill
Dim i As Integer, cur_eta_position ' current position in new_sequences being examined (to see if = 0)
n_etas_left = n_etas
For i = 1 To n_etas ' looking for ETA(i) in main code
' get the values from sequences
  cur_eta_position = sequences(i)
  If cur_eta_position > n_etas_left Then cur_eta_position = n_etas_left
  cur_eta_count = 0
  For n = 1 To n_etas
    If new_sequences(n) = 0 Then cur_eta_count = cur_eta_count + 1
    If cur_eta_count = cur_eta_position Then
      new_sequences(n) = i
      n_etas_left = n_etas_left - 1
      Exit For
    End If
  Next n
Next i
' substitute the etas
' first change THETA to XXXXX
```

FIG. 8A-20

```
' frm_text.txt_text = code
' frm_text.Show 1, frm_main
left_part_code = sub_string(left_part_code, "THETA", "XXXXX")
Dim new_string As String, old_string As String ' new string will be "YYY(" to prevent re- replacement
For i = 1 To n_etas
  old_string = "ETA(" & Trim(str(i)) & ")"
  new_string = "YYY(" & Trim(new_sequences(i)) & ")"
  left_part_code = sub_string(left_part_code, old_string, new_string)
Next i
' and replace the "YYY(" with "ETA("
left_part_code = sub_string(left_part_code, "YYY(", "ETA(")
left_part_code = sub_string(left_part_code, "XXXXX", "THETA")
'frm_text.txt_text = left_part_code
' frm_text.Show 1, frm_main
' and write the new block
' build new omega block
Dim new_omega_block As String, this_column As Integer
Dim this_row As Integer, cur_end_row As Integer
Dim cur_row_count ' how many rows in this block
Dim off_diag As String
  this_column = 1: this_row = 1
cur_end_row = 1
While cur_end_row <= n_etas
  ' is this a new block, if so how big?
  ' loop through covar_values until you find a false
  cur_row_count = 1
  '***************************************
  '************Part to put into old project
  '***************************************
  Do While covar_values(cur_end_row) And cur_end_row < n_etas
    cur_row_count = cur_row_count + 1
    cur_end_row = cur_end_row + 1
    If cur_end_row > n_etas Then Exit Do
  Loop
  ' need to see if we have exceeded the number of etas
  If cur_end_row > n_etas Then cur_end_row = n_etas
  If cur_row_count = 1 Then
    new_omega_block = new_omega_block & "$OMEGA " & vbCrLf
  Else
    new_omega_block = new_omega_block & "$OMEGA BLOCK(" & Trim(str(cur_row_count)) & ")" & vbCrLf
  End If
  For i = 1 To cur_row_count
    ' construct off diagonal elements
    off_diag = " "
    For n = 1 To i - 1
      off_diag = off_diag & " (0.00001) "
    Next n
    new_omega_block = new_omega_block & off_diag & "(" & init_omega(1) & ")" & vbCrLf
  Next i
  ' MsgBox new_omega_block
  cur_end_row = cur_end_row + 1
Wend ' this_row
sub_omega_block = left_part_code & new_omega_block & right_part_code 'frm_text.txt_text = left_part_code & vbCrLf & new_omega_block & vbCrLf & right_part_code
```

FIG. 8A-21

```
frm_text.Show 1, frm_main
  End Function

' and sequence the etas
  Function sequence_omegas(code As String)
  sequence_omegas = code
  End Function
Function sorter(ByVal code As String) As String
' this function sorts the theta,omegas and sigma initial estimates
Dim new_code As String, cut_out As String, this_prefix As Integer
Dim stack(1 To max_theta) As String, stack_order(1 To max_theta) As Integer
Dim new_cut_out As String, token As String
Dim first_position As Long, last_position As Long, next_position As Long
Dim cur_prefix As String, position As Long
Dim prefixes(1 To 3) As String, stack_position As Integer
prefixes(1) = "{$THETA(": prefixes(2) = "{$ETA(": prefixes(3) = "{$EPS("
If MsgBox(code, vbOKCancel, "in sorter") = vbCancel Then End
Dim old_cut_out As String ' need to preservie original cut out to use in sub_string
new_code = code
For this_prefix = 1 To 3
If MsgBox(code, vbOKCancel) = vbCancel Then End
If InStr(new_code, prefixes(this_prefix)) = 0 Then Exit For
MsgBox new_code
'collect all {THETA(?)=} (XXX)}
' find the first {THETA
first_position = InStr(1, new_code, prefixes(this_prefix))
last_position = first_position
' then find end of theta section
next_position = InStr(last_position + 1, new_code, prefixes(this_prefix))
While next_position <> 0
  next_position = InStr(last_position + 1, new_code, prefixes(this_prefix))
  If next_position <> 0 Then last_position = next_position
Wend
' then find the end of the last theta string
' note that you must end with a ")"
' find the first "}" at the end of the string
last_position = InStr(last_position, new_code, "}")
' then the final ")"
last_position = InStr(last_position - 1, new_code, ")") + 1
' cut out that section and sort it
MsgBox new_code
cut_out = Mid(new_code, first_position, last_position - first_position)
old_cut_out = cut_out 'need to save old cut_out for substring, since we are about
' to change cut_out.
' remove all vbcrlf from cut_out
cut_out = sub_string(cut_out, vbCrLf, "")
MsgBox cut_out
'assemble the stack of values
' find the lowest value, put it in stack(1) etc,
Dim i As Integer, cur_start As String, n As Integer, token1 As String, token2 As String, token3 As String
For i = 1 To max_theta
  cur_start = prefixes(this_prefix) & i & ")=}"
  first_position = InStr(1, cut_out, cur_start)
    ' seperate each token (from $theta to before next $theta) and put then on a stack to be sorted.
  If first_position <> 0 Then
    stack_position = stack_position + 1 ' next stack position
```

FIG. 8A-22

```
' find the start of the next token, or the end of cut_out string
last_position = InStr(first_position + 5, cut_out, "{$") - 1  '
If last_position < 0 Then last_position = Len(cut_out)
token = Mid(cut_out, first_position, last_position - first_position + 1)
' token1 = Mid(cut_out, first_position + Len(cur_start), _
' last_position - first_position - Len(cur_start))
' token2 = " ;" & Mid(cut_out, first_position, Len(cur_start))
stack(stack_position) = token
stack_order(stack_position) = i
End If
Next i
' put cut out back together
new_cut_out = ""
For i = 1 To stack_position
 new_cut_out = new_cut_out & stack(i) & vbCrLf & " "
Next i
 new_code = sub_string(new_code, old_cut_out, new_cut_out)
 new_cut_out = ""
'MsgBox Mid(new_code, 500, Len(new_code) - 500)
 stack_position = 0
Next this_prefix
sorter = new_code
End Function Private Function swapper(code As String) As String
' this function puts the {$THETA(?)} after the value
Dim this_prefix As Integer, position As Integer, eol As Integer, stop_pos As Integer
Dim cut_out As String, rest_str As String, new_str As String, first_part As String
Dim prefixes(1 To 3) As String: prefixes(1) = "{$THETA(": prefixes(2) = "{$ETA(": prefixes(3) =
"{$EPS(":
For this_prefix = 1 To 3
' loop over the text looking for prefix
position = InStr(1, code, prefixes(this_prefix))
While position <> 0
' now find end of line
stop_pos = InStr(position, code, "}")
eol = InStr(stop_pos, code, vbCr) - 1
cut_out = Mid(code, position, eol - position + 1) '+ 1)
stop_pos = InStr(position, code, "}")
rest_str = Trim(Mid(code, stop_pos + 1, eol - stop_pos))
first_part = Trim(Mid(code, position, stop_pos - position))
Mid(first_part, 1, 2) = ";;"
new_str = rest_str & first_part
code = sub_string(code, cut_out, new_str)
position = eol - 3
position = InStr(1, code, prefixes(this_prefix))
Wend
Next this_prefix
swapper = code
End Function
Function match_references(ByVal code As String)
' match up {THETA(A) with {THETA(A) =}(xxxx) to figure out which theta (eta) this is
' and ETA(A) with {ETA(A) =} XX
' and also sigma
Dim this_prefix As Integer, integer_used As Boolean
Dim position As Long, cur_prefix As String, next_value As Integer
```

FIG. 8A-23

```
Dim cur_letter As Integer, cur_integer As Integer, cur_string As String
Dim cur_new_string As String, cur_old_string As String
Dim vtheta_used As Boolean
' first pass through the data to find out which theta, eta and eps is available
' Do theta first note that ETA is substring of THETA
' ETA is in THETA, so we'll first change "THETA" to "XXXXX", do eta then change back
code = sub_string(code, "THETA", "XXXXX")
' MsgBox (code)
Dim prefixes(1 To 3) As String: prefixes(1) = "ETA": prefixes(2) = "THETA": prefixes(3) = "EPS"
For this_prefix = 1 To 3
  cur_prefix = prefixes(this_prefix)
  ' find out if there are any fixed thetas (i.e., theta(1))
frm_text.txt_text = code
frm_text.Show 1, frm_main ' MsgBox (code)
  cur_string = cur_prefix & "(1)"
  position = InStr(code, cur_string)
  cur_integer = 1
  ' find first available theta value
  While position > 0
    cur_integer = cur_integer + 1
    cur_string = cur_prefix & "(" & cur_integer & ")"
    position = InStr(code, cur_string)
  Wend
  ' assign lowest available number
  next_value = cur_integer
  ' MAIN LOOP THROUGH CODE TO SUBSTITUTE THETA(3) FOR THETA(A)
  ' now loop through each posible value to variable theta (theta(a) to theta(z))
  ' NEED MORE LETTER THAN 26
  For cur_letter = Asc("A") To Asc("Z")
    vtheta_used = False
    ' get new theta string
    cur_new_string = cur_prefix & "(" & cur_integer & ")"
    ' get old variable theta string
    cur_old_string = "{" & cur_prefix & "(" & Chr(cur_letter) & ")}"
    position = InStr(1, code, cur_old_string)
    While position > 0
      vtheta_used = True
      code = sub_string(code, cur_old_string, cur_new_string)
      ' MsgBox code
      position = InStr(1, code, cur_old_string)
    Wend
    ' now do {theta(A)=} part
    ' right now we'll just replace, will need to sort and put theta(1) part
    ' at the end later.
    cur_new_string = "{$" & cur_prefix & "(" & cur_integer & ")=}"
    cur_old_string = "{$" & cur_prefix & "(" & Chr(cur_letter) & ")=}"
    position = InStr(1, code, cur_old_string)
    While position > 0
      code = sub_string(code, cur_old_string, cur_new_string)
      position = InStr(1, code, cur_old_string)
    Wend
    ' we want to increment cur_integer only if variable theta is used
    If vtheta_used = True Then cur_integer = cur_integer + 1
  Next cur_letter
```

FIG. 8A-24

'NOW THETA(AA) TO THETA(AZ)

```
For cur_letter = Asc("A") To Asc("Z")
vtheta_used = False
  ' get new theta string
  cur_new_string = cur_prefix & "(" & cur_integer & ")"
  ' get old variable theta string, WITH THE "A"
  cur_old_string = "{" & cur_prefix & "(A" & Chr(cur_letter) & ")}"
  position = InStr(1, code, cur_old_string)
  While position > 0
    vtheta_used = True
    code = sub_string(code, cur_old_string, cur_new_string)
    ' MsgBox code
    position = InStr(1, code, cur_old_string)
  Wend
  ' now do {theta(AA)=} part
  ' right now we'll just replace, will need to sort and put theta(1) part
  ' at the end later.
  cur_new_string = "{$" & cur_prefix & "(" & cur_integer & ")=}"
  cur_old_string = "{$" & cur_prefix & "(A" & Chr(cur_letter) & ")=}"
  position = InStr(1, code, cur_old_string)
  While position > 0
    code = sub_string(code, cur_old_string, cur_new_string)
    position = InStr(1, code, cur_old_string)
  Wend
  ' we want to increment cur_integer only if variable theta is used
  If vtheta_used = True Then cur_integer = cur_integer + 1
Next cur_letter ' NEXT PREFIX
' change XXXX back to THETA if we just did theta
If this_prefix = 1 Then code = sub_string(code, "XXXXX", "THETA")
Next this_prefix
If MsgBox(code, vbOKCancel, "end of match_ref") = vbCancel Then End
match_references = code
End Function Function add_crlf(ByVal code As String) As String
' replace the {crlf} with vbcrlf
Dim where As Long
where = InStr(1, code, "{crlf}")
While where > 0
code = sub_string(code, "{crlf}", vbCrLf)
where = InStr(1, code, "{crlf}")
Wend
add_crlf = code
End Function Function sub_string(code As String, old_str As String, new_str As String) As String
' first check to see if code has changed
If InStr(new_str, old_str) > 0 Then
  sub_string = code
Else
' this function replaces all instances of old_str with new_str
  Dim position As Long, new_code As String, left_part As String, right_part As String
```

FIG. 8A-25

```
position = InStr(1, UCase(code), UCase(old_str)) - 1
new_code = code
While position > 0
  left_part = Left(new_code, position)
  right_part = Right(new_code, Len(new_code) - position - Len(old_str))

new_code = left_part & new_str & right_part
  position = InStr(position, new_code, old_str) - 1
Wend
'MsgBox (sub_string)
'MsgBox (new_str)
'MsgBox (old_str)
  sub_string = new_code
End If
'MsgBox (sub_string)
End Function Function count_non_omega_genes()
count_non_omega_genes = n_token_groups
End Function
Function count_omega_genes()
If omega_block = True Then
n_omega = count_max_omega
count_omega_genes = 2 * (n_omega - 1)
' n_omega genes for the sequence (n_omega-1)! and n_omega -1 for the block definition
Else
  count_omega_genes = 0
End If
End Function
Function count_non_omega_bits()
Dim i As Integer
Dim n As Integer
For i = 1 To n_token_groups
' one token set requires no genes, two requres 1, 3 or 4 requires 2, 5 to 8 requires 3
' basically, ceiling(log base 2(n_token_sets)
n = n + CInt(Log(token_collection(i).n_token_sets) / Log(2) + 0.499999)
Next i
count_non_omega_bits = n
End Function
Function count_omega_bits()
Dim i As Integer
Dim n As Integer
If omega_block = True Then
  n = n_omega - 1  ' for the block part, one bit per gene (is this in a block with the row above?)
  ' sequence part (n-1)!
  For i = n_omega To 2 Step -1
    ' eta(1) can be in n_omega possible values, eta(2) can be in n_omega -1 etc,
    ' to eta(n_omega) which is fixed
    n = n + CInt(Log(i) / Log(2) + 0.499999)
  Next i
  count_omega_bits = n
Else
count_omega_bits = 0
End If
End Function
```

FIG. 8A-26

```
Sub randomizer(ByRef genome() As Boolean)
Dim i As Integer, n As Integer
Randomize
For n = 1 To pop_size
  For i = 1 To UBound(genome, 2)
    genome(n, i) = CInt(Rnd())
  Next i
Next n
End Sub Public Sub save_model(file_name As String)
' get file name
' need to save:
' control file
' genome
' token set
' options
'first, control file
n_models = 1
Dim i As Integer, n As Integer, p As Integer
file_name = home_directory & "\" & file_name
Open file_name For Output As #1
Print #1, "Number of models = " & vbCrLf & n_models
For i = 1 To n_models
Print #1, "########## Begining of model # " & i & " ##########"
Print #1, frm_main.txt_code
Print #1, "########## End of model # " & i & " ##########"
Next i
Print #1, "### End of GA code ###"
Print #1, " Last gen", vbCrLf, last_gen
Print #1, "### Start of genome ###"
Dim gen_str As String
If run_number = 0 Then
Print #1, "Genome not defined"
Else
Dim n_bits As Integer
n_bits = count_omega_bits() + count_non_omega_bits()
Print #1, "N bits = ", vbCrLf, UBound(genome, 1)
Print #1, "Pop size = ", vbCrLf, UBound(genome, 2)
' genome is n_bits by pop size
For i = 1 To UBound(genome, 1)
  For n = 1 To UBound(genome, 2)
    gen_str = gen_str & " " & -Int(genome(i, n)) '- because fals = 0, true = -1
  Next n
  Print #1, gen_str
  gen_str = ""
Next i
End If
Print #1, "### End of genome ###"
Print #1, "### Begining of tokens ###"
For i = 1 To n_token_groups
Print #1, "Group stem = ", vbCrLf, token_collection(i).stem
Print #1, "N token sets = ", vbCrLf, token_collection(i).n_token_sets
Print #1, "N tokens = ", vbCrLf, token_collection(i).n_tokens
```

FIG. 8A-27

```
For n = 1 To token_collection(i).n_token_sets
Print #1, "Token set # ", vbCrLf, n
  For p = 1 To token_collection(i).n_tokens
  Print #1, token_collection(i).get_token(n, p)
  Next p
 Next n
Next i Print #1, "### End of tokens ###"
Print #1, "### Begining of options ###"
Print #1, "cross_over_freq", vbCrLf, cross_over_freq
Print #1, "mutation_rate", vbCrLf, mutation_rate
Print #1, "frame shift prob", vbCrLf, frame_shift_prob
Print #1, "n_runs", vbCrLf, n_runs
Print #1, "theta_crit", vbCrLf, theta_crit
Print #1, "omega_crit", vbCrLf, omega_crit
Print #1, "sigma_crit", vbCrLf, sigma_crit
Print #1, "cov_crit", vbCrLf, cov_crit
Print #1, "pop_size", vbCrLf, pop_size
Print #1, "generation_limit", vbCrLf, generation_limit
Print #1, "call_method", vbCrLf, call_method
Print #1, "upper fitness limit", vbCrLf, upper_fitness_limit
Print #1, "lower_fitness_limit", vbCrLf, lower_fitness_limit
Print #1, "correlation criteria", vbCrLf, corr_crit
Print #1, "success_criteria", vbCrLf, success_crit
Print #1, "save control", vbCrLf, save_control
Print #1, "save best", vbCrLf, save_best
Print #1, "save output", vbCrLf, save_output
Print #1, "omega block", vbCrLf, omega_block
Print #1, "seed type", vbCrLf, seed_type
Print #1, "seed value", vbCrLf, seed_value
Print #1, "### End of options ###"
Print #1, "###################"
Close #1
End Sub
Sub get_model(file As String)
Dim textline As String, code As String, n As Integer, n_bits As Integer
Dim n_token_sets As Integer
Dim i As Integer, token_set_num As Integer, token_num As Integer
For i = 1 To n_token_groups
token_collection(i).clear
Next i
n_token_groups = 0
If Dir(file) = "" Then
  MsgBox ("File not found")
  Exit Sub
End If
' 'see if it is on the start_files
' For i = 1 To n_files
' If start_files(i) = file Then
'   For n = i To n_files - 1
'     start_files(i) = start_files(i + 1)
'     frm_main.files(i).Caption = start_files(i)
'   Next n
'   start_files(n_files) = ""
'   frm_main.files(n_files).Visible = False
```

FIG. 8A-28

```
' n_files = n_files - 1
' End If
'
' Next i
'***********************

For i = 1 To n_files
  If start_files(i) = file Then
'remove it
    For n = i To n_files - 1 Step 1
      start_files(n) = start_files(n + 1)
    Next n
  n_files = n_files - 1
    start_files(n_files + 1) = ""
    Exit For
  End If
Next i
If n_files < 4 Then n_files = n_files + 1
For i = n_files To 2 Step -1
start_files(i) = start_files(i - 1)
frm_main.files(i).Caption = start_files(i)
Next i
start_files(1) = file
frm_main.files(1).Caption = start_files(1)
'**************

Open file For Input As #1

Line Input #1, textline 'Number of models =
    Line Input #1, textline ' number of models
    n_models = Val(textline)
    Line Input #1, textline ' number of models code = ""
    For i = 1 To n_models
    Line Input #1, textline ' number of models
    While Left(textline, 24) <> "########### End of model"
      code = code & textline & vbCrLf
      Line Input #1, textline
    Wend
    frm_main.txt_code = code
    Next i
    Line Input #1, textline '### end of ga code ###
    Line Input #1, textline 'last_gen
    Line Input #1, textline
    last_gen = Val(textline)
    Line Input #1, textline '### Start of genome ###
    Line Input #1, textline
    If Trim(textline) <> "Genome not defined" Then
      Line Input #1, textline
```

FIG. 8A-29

```
n_bits = Val(textline)
Line Input #1, textline
Line Input #1, textline
pop_size = Val(textline)
Dim value As Integer
ReDim genome(1 To n_bits, 1 To pop_size)
 For i = 1 To n_bits
  For n = 1 To pop_size
   Input #1, value
   genome(i, n) = Val(value)
  Next n
 Next i
End If Line Input #1, textline '### Begining of tokens ###
While Trim(textline) <> "### Begining of tokens ###"
   Line Input #1, textline
Wend
While Trim(textline) <> "### End of tokens ###"

While Trim(textline) <> "Group stem ="
   Line Input #1, textline
  Wend
  Line Input #1, textline
    n_token_groups = n_token_groups + 1
    token_collection(n_token_groups).stem = Trim(textline) ' i.e., clear
    frm_tokens.lst_token_group.AddItem Trim(textline)
  While Trim(textline) <> "N token sets ="
   Line Input #1, textline
  Wend
  Line Input #1, textline
  n_token_sets = Val(textline)
  While Trim(textline) <> "N tokens ="
   Line Input #1, textline
  Wend
  Line Input #1, textline
  token_collection(n_token_groups).n_tokens = Val(textline)
  While Trim(textline) <> "Token set #"
   'Line Input #1, textline
  Wend
  Line Input #1, textline
  token_set_num = Val(textline)
  For n = 1 To n_token_sets
  While Trim(textline) <> "Token set #"
   Line Input #1, textline
  Wend
  Line Input #1, textline
  token_set_num = Val(textline)
  token_collection(n_token_groups).add_token_set frm_tokens.lst_token_sets
  token_num = 0
   For i = 1 To token_collection(n_token_groups).n_tokens Line Input #1, textline
     token_num = token_num + 1
     token_collection(n_token_groups).set_token token_set_num, token_num, textline
   Next i
```

FIG. 8A-30

```
Next n
token_num = 0
Line Input #1, textline
Wend
frm_tokens.lst_token_group.clear
For i = 1 To n_token_groups
frm_tokens.lst_token_group.AddItem token_collection(i).stem
Next i
Line Input #1, textline ### Begining of options ###
Line Input #1, textline
While Trim(textline) <> "### End of options ###"

code = Trim(textline)
Line Input #1, textline
textline = Trim(textline)
Select Case code
Case "mutation_rate"
    mutation_rate = Val(textline)
Case "cross_over_freq"
    cross_over_freq = Val(textline)
Case "frame shift prob"
    frame_shift_prob = Val(textline)
Case "n_runs"
    n_runs = Val(textline)
Case "theta_crit"
    theta_crit = Val(textline)
Case "omega_crit"
    omega_crit = Val(textline)
Case "sigma_crit"
    sigma_crit = Val(textline)
Case "cov_crit"
    cov_crit = Val(textline)
Case "success_criteria"
    success_crit = Val(textline)
Case "pop_size"
    pop_size = Val(textline)
Case "generation_limit"
    generation_limit = Val(textline)
Case "call_method"
    call_method = Trim(textline)
Case "upper fitness limit"
    upper_fitness_limit = Trim(textline)
Case "lower_fitness_limit"
    lower_fitness_limit = Trim(textline)
Case "correlation criteria"
    corr_crit = Trim(textline)

Case "save control"
    save_control = Trim(textline)
Case "save best"
    save_best = Trim(textline)
Case "save output"
    save_output = Trim(textline)
Case "omega block"
    omega_block = Trim(textline)
Case "seed type"
```

FIG. 8A-31

```
            seed_type = Trim(textline)
          Case "seed value"
            seed_value = Trim(textline)
          End Select
          Line Input #1, textline
        Wend
        Close #1
        ' update options End Sub
      '
      '
      'Sub scale_fitness(fitness() As Single)
      ''scale by emax, with max fitness at 90% of emax and min fitness at 10% of emax
      ''first find min and max
      'Dim max_fit As Single, min_fit As Single, ef50 As Single, sum_fit As Single
      'Dim i As Integer, n As Integer
      'Dim emax As Single, emin As Single
      'emin = 0.2
      'n = UBound(fitness) - LBound(fitness)
      'max_fit = -999999
      'min_fit = 999999
      'For i = LBound(fitness) To UBound(fitness)
      '  If fitness(i) > max_fit Then max_fit = fitness(i)
      '  If fitness(i) < min_fit Then min_fit = fitness(i)
      '  sum_fit = sum_fit + fitness(i)
      'Next i
      'emax = sum_fit * 2 / n
      'ef50 = sum_fit / n
      'emin = sum_fit * 0.2 / n
      '
      'For i = LBound(fitness) To UBound(fitness)
      '  fitness(i) = emax * fitness(i) ^ 2 / (ef50 ^ 2 + fitness(i) ^ 2) + emin
      'Next i
      'MsgBox emax & Chr(9) & ef50 & Chr(9) & emin
      'End Sub Private Sub map_run()
          Dim n_ind As Integer, this_generation As Integer, max_generation As Integer
          Dim max_values() As Integer
          Dim mapped_values() As Integer
          Dim values() As Integer
          Dim binary() As Boolean
          Dim n_genes As Integer
          Dim n_bits() As Integer
          Dim bin_length As Integer
          'n_genes = 5
          'max_generation = 6
          'n_ind = 3
          ReDim max_values(1 To n_genes)
          ReDim values(1 To n_genes, 1 To n_ind)
          ReDim mapped_values(1 To n_genes, 1 To n_ind)
          'max_values(1) = 5
```

FIG. 8A-32

```
'max_values(2) = 2
'max_values(3) = 4
'max_values(4) = 3
'max_values(5) = 9
ReDim binary(1 To 12, 1 To n_ind)
ReDim n_bits(1 To n_genes)
'values(1, 1) = 1: values(1, 2) = 1: values(1, 3) = 5
'values(2, 1) = 2: values(2, 2) = 2: values(2, 3) = 1
'values(3, 1) = 3: values(3, 2) = 3: values(3, 3) = 1
'values(4, 1) = 2: values(4, 2) = 1: values(4, 3) = 3
'values(5, 1) = 7: values(5, 2) = 6: values(5, 3) = 1
'
'n_bits(1) = 3
'n_bits(2) = 1
'n_bits(3) = 2
'n_bits(4) = 2
'n_bits(5) = 4
''generate random
'

Dim new_values() As Integer
Dim fitness() As Single
ReDim fitness(1 To n_ind)
ReDim new_values(1 To n_genes, 1 To n_ind)
Dim p_cross_over As Single, p_mutation As Single
'p_cross_over = 0.8: p_mutation = 0.4
'*********************************'
'' loop over generations here
'*********************************'
For this_generation = 1 To max_generation
    ' uncode mapped_values, n_bits
    ' unmap new_values, max_values, mapped_values, n_bits
    ' ' create control file
    ' ' evaluate fitness
    ' fitness(1) = 0.2
    ' fitness(2) = 0.6
    ' fitness(3) = 1#
    ' ' scale fitness
    ' ' scaler fitness
    ' ' select pairs by fitness and cross over
    ' 'cross_over_genes fitness, binary, p_cross_over
    ' mutate genome, p_mutation
'********************************************
'' end of generation loop
'********************************************
Next this_generation
''map values, max_values, mapped_values, n_bits
''code binary, mapped_values, n_bits
'' next we creat the population
'
'
Dim tstr As String, i As Integer
For i = LBound(new_values) To UBound(new_values)
    tstr = tstr & new_values(i, 3) & Chr(9) & values(i, 3) & vbCrLf
Next i
'MsgBox tstr
'' note that 0000 = 1, 0001 = 2 etc,we start at value = 1
```

FIG. 8A-33

End Sub

```
Sub map(values() As Integer, max_values() As Integer, mapped_values() As Integer, n_bits() As Integer)
' take unmapped values (1 to max_values) to mapped (0 to 2^ ngenes -1)
' values() is 2 dimensional, (n_genes by n_subject)
' max_valus is 1 dimension (n_genes)
' mapped values is 2 dimensional (n_genes by n_subject)
' n_bits() is 1 dimensino, (n_genes)
Dim i As Integer, n As Integer, p As Integer
' n_bits = 1, max_value = 2;repeat = 0
'  1 -> 0 ;2 -> 1
' n_bits = 2, max_value = 3; repeat = 1
'  1 -> 0 ;2 -> 2: 3 -> 3
' n_bits = 2, max_value = 4; repeat = 0
'  1 -> 0 ;2 -> 1: 3 -> 2; 4 -> 3
' n_bits = 3, max_value = 5; repeat = 3
'  1 -> 0 ;2 -> 2: 3 -> 4; 4 -> 6; 5 -> 7
' n_bits = 3, max_value = 6; repeat = 2
'  1 -> 0 ;2 -> 2: 3 -> 4; 4 -> 5; 5->6;6 -> 7
' n_bits = 3, max_value = 7; repeat = 1
'  1 -> 0 ;2 -> 2: 3 -> 3; 4 -> 4; 5 -> 5; 6 -> 6; 7->7
' n_bits = 3, max_value = 8; repeat = 0
'  1 -> 0 ;2 -> 1: 3 -> 2; 4 -> 3; 5 -> 4; 6 -> 5; 7->6; 8->7
' n_bits = 4, max_value = 9; repeat = 7
'  1 -> 0 ;2 -> 2: 3 -> 4; 4 -> 6; 5 -> 8; 6 -> 10; 7->12; 8->14; 9 -> 15
' n_bits = 4, max_value = 10; repeat = 6
'  1 -> 0 ;2 -> 2: 3 -> 4; 4 -> 6; 5 -> 8; 6 -> 10; 7->12; 8->13;9->14; 10 -> 15
' n_bits = 4, max_value = 11;repeat = 5
'  1 -> 0 ;2 -> 2: 3 -> 4; 4 -> 6; 5 -> 8; 6 -> 10; 7->11; 8->12;9->13; 10 -> 14; 11->15
' n_bits = 4, max_value = 12;repeat = 4
'  1 -> 0 ;2 -> 2: 3 -> 4; 4 -> 6; 5 -> 8; 6 -> 9; 7->10; 8->11;9->12; 10 -> 13; 11->14;12->15
' n_bits = 4, max_value = 13;repeat = 3
'  1 -> 0 ;2 -> 2: 3 -> 4; 4 -> 6; 5 -> 7; 6 -> 8; 7->9; 8->10;9->11;10 -> 12;11->13;12->14;13->15
' n_bits = 4, max_value = 14;repeat = 2
'  1 -> 0 ;2 -> 2: 3 -> 4; 4 -> 5; 5 -> 6; 6 -> 7;7->8; 8->9;9->10;10 -> 11;11->12;12->13;13->14;14->15
Dim repeated As Integer, this_pop As Integer
For this_pop = 1 To UBound(values, 2)
For i = LBound(values, 1) To UBound(values, 1)
repeated = 2 ^ n_bits(i) - max_values(i)
' want 2 * values up to repeated, then 1 * value
If values(i, this_pop) <= repeated + 1 Then
' mapped_values(i, this_pop) = (values(i, this_pop) - 1) * 2
Else
' mapped_values(i, this_pop) = (repeated) * 2 + (values(i, this_pop) - repeated - 1)
End If
Next i
Next this_pop
End Sub Sub unmap(values() As Integer, max_values() As Integer, mapped_values() As Integer, n_bits() As Integer)
' take mapped values (0 to 2^ ngenes -1) back to unmapped (1 to max_values)
' values() is 2 dimensional, (n_genes by n_subject)
' max_valus is 1 dimension (n_genes)
' mapped values is 2 dimensional (n_genes by n_subject)
' n_bits() is 1 dimensino, (n_genes)
Dim i As Integer, repeated As Integer, this_ind As Integer
```

FIG. 8A-34

```
For this_ind = 1 To UBound(values, 2)
For i = LBound(values, 1) To UBound(values, 1)
repeated = 2 ^ n_bits(i) - max_values(i)
' have we reached the change over?
If mapped_values(i, this_ind) <= repeated * 2 Then
values(i, this_ind) = mapped_values(i, this_ind) / 2 + 1
Else
values(i, this_ind) = mapped_values(i, this_ind) - repeated + 1
End If
Next i
Next this_ind
End Sub Sub code(binary() As Boolean, values() As Integer, n_bits() As Integer)
Dim i As Integer, n As Integer, cur_val As Integer, this_ind As Integer
Dim start_pos As Integer, end_pos As Integer
Dim bit_val As Integer ' value of current bit position
start_pos = 1
For this_ind = 1 To UBound(values, 2)

For i = LBound(values, 1) To UBound(values, 1)
end_pos = start_pos + n_bits(i) - 1
  cur_val = values(i, this_ind)
  For n = start_pos To end_pos
    bit_val = 2 ^ (end_pos - n)
    If cur_val >= bit_val Then
      binary(n, this_ind) = True
      cur_val = cur_val - bit_val
    End If
  Next n
  start_pos = end_pos + 1
Next i
start_pos = 1
Next this_ind
End Sub Sub uncode(values() As Integer, n_bits() As Integer)
' takes genome and returns the values used for the control file
' need to know how many bits in each gene (token group)
Dim i As Integer, n As Integer, cur_val As Integer, this_ind As Integer
Dim start_pos As Integer, end_pos As Integer
Dim bit_val As Integer ' value of current bit position
For this_ind = 1 To UBound(values, 2)
start_pos = 1
For i = LBound(values, 1) To UBound(values, 1)
end_pos = start_pos + n_bits(i) - 1
  For n = start_pos To end_pos
    bit_val = 2 ^ (end_pos - n)
    If genome(n, this_ind) = True Then
      cur_val = cur_val + bit_val
    End If
  Next n
  values(i, this_ind) = cur_val
  cur_val = 0
  start_pos = end_pos + 1
Next i
```

FIG. 8A-35

```
start_pos = 1
Next this_ind
End Sub

Sub mutate(binary() As Boolean, p_mutation As Single)
Dim this_gene As Integer, this_ind As Integer
For this_gene = 1 To UBound(binary, 1)
  For this_ind = 1 To UBound(binary, 2)
    If Rnd() < p_mutation Then binary(this_gene, this_ind) = Not (binary(this_gene, this_ind))
  Next this_ind
Next this_gene
End Sub Function InStr_not(string1 As String, string2 As String, string3 As String)
Dim position1 As Long, position2 As Long, start As Long
start = 1
'frm_test.Text1 = string1
'frm_test.Show 1
position1 = InStr(start, string1, string2)
position2 = InStr(start, string1, string3)
While position1 > 0
  If position2 <= position1 And position2 + Len(string3) >= position1 + Len(string2) Then
    start = start + position1
  End If
  position1 = InStr(start, string1, string2)
  position2 = InStr(start, string1, string3)
Wend
InStr_not = position1
End Function Function from_to(start As Long, string1 As String, from_string As String, to_string As String) As String
' this function return the string that starts with from_string and ends with to_string,
' starting the search at start
Dim new_string As String
Dim start_pos As Long, end_pos As Long
' find the start
start_pos = InStr(start, string1, from_string)
' then the end position
end_pos = InStr(start_pos, string1, to_string)
new_string = Mid(string1, start_pos, end_pos + Len(to_string))

from_to = new_string
End Function
Public Function call_nm(drivename As String, pathname As String, controlfile As String, _
    obj1 As Single, succ1 As Integer, covar As Integer, limit_str As String, check_out As Boolean) As
Double
Dim fitness As Double
Dim theta(1 To max_theta) As Single, setheta(1 To max_theta) As Single
Dim lltheta(1 To max_theta) As Single, ultheta(1 To max_theta) As Single
Dim omega(1 To 30, 1 To 30) As Single, seomega(1 To 30, 1 To 30) As Single
Dim sigma(1 To 30, 1 To 30) As Single, sesigma(1 To 30, 1 To 30) As Single
Dim obj(1 To 2) As Single, rm(1 To 69, 1 To 69) As Single
Dim i As Integer
Dim success(1 To 2) As Single
success(1) = 999
```

FIG. 8A-36

```
success(2) = 999
Dim a As Long, p As Integer, ntheta As Integer
Dim out_val As Single
ChDrive drivename
ChDir pathname
If controlfile <> "control" Then FileCopy controlfile, "control"
' need to sent check_out to nmv_exe if false then don't execute
a = nmv_exe(theta(1), lltheta(1), ultheta(1), omega(1, 1), sigma(1, 1), obj(1), success(1), setheta(1), _
    seomega(1, 1), sesigma(1, 1), rm(1, 1))
    fitness = calc_fitness(obj(), success(), setheta(), seomega(), sesigma(), rm(), _
        theta_crit, omega_crit, sigma_crit, cov_crit, ntheta)
run_number = run_number + 1
' hit upper of lower limits?

For i = 1 To ntheta
  If theta(i) <> 0 Then 'check for divide by zero
    If Abs(theta(i) - lltheta(i) / theta(i)) < 0.00000001 Or _
        Abs(theta(i) - ultheta(i) / theta(i)) < 0.000000001 Then
      limit_str = limit_str & Trim(i) & ","
    End If
  End If
Next i
obj1 = obj(1): succ1 = success(1): covar = success(2)
call_nm = fitness
  End Function Private Function calc_fitness(obj() As Single, success() As Single, setheta() As Single, _
    seomega() As Single, sesigma() As Single, rm() As Single, _
    theta_crit As Single, omega_crit As Single, sigma_crit As Single, _
    cov_crit As Single, ntheta As Integer) As Single ' return calculated value for fitness, start with obj, subtract theta_crit for each estimated theta etc
  Dim i As Integer, neff As Integer, n As Integer
  Dim nsigma As Integer
  Dim corr_pen As Single ' correlation > 0.95 penalty
  Dim cov_pen As Single
  'count theta, etas and sigmas
  ' read from file inputs, created by cfilex (and thetas) in nmtran
  Dim iline As String
  Dim s_pen As Single
  Dim nomega_sets As Integer, nomega As Integer
  Dim nsigma_sets As Integer
  Dim fixd As Integer, block_num As Integer, nval As Integer
  Dim nthfxd As Integer, nomfxd As Integer, nsgfxd As Integer
  'MsgBox CurDir
  If Dir("INPUTS", vbNormal) <> "" Then
    Open "inputs" For Input As #1
  Else
    calc_fitness = 999999999.99
    obj(1) = 999999999.99
    Exit Function
  End If
  Line Input #1, iline
  'FIRST LINE IS " NTHETA, NOMEGA, NSIGMA, NTHFXD, NOMFXD, NSGFXD"
  Input #1, ntheta, nomega_sets, nsigma_sets, nthfxd, nomfxd, nsgfxd
  Line Input #1, iline
```

FIG. 8A-37

```
'THIRD LIND IS " NOMBLK , OMDIM, OMFIX"
For i = 1 To nomega_sets
Input #1, block_num, nval, fixd
 ' get # of etas in block
  If fixd = 0 Then
    For n = 1 To nval
      nomega = nomega + n
    Next n
  End If ' fixd = 0
Next i Line Input #1, iline
For i = 1 To nsigma_sets
Input #1, block_num, nval, fixd
nsigma = nsigma + nval * (1 - fixd)
Next i
' loop through srm to see if any are larger than 0.95
neff = ntheta + nomega + nsigma
corr_pen = 0
If success(2) = 0 Then ' only do if cov step ran
  For i = 1 To neff
    For n = 1 To i - 1 ' only do lower triangle
      If rm(i, n) > 0.95 Then
        corr_pen = corr_crit
        Exit For
      End If
    Next n
    If corr_pen > 0 Then Exit For
  Next i
End If
' now calculate fitness
If success(2) > 0 Then
cov_pen = cov_crit
Else
cov_pen = 0
End If
If success(1) > 0 Then
s_pen = success_crit
cov_pen = cov_crit
Else
s_pen = 0
End If
calc_fitness = obj(1) + theta_crit * ntheta + omega_crit * nomega _
  + sigma_crit * nsigma + cov_pen + corr_pen + s_pen Close #1
End Function
Private Sub get_files(files)
files(1) = "nonmem.dll"
files(2) = "freport"
files(3) = "nonmem.lib"
files(4) = "nonmem.exp"
files(5) = "FWARN"
files(6) = "PRDERR"
files(7) = "fsubs"
files(8) = "fsubs.obj"
```

FIG. 8A-38

```
files(9) = "link_lnk"

End Sub

Private Sub wait(filename As String)

Dim list As String, flen As Long
list = Dir(CurDir() & "\" & filename, vbNormal)
If list <> "" Then flen = FileLen(filename)
While flen = 0
  DoEvents
  list = Dir(CurDir() & "\" & filename, vbNormal)
  If list <> "" Then flen = FileLen(filename)
Wend
End Sub Sub scale_fitness(new_fitness() As Single, temp_fitness() As Single)
' linearly between mean - 2sd = 0.3 and mean + 2sd = 2
'Note that a higher obj is a lower fitness
' first find the geometric mean fitness and subtact all values from that.
Dim i As Integer, n As Integer
Dim sd As Single, slope As Single, b As Single, mean As Single
i = UBound(temp_fitness)
Dim sumx As Single, sumxx As Single
' get sd
Dim fitness() As Single
Dim min As Single ' need minium to assign value when no obj
Dim max As Single '
max = -9999999
min = 9999999
ReDim fitness(i)
For n = 1 To i
If temp_fitness(n) < min And temp_fitness(n) > -99999999 Then min = temp_fitness(n)
If temp_fitness(n) > max And temp_fitness(n) < 99999999 Then max = temp_fitness(n)
fitness(n) = temp_fitness(n)
Next n
' now go through and assign min - (0.1)*(max -min) to the unsucessful
Dim high As Single
high = max + 0.1 * (max - min)
For n = 1 To i
If fitness(n) > 99999999 Then fitness(n) = high
Next n
For n = 1 To i
sumx = sumx + fitness(n)
Next n
mean = sumx / i
' now replace fitness with mean - fitness
sumx = 0
For n = 1 To i
fitness(n) = mean - fitness(n)
Next n
' now get sd of transformed fitness
For n = 1 To i
sumx = sumx + fitness(n)
sumxx = sumxx + fitness(n) * fitness(n)
Next n
```

FIG. 8A-39

```
mean = sumx / i
If i > 1 Then
sd = Sqr((i * sumxx - (sumx * sumx)) / (i * (i - 1)))
Else
sd = 0
End If
'now draw line from (mean -2d,lower limit) and (mean + 2sd, upper limit)
If sd = 0 Then
 slope = 0
Else
 slope = (upper_fitness_limit - lower_fitness_limit) / (4 * sd)
'y = mx + b
'b = y - mx
b = 1 - slope * mean
End If
For n = 1 To i
new_fitness(n) = b + slope * fitness(n)
If new_fitness(n) < lower_fitness_limit Then new_fitness(n) = lower_fitness_limit
If new_fitness(n) > upper_fitness_limit Then new_fitness(n) = upper_fitness_limit Next n
'Open "c:\ga\fitness" For Output As #1
Dim n_pop As Integer
For n_pop = 1 To i
Write #1, temp_fitness(n_pop); new_fitness(n_pop)
Next n_pop
'Close #1
End Sub Sub select_pairs(pairs() As Integer, cum_fitness() As Single)
' select individuals based on fitness, put then into pairs
Dim rand As Single, i As Integer, p As Integer, n As Integer, n_ind As Integer
'Open "c:\ga\pairs" For Output As #1
n_ind = UBound(cum_fitness) / 2
For i = 1 To 2
 For n = 1 To n_ind
 rand = Rnd()
 p = 1
 While rand > cum_fitness(p)
 p = p + 1
 Wend
 pairs(i, n) = p
 'Print #1, rand; cum_fitness(p); p
 Next n
Next i
'Close #1
End Sub
Sub load_data(sheet As vaSpread, dir_name As String)
frm_graphics.CommonDialog1.filename = dir_name & "\*.dat"
Dim Data() As Single, temp As String, varname As String, tmp_num As Integer
Dim data_row() As Single, mdv_col As Integer, n_col As Integer
Dim row_string As String
Dim this_col As Integer, this_row As Integer
Dim next_position As Integer, last_position As Integer
frm_graphics.CommonDialog1.DialogTitle = "NONMEM graphics"
```

FIG. 8A-40

```
frm_graphics.CommonDialog1.ShowOpen
If InStr(1, frm_graphics.CommonDialog1.filename, "*") <> 0 Then Exit Sub
If Dir(frm_graphics.CommonDialog1.filename, vbDirectory) = "" Then
MsgBox ("File not found")
Exit Sub
End If frm_graphics.lst_x_axis.clear
frm_graphics.lst_y_axis.clear
frm_graphics.lst_sort_col.clear
Open frm_graphics.CommonDialog1.filename For Input As #1
'find start of table
While Left(Trim(temp), 12) <> "TABLE NO. 1"
Line Input #1, temp
Wend
frm_graphics.Show
'read headers
temp = Input(1, #1)
frm_graphics.spr_data.row = 0
' read whole line then search for tokens
Line Input #1, row_string
' at least position 11 has to be character
next_position = InStr(11, row_string, " ")
last_position = 1
' find the mdv column
Do While next_position <> 0
   this_col = this_col + 1
   varname = Mid(row_string, last_position, next_position - last_position)
   ' if varname is not alpha, there are no variable names
   If IsError(Val(varname)) Then
      MsgBox ("No variable names, next time please use the ""One Header"" option")
      Exit Do
   End If
   If Trim(varname) = "MDV" Then mdv_col = this_col
     frm_graphics.spr_data.col = this_col
     frm_graphics.spr_data.value = Trim(varname)
     frm_graphics.lst_x_axis.AddItem Trim(varname)
     frm_graphics.lst_y_axis.AddItem Trim(varname)
     frm_graphics.lst_sort_col.AddItem Trim(varname)
   last_position = next_position + 1
   ' find next space in row
   next_position = InStr(last_position + 11, row_string, " ")
Loop
' then one more
this_col = this_col + 1
If mdv_col = 0 Then
 MsgBox ("No MDV column found, all data will be displayed")
End If
   varname = Mid(row_string, last_position, Len(row_string) - last_position + 1)
   If Trim(varname) = "MDV" Then mdv_col = this_col
     frm_graphics.spr_data.col = this_col
     frm_graphics.spr_data.value = Trim(varname)
     frm_graphics.lst_x_axis.AddItem Trim(varname)
     frm_graphics.lst_y_axis.AddItem Trim(varname)
     frm_graphics.lst_sort_col.AddItem Trim(varname)
   n_col = this_col
```

FIG. 8A-41

```
ReDim data_row(1 To n_col)
'read data'
While EOF(1) = False
Input #1, row_string
For this_col = 1 To n_col
  data_row(this_col) = Val(Mid(row_string, 1 + (this_col - 1) * 12, 12))
Next this_col
If mdv_col <> 0 Then 'can we check if mdv = 1?
  If data_row(mdv_col) = 0 Then
     this_row = this_row + 1
     'use data
     frm_graphics.spr_data.row = this_row
     For this_col = 1 To n_col
        frm_graphics.spr_data.col = this_col
        frm_graphics.spr_data.value = data_row(this_col)
     Next this_col
  End If
Else
  'use it regardless if mdv not present
   this_row = this_row + 1
   frm_graphics.spr_data.row = this_row
   For this_col = 1 To n_col
      frm_graphics.spr_data.col = this_col
      frm_graphics.spr_data.value = data_row(this_col)
   Next this_col
End If
Wend
Close #1
frm_graphics.spr_data.MaxRows = this_row
'frm_graphics_interface.Show
      End Sub Sub scan_tokens()
'look for (), (1-0), unmatched (), unmatched { }, {()}, ({ }), (()}
'only if they occur before a ";" in the token
Dim short_token As String, token As String, i As Integer, ok As Boolean
Dim this_token_group As Integer, this_token_set As Integer, this_token As Integer
Dim pos1 As Integer, pos2 As Integer
ok = True
For this_token_group = 1 To n_token_groups
  For this_token_set = 1 To token_collection(this_token_group).n_token_sets
    For this_token = 1 To token_collection(this_token_group).n_tokens
    token = token_collection(this_token_group).get_token(this_token_set, this_token)
    'first get the part left of ";"
    If InStr(token, ";") = 0 Then
    short_token = token
    Else
    short_token = Left(token, InStr(1, token, ";") - 1)
    End If
    'look for THETA(1-0)x
    For i = 0 To 9
       If InStr(UCase(short_token), "ETA(" & Trim(str(i)) & ")") <> 0 Then
         MsgBox ("Number " & str(i) & " in token = " & token & " stem = " & _
token_collection(this_token_group).stem & _
       " Token set # " & this_token_set & " Token # " & this_token)
       ok = False
```

FIG. 8A-42

```
    End If
    If InStr(UCase(short_token), "EPS(" & Trim(str(i)) & ")") <> 0 Then
      MsgBox ("Number " & str(i) & " in token = " & token & " stem = " &
token_collection(this_token_group).stem & _
      " Token set # " & this_token_set & " Token # " & this_token)
      ok = False
    End If
  Next i
  ' check for unbalance () have to loop through until all ( are found
  ' before next (
  pos1 = 1 ' position of first (
  pos2 = 1 ' position of next (
  While InStr(pos1 + 1, short_token, "(") <> 0
    pos1 = InStr(pos1 + 1, short_token, "(")
    If pos1 > 0 Then
      If InStr(pos1, short_token, ")") = 0 Then
        MsgBox ("Unmatched ( in " & token & " stem = " & token_collection(this_token_group).stem & _
          " Token set # " & this_token_set & " Token # " & this_token)
        ok = False
      End If
    End If
  Wend
  Next this_token
 Next this_token_set
Next this_token_group
If ok = True Then MsgBox "No errors found"
End Sub Public Function make_int(this_ind As Integer) As Double
'need to start with binary (genome) not values
Dim this_digit As Integer, length_genome As Integer, rval As Double
length_genome = UBound(genome, 1)
For this_digit = 1 To length_genome
If genome(this_digit, this_ind) = True Then rval = rval + 2 ^ (this_digit - 1)
Next this_digit
make_int = rval
End Function
Public Sub clear_form(Form As vaSpread)
Dim this_row As Integer, this_col As Integer
With Form
For this_row = 1 To n_runs
.row = this_row
  For this_col = 1 To 8
  .col = this_col
  .text = ""
  Next this_col
Next this_row
End With
End Sub Public Sub get_stats(directory As String, obj As Single, fitness As Single, covar As Boolean, success As Boolean)
' read the files parms and return the statistics, send to calc_fitness
ChDir directory
```

FIG. 8A-43

```
Close #1
If Dir("PARMS", vbNormal) <> "" Then
Open "PARMS" For Input As #1
End If
Close #1
End Sub
Public Function check_token(box As TextBox) As Boolean
check_token = True
Dim temp_str As String
Dim n_parens As Integer
Dim pos As Integer
temp_str = box.text
pos = InStr(1, temp_str, " ")
While pos <> 0
temp_str = Left(temp_str, pos - 1) & _
        Right(temp_str, Len(temp_str) - pos)
pos = InStr(1, temp_str, " ")
Wend
box.text = temp_str
pos = InStr(1, temp_str, "(")
While pos <> 0
n_parens = n_parens + 1
temp_str = Left(temp_str, pos - 1) & _
        Right(temp_str, Len(temp_str) - pos)
pos = InStr(1, temp_str, "(")
Wend
' now subtract one for each ")"
pos = InStr(1, temp_str, ")")
While pos <> 0
n_parens = n_parens - 1
temp_str = Left(temp_str, pos - 1) & _
        Right(temp_str, Len(temp_str) - pos)
pos = InStr(1, temp_str, ")")
Wend
If n_parens > 0 Then
  MsgBox "Too many ""(""s"
  box.SelStart = InStr(1, box.text, "(") - 1
  box.SelLength = 1
  check_token = False
  Exit Function
End If
If n_parens < 0 Then
  MsgBox "Too many "")""s"
  box.SelStart = InStr(1, box.text, ")") - 1
  box.SelLength = 1
  check_token = False
  Exit Function
End If
' and now the { }
temp_str = box.text
pos = InStr(1, temp_str, "{")
While pos <> 0
n_parens = n_parens + 1
temp_str = Left(temp_str, pos - 1) & _
        Right(temp_str, Len(temp_str) - pos)
pos = InStr(1, temp_str, "{")
```

FIG. 8A-44

```
Wend
' now subtract one for each ")"
pos = InStr(1, temp_str, "}")
While pos <> 0
n_parens = n_parens - 1
temp_str = Left(temp_str, pos - 1) & _
    Right(temp_str, Len(temp_str) - pos)
pos = InStr(1, temp_str, "}")
Wend
If n_parens > 0 Then
  MsgBox "Too many ""{""s"
  box.SelStart = InStr(1, box.text, "{") - 1
  box.SelLength = 1
  check_token = False
  Exit Function
End If
If n_parens < 0 Then
  MsgBox "Too many ""}""s"
  box.SelStart = InStr(1, box.text, "}") - 1
  box.SelLength = 1
  check_token = False
  Exit Function
End If
End Function Public Sub load_results(spread As vaSpread, chart As MSChart)
' recurse through the directories, calculate the fitness for each run and write to spread sheet
Dim i As Integer
Dim n_ind As Integer, this_ind As Integer
Dim cur_gen_dir As String, cur_ind_dir As String, this_row As Integer
Dim obj(1 To 2) As Single, success(1 To 2) As Single, covar As Boolean
Dim fitness() As Double, scaled_fitness() As Single, temp_fitness() As Single
Dim n_gen As Integer, max_ind As Integer, max_gen As Integer, max_x As Single
' how many individuals
this_gen = 1: this_ind = 1: max_gen = 0: max_ind = 0
this_row = 0
'cur_gen_dir = home_directory & "\" & Trim(str(this_gen))
'cur_ind_dir = cur_gen_dir & "\" & Trim(str(this_ind))
For this_gen = 1 To last_gen
'While Dir(cur_gen_dir, vbDirectory) = Trim(str(this_gen))
'    If this_gen > max_gen Then max_gen = this_gen
'    While Dir(cur_ind_dir, vbDirectory) = Trim(str(this_ind))
'      If this_ind > max_ind Then max_ind = this_ind
'      this_ind = this_ind + 1
'      cur_ind_dir = cur_gen_dir & "\" & Trim(str(this_ind))
'    Wend ' cur_ind_dir
   this_ind = 1

'cur_gen_dir = home_directory & "\" & Trim(str(this_gen))
Next this_gen
this_gen = last_gen
'Wend ' cur_gen_dir
ReDim fitness(1 To pop_size)
ReDim scaled_fitness(1 To pop_size): ReDim temp_fitness(1 To pop_size)
' initialize plot axis for generations
```

FIG. 8A-45

```
frm_main.spr_result.MaxRows = pop_size * generation_limit
max_x = generation_limit
initialize_plot generation_limit
this_gen = 1: this_ind = 1
For this_gen = 1 To last_gen
 cur_gen_dir = home_directory & "\" & Trim(str(this_gen))
 While Dir(cur_gen_dir, vbDirectory) = Trim(str(this_gen))
 'While Dir(cur_ind_dir, vbDirectory) = Trim(str(this_ind))
  For this_ind = 1 To pop_size
  cur_ind_dir = cur_gen_dir & "\" & Trim(str(this_ind))
  ' we need obj success, covar, fitness, boundary for theta.
  ' the calc scaled fitness
  ' read input, parms
  read_results cur_ind_dir, obj, success, covar, fitness(this_ind)
  this_row = this_row + 1
  With frm_main.spr_result
    .row = this_row
    .col = 1: .text = obj(1)
    .col = 2: If success(1) = 0 Then .text = "Yes" Else .text = "No"
    .col = 3: If success(2) = 0 Then .text = "Yes" Else .text = "No"
    .col = 4: .text = fitness(this_ind)
    .col = 8:   .text = this_gen
    .col = 9:   .text = this_ind
  End With
  temp_fitness(this_ind) = fitness(this_ind)
  ' this_ind = this_ind + 1
  ' cur_ind_dir = cur_gen_dir & "\" & Trim(str(this_ind))
  Next this_ind ' end of individual while scale_fitness scaled_fitness(), temp_fitness()
' update plot
update_plot temp_fitness(), scaled_fitness()
 'this_gen = this_gen + 1
 ' cur_gen_dir = home_directory & "\" & Trim(str(this_gen))
 ' this_ind = 1
 ' cur_ind_dir = cur_gen_dir & "\" & Trim(str(this_ind))
Next this_gen
run_number = last_gen * pop_size
frm_main.pgb_gen = last_gen
frm_main.pgb_gen.max = generation_limit
frm_main.pgb_ind.max = pop_size frm_main.pgb_ind = 1

'Wend ' end of generation while
MsgBox frm_main.spr_result.MaxRows
End Sub

Sub read_results(this_dir As String, ByRef obj() As Single, ByRef success() As Single, covar As Boolean, fitness As Double)
Dim theta(1 To max_theta) As Single, setheta(1 To max_theta) As Single
Dim ntheta As Integer, nomega As Integer, nsigma As Integer, ntheta_fixed As Integer, nomega_fixed As Integer, nsigma_fixed As Integer
Dim lltheta(1 To max_theta) As Single, ultheta(1 To max_theta) As Single
Dim omega(1 To 30, 1 To 30) As Single, seomega(1 To 30, 1 To 30) As Single
```

FIG. 8A-46

```
Dim sigma(1 To 30, 1 To 30) As Single, sesigma(1 To 30, 1 To 30) As Single
Dim rm(1 To 69, 1 To 69) As Single
Dim i As Integer, temp As String, n As Integer success(1) = 999
success(2) = 999
ChDir this_dir
' read from inputs
If Dir("inputs", vbNormal) <> "" Then
Open "inputs" For Input As #1
Line Input #1, temp
Input #1, ntheta, nomega, nsigma, ntheta_fixed, nomega_fixed, nsigma_fixed
Close #1
End If
If Dir("parms", vbNormal) <> "" Then
' need to read in obj, success, covar,setheta, seomega
Open this_dir & "\" & "parms" For Input As #1
temp = Input(4, #1)
Input #1, obj(1)
temp = Input(9, #1)
Input #1, success(1), success(2)
For i = 1 To 6
Line Input #1, temp
Next i
For i = 1 To ntheta
Input #1, lltheta(i), ultheta(i)
Next i
Line Input #1, temp
For i = 1 To ntheta
Input #1, theta(i)
Next i
Line Input #1, temp
For i = 1 To nomega
  For n = 1 To nomega
    Input #1, omega(i, n)
  Next n
temp = Input(2, #1) ' crlf
Next i
Line Input #1, temp
For i = 1 To nsigma
  For n = 1 To nsigma
    Input #1, sigma(i, n)
  Next n
' If Not (EOF(1)) Then Input #1, temp
Next i
' only read se's and rm if successfull If success(2) = 0 Then
' read rm and se here
End If
Close #1 fitness = calc_fitness(obj(), success(), setheta(), seomega(), sesigma(), rm(), _
        theta_crit, omega_crit, sigma_crit, cov_crit, ntheta)

Else
```

FIG. 8A-47

```
Exit Sub
End If
Close 1
End Sub

Function count_max_omega() As Integer
' go to the tokens and find how many unique omegas are there.
' count the number of unique ETA(??) where ?? is A - AZ
Dim used_eta(1 To 52) As Boolean
Dim this_eta As Integer, token_string As String, check_string As String
Dim this_token_group As Integer, this_token_set
Dim n_omega As Integer, n_token_sets As Integer
Dim this_token As Integer, n_tokens As Integer
Dim test_string As String, n_sets As Integer
Dim control_string As String, n_token_omegas ' number of omegas in tokens (ie., "A")
control_string = UCase(frm_main.txt_code)
' well assume there are less than 10 omegas in the control file and less than 27 on the token sets
test_string = "ETA(" & Trim(Chr(49)) & ")"
' change all the THETAs to xxx
control_string = sub_string(control_string, "THETA", "XXXXX")
While InStr(1, control_string, test_string) <> 0 And n_omega < 10
  n_omega = n_omega + 1
  test_string = "ETA(" * Trim(Chr(49 + n_omega)) & ")"
Wend
For this_token_group = 1 To n_token_groups
  n_token_sets = token_collection(this_token_group).n_token_sets
  For this_token_set = 1 To n_token_sets
    ' loop through set to see if it is used
    n_tokens = token_collection(this_token_group).n_tokens
    For this_token = 1 To n_tokens
      token_string = token_string & vbCrLf & token_collection(this_token_group).get_token(this_token_set, this_token)
    Next this_token
  Next this_token_set
Next this_token_group
' get rid of THETA (to XXXX)
token_string = sub_string(token_string, "THETA", "XXXXX")
' frm_text.txt_text = token_string
' frm_text.Show 1, frm_main
  test_string = "{ETA(" & Trim(Chr(65)) & ")}"
While InStr(1, token_string, test_string) <> 0
  n_token_omegas = n_token_omegas + 1
  test_string = "{ETA(" & Trim(Chr(64 + n_token_omegas)) & ")}"
Wend
count_max_omega = n_omega + n_token_omegas
End Function Function count_etan(control As String) As Integer
Dim control_string As String, test_string As String
Dim test_n As Integer
control_string = UCase(control)
' well assume there are less than 10 omegas in the control file and less than 27 on the token sets
test_n = 1
test_string = "ETA(" & Trim(str(test_n)) & ")"
' change all the THETAs to xxx
```

FIG. 8A-48

```
control_string = sub_string(control_string, "THETA", "XXXXX")
While InStr(1, control_string, test_string) <> 0 And n_omega < 10
  test_n = test_n + 1
  test_string = "ETA(" & Trim(str(test_n)) & ")"
Wend
count_etan = test_n - 1
End Function
```

FIG. 8A-49

File token_group.cls

```
VERSION 1.0 CLASS
BEGIN
   MultiUse = -1  'True
END
Attribute VB_Name = "token_group"
Attribute VB_GlobalNameSpace = False
Attribute VB_Creatable = True
Attribute VB_PredeclaredId = False
Attribute VB_Exposed = False
Attribute VB_Ext_KEY = "SavedWithClassBuilder" ,"Yes"
Attribute VB_Ext_KEY = "Top_Level" ,"Yes"
'local variable(s) to hold property value(s)
Private local_stem As String 'local copy
Private local_n_tokens As Integer ' number of tokens in set , e.g.,
theta(next),(0,1,100) = 2 tokens
Private local_n_token_sets As Integer
Private token_sets(1 To 50, 1 To 10) As String
Option Explicit Public Sub remove_token_set(ByVal position As Integer)
Dim row As Integer, col As Integer
For row = position To local_n_token_sets - 1
 For col = 1 To n_tokens
  token_sets(row, col) = token_sets(row + 1, col)
 Next col
Next row
local_n_token_sets = local_n_token_sets - 1
End Sub 'Private all_sets As Collection
Public Sub add_token_set(lst_sets As ListBox)
local_n_token_sets = local_n_token_sets + 1
get_token_set lst_sets
End Sub
Public Property Get stem() As String
    stem = local_stem
End Property
Public Property Let stem(ByVal lstem As String)
    local_stem = lstem
End Property Public Property Get n_tokens() As Integer
    n_tokens = local_n_tokens
End Property
Public Property Get n_token_sets() As Integer
    n_token_sets = local_n_token_sets
End Property
Public Property Let n_tokens(n As Integer)
    local_n_tokens = n
End Property Public Sub get_token_set(this_list As ListBox)
Dim i As Integer, n As Integer
```

FIG. 8A-50

```
Dim tok_str As String
this_list.clear
For i = 1 To local_n_token_sets
tok_str = i & "  "
  For n = 1 To local_n_tokens
  tok_str = tok_str & "(" & token_sets(i, n) & ") "
  Next n
this_list.AddItem tok_str
Next End Sub
Public Sub get_tokens(this_list As ListBox, this_token_set As Integer)
Dim i As Integer
this_list.clear
If this_token_set <> 0 Then
For i = 1 To local_n_tokens
    this_list.AddItem "(" & token_sets(this_token_set, i) & ") "
  Next i
End If
End Sub Public Sub get_tokens_lines(this_list As ListBox, this_token_set As
Integer)
Dim i As Integer
Dim str As String
Dim start As Integer, last As Integer
this_list.clear
For i = 1 To local_n_tokens
  str = token_sets(this_token_set, i)
  While InStr(1, str, "{crlf}") <> 0
  start = InStr(1, str, "{crlf}")
  last = Len(str) - InStr(1, str, "{crlf}") + Len("{crlf}")
     str = Trim(Left(str, start)) & vbCrLf & _
           Trim(Right(str, last)))
  Wend
  this_list.AddItem "(" & str & ") "
Next i
End Sub
Public Function get_token(ByVal set_num As Integer, ByVal token_num As
Integer) As String
get_token = token_sets(set_num, token_num)
End Function
Public Function get_token_with_lines(ByVal set_num As Integer, ByVal
token_num As Integer) As String
Dim str As String
Dim start As Integer, last As Integer
  str = token_sets(set_num, token_num)
  While InStr(1, str, "{crlf}") <> 0
  start = InStr(1, str, "{crlf}") - 1
  last = Len(str) - InStr(1, str, "{crlf}") - Len("{crlf}") + 1
     str = Trim(Left(str, start)) & vbCrLf & _
           Trim(Right(str, last)))
  Wend get_token_with_lines = str
End Function
```

FIG. 8A-51

```
Public Sub set_token(ByVal set_num As Integer, ByVal token_num As
Integer, value As String)
' we need to replace crlf by another character - (crlf)
Dim start As Integer, last As Integer
While InStr(1, value, vbCrLf) <> 0
start = InStr(1, value, vbCrLf) - 1
last = Len(value) - start - 2
value = Trim(Left(value, start)) & "(crlf)" & _
        Trim(Right(value, last))
Wend
token_sets(set_num, token_num) = value End Sub Public Sub clear()
Dim i As Integer, n As Integer
For i = 1 To n_token_sets
   For n = 1 To n_tokens
   token_sets(i, n) = ""
   Next n
Next i
local_n_token_sets = 0
local_n_tokens = 0
local_stem = ""
End Sub
```

FIG. 8A-52

File frm_main.fm

```
VERSION 5.00
Object = "{B02F3647-766B-11CE-AF28-C3A2FBE76A13}#2.5#0"; "SS32X25.OCX"
Object = "{02B5E320-7292-11CF-93D5-0020AF99504A}#1.0#0"; "MSCHART.OCX"
Object = "{BDC217C8-ED16-11CD-956C-0000C04E4C0A}#1.1#0"; "TABCTL32.OCX"
Object = "{6B7E6392-850A-101B-AFC0-4210102A8DA7}#1.2#0"; "COMCTL32.OCX"
Object = "{F9043C88-F6F2-101A-A3C9-08002B2F49FB}#1.1#0"; "Comdlg32.ocx"
Begin VB.Form frm_main
    Caption         =   "NONMEM GA"
    ClientHeight    =   9120
    ClientLeft      =   2310
    ClientTop       =   1815
    ClientWidth     =   12825
    Icon            =   "frm_main.frx":0000
    LinkTopic       =   "Form1"
    ScaleHeight     =   9120
    ScaleWidth      =   12825
    Begin MSComDlg.CommonDialog CommonDialog1
        Left            =   240
        Top             =   6000
        _ExtentX        =   847
        _ExtentY        =   847
        _Version        =   327680
    End
    Begin VB.Frame Frame1
        Height          =   615
        Left            =   7920
        TabIndex        =   9
        Top             =   8400
        Width           =   2055
        Begin VB.OptionButton Opt_resume
            Caption         =   "Resume"
            Enabled         =   0   'False
            Height          =   255
            Left            =   960
            TabIndex        =   11
            Top             =   240
            Value           =   -1  'True
            Width           =   975
        End
        Begin VB.OptionButton opt_pause
            Caption         =   "Pause"
            Height          =   255
            Left            =   120
            TabIndex        =   10
            Top             =   240
            Width           =   1215
        End
    End
    Begin VB.CommandButton but_stop_run
        Caption         =   "Stop Run"
        Height          =   375
        Left            =   6840
        TabIndex        =   3
        Top             =   8520
```

FIG. 8A-53

```
        Width            =    855
End
Begin TabDlg.SSTab SSTab1
        Height           =    8295
        Left             =    360
        TabIndex         =    0
        Top              =    0
        Width            =    12255
        _ExtentX         =    21616
        _ExtentY         =    14631
        _Version         =    393216
        TabOrientation   =    3
        Tab              =    2
        TabHeight        =    520
        BeginProperty Font {0BE35203-8F91-11CE-9DE3-00AA004B3851}
            Name         =    "Arial"
            Size         =    11.25
            Charset      =    0
            Weight       =    400
            Underline    =    0    'False
            Italic       =    0    'False
            Strikethrough =   0    'False
        EndProperty
        TabCaption(0)    =    "Control"
        TabPicture(0)    =    "frm_main.frx":0442
        Tab(0).ControlEnabled=   0    'False
        Tab(0).Control(0)=    "txt_code"
        Tab(0).ControlCount=  1
        TabCaption(1)    =    "Result Plot"
        TabPicture(1)    =    "frm_main.frx":045E
        Tab(1).ControlEnabled=   0    'False
        Tab(1).Control(0)=    "MSChart1"
        Tab(1).ControlCount=  1
        TabCaption(2)    =    "Results table"
        TabPicture(2)    =    "frm_main.frx":047A
        Tab(2).ControlEnabled=   -1   'True
        Tab(2).Control(0)=    "spr_result"
        Tab(2).Control(0).Enabled=    0    'False
        Tab(2).ControlCount=  1
        Begin VB.TextBox txt_code
            Height       =    7815
            Left         =    -74160
            MultiLine    =    -1   'True
            ScrollBars   =    2    'Vertical
            TabIndex     =    7
            Top          =    240
            Width        =    9495
        End
        Begin MSChartLib.MSChart MSChart1
            Height       =    7815
            Left         =    -74880
            OleObjectBlob =   "frm_main.frx":0496
            TabIndex     =    1
            Top          =    120
            Width        =    10815
        End
        Begin FPSpread.vaSpread spr_result
```

FIG. 8A-54

```
        Height          =   7935
        Left            =   240
        TabIndex        =   8
        Top             =   120
        Width           =   11115
        _Version        =   131077
        _ExtentX        =   19606
        _ExtentY        =   13996
        _StockProps     =   64
        BeginProperty Font {0BE35203-8F91-11CE-9DE3-00AA004BB851}
            Name            =   "MS Sans Serif"
            Size            =   8.25
            Charset         =   0
            Weight          =   700
            Underline       =   0   'False
            Italic          =   0   'False
            Strikethrough   =   0   'False
        EndProperty
        MaxCols         =   11
        ScrollBars      =   2
        ScrollBarShowMax=   0   'False
        SpreadDesigner  =   "frm_main.frx":252A
        UserResize      =   2
        VisibleCols     =   500
        VisibleRows     =   500
    End
End
Begin ComctlLib.ProgressBar pgb_ind
    Height          =   210
    Left            =   1440
    TabIndex        =   2
    Top             =   8400
    Width           =   5175
    _ExtentX        =   9128
    _ExtentY        =   370
    _Version        =   327682
    Appearance      =   1
End
Begin ComctlLib.ProgressBar pgb_gen
    Height          =   210
    Left            =   1440
    TabIndex        =   4
    Top             =   8760
    Width           =   5175
    _ExtentX        =   9128
    _ExtentY        =   370
    _Version        =   327682
    Appearance      =   1
End
Begin VB.Label Label3
    Caption         =   "Unique models"
    Height          =   255
    Left            =   10080
    TabIndex        =   13
    Top             =   8640
    Width           =   1335
End
```

FIG. 8A-55

```
Begin VB.Label lbl_count
    BackColor       =   &H80000009&
    BorderStyle     =   1  'Fixed Single
    Caption         =   "0"
    Height          =   375
    Left            =   11640
    TabIndex        =   12
    Top             =   8520
    Width           =   855
End
Begin VB.Label Label1
    Caption         =   "Individuals"
    Height          =   255
    Left            =   360
    TabIndex        =   6
    Top             =   8400
    Width           =   975
End
Begin VB.Label Label2
    Caption         =   "Generations"
    Height          =   255
    Left            =   360
    TabIndex        =   5
    Top             =   8760
    Width           =   1095
End
Begin VB.Menu file
    Caption         =   "File"
    WindowList      =   -1  'True
    Begin VB.Menu new
        Caption         =   "&New"
    End
    Begin VB.Menu open
        Caption         =   "&Open"
    End
    Begin VB.Menu Save
        Caption         =   "&Save"
    End
    Begin VB.Menu Load
        Caption         =   "Load results"
    End
    Begin VB.Menu save_as
        Caption         =   "S&ave As"
    End
    Begin VB.Menu Exit
        Caption         =   "E&xit"
    End
    Begin VB.Menu break
        Caption         =   "-"
    End
    Begin VB.Menu files
        Caption         =   "Files"
        Index           =   1
        Visible         =   0  'False
    End
    Begin VB.Menu files
        Caption         =   "Files"
```

FIG. 8A-56
```
        Index           =   2
        Visible         =   0   'False
     End
     Begin VB.Menu files
        Caption         =   "Files"
        Index           =   3
        Visible         =   0   'False
     End
     Begin VB.Menu files
        Caption         =   "Files"
        Index           =   4
        Visible         =   0   'False
     End
   End
   Begin VB.Menu edit
      Caption        =   "Edit"
      Begin VB.Menu Edit_token_set
         Caption     =   "Edit Token Set"
      End
      Begin VB.Menu sort
         Caption     =   "Sort Results"
      End
      Begin VB.Menu print
         Caption     =   "Print"
      End
      Begin VB.Menu copy
         Caption     =   "Copy"
      End
   End
   Begin VB.Menu Run
      Caption        =   "Run"
      Begin VB.Menu check_out
         Caption     =   "Check Out"
      End
      Begin VB.Menu ga_Run
         Caption     =   "GA Run"
      End
      Begin VB.Menu continue_run
         Caption     =   "Continue GA run"
      End
      Begin VB.Menu full_grid
         Caption     =   "Full Grid Search"
      End
      Begin VB.Menu debug
         Caption     =   "Debug"
      End
   End
   Begin VB.Menu option
      Caption        =   "Options"
      Begin VB.Menu settings
         Caption     =   "Settings"
      End
   End
   Begin VB.Menu help
      Caption        =   "Help"
   End
End
```

FIG. 8A-57

```
Attribute VB_Name = "frm_main"
Attribute VB_GlobalNameSpace = False
Attribute VB_Creatable = False
Attribute VB_PredeclaredId = True
Attribute VB_Exposed = False
Private cur_model_file_name As String
Private file_name As String ' just the file name without the path
Option Explicit
Private Sub but_stop_run_Click()
stop_run = True
End Sub Private Sub copy_Click()
If SSTab1.Tab = 1 Then
MSChart1.EditCopy
MsgBox "result plot chart copied to clipboard"
End If
If SSTab1.Tab = 2 Then
spr_result.col = -1
spr_result.row = -1
spr_result.Action = 22
End If
End Sub
Private Sub debug_Click()
frm_debug.Show 1, Me
End Sub Private Sub files_Click(Index As Integer)

cur_model_file_name = start_files(Index)
get_model cur_model_file_name
Dim pos As Integer
pos = 1
While InStr(pos + 1, cur_model_file_name, "\") > 0
pos = InStr(pos + 1, cur_model_file_name, "\")
Wend
home_directory = Left(cur_model_file_name, pos - 1)
ChDir (home_directory)
file_name = Right(cur_model_file_name, Len(cur_model_file_name) - pos)
home_drive = Left(home_directory, 2)
ChDrive (home_drive)
End Sub Private Sub Form_Unload(Cancel As Integer)
End
End Sub Private Sub Load_Click()

If MsgBox("Load results from " & home_directory & " ?", vbOKCancel) <>
vbOK Then Exit Sub
load_results frm_main.spr_result, frm_main.MSChart1

End Sub
```

FIG. 8A-58

```
Private Sub opt_pause_Click()
opt_pause.Enabled = False
paused = True
Opt_resume.Enabled = True
End Sub
'
Private Sub opt_pause_DblClick()
opt_pause.Enabled = False
paused = True
Opt_resume.Enabled = True
End Sub Private Sub Opt_resume_Click()
Opt_resume.Enabled = False
paused = False
opt_pause.Enabled = True
End Sub
'
Private Sub Opt_resume_DblClick()
Opt_resume.Enabled = False
paused = False
opt_pause.Enabled = True
End Sub Private Sub print_click()
If SSTab1.Tab = 1 Then
End If
If SSTab1.Tab = 2 Then
spr_result.col = -1
spr_result.row = -1
spr_result.Action = 22
End If End Sub
Private Sub New_Click()
Me.txt_code.text = ""
set_default_options
End Sub
Private Sub set_default_options()

End Sub

Private Sub sort_Click()
frm_sort_results.Show
End Sub

Private Sub spr_result_Click(ByVal col As Long, ByVal row As Long)
Dim gen As Integer, ind As Integer
Dim text As String, textline As String
Dim file_name As String
Select Case col
  Case 5
  spr_result.col = 8
  spr_result.row = row
  If spr_result.value = "" Then
  MsgBox "No results available"
```

FIG. 8A-59

```
Exit Sub
End If
If save_output = False Then
MsgBox "Output file not saved, see options"
Exit Sub
End If
gen = spr_result.value
spr_result.col = 9
ind = spr_result.value
If spr_result.value = "" Then
MsgBox "No results available"
Exit Sub
End If
file_name = home_directory & "\" & gen & "\" & ind & "\output"
If Dir(file_name, vbNormal) = "" Then
MsgBox "Output file not found"
Exit Sub
End If Open file_name For Input As #1
Do While Not EOF(1)   ' Loop until end of file.
    Line Input #1, textline  ' Read line into variable.
    text = text & textline & vbCrLf
Loop
frm_text.Caption = "Output file"
frm_text.txt_text = text
Me.Hide
frm_text.Show
Close #1      ' Close file.
 Case 6
 spr_result.col = 8
 spr_result.row = row
 If spr_result.value = "" Then
 MsgBox "No results available"
 Exit Sub
 End If
 If save_control = False Then
 MsgBox "control file not saved, see options"
 Exit Sub
 End If
 gen = spr_result.value
 spr_result.col = 9
 If spr_result.value = "" Then
 MsgBox "No results available"
 Exit Sub
 End If
 ind = spr_result.value
 file_name = home_directory & "\" & gen & "\" & ind & "\control"
 Open file_name For Input As #1
 Do While Not EOF(1)   ' Loop until end of file.
    Line Input #1, textline  ' Read line into variable.
    text = text & textline & vbCrLf
Loop
frm_text.Caption = "Control file"
frm_text.txt_text = text
frm_text.Show 1, frm_main
Close #1      ' Close file.
```

FIG. 8A-60

```
Case 7 spr_result.col = 8
spr_result.row = row
If spr_result.value = "" Then
MsgBox "Generation not available"
Exit Sub
End If
gen = spr_result.value
spr_result.col = 9
ind = spr_result.value
file_name = home_directory & "\" & gen & "\" & ind
load_data frm_graphics.spr_data, file_name frm_graphics.Show
 End Select
End Sub Private Sub check_out_Click()
Dim n_runs As Integer
n_runs = frm_options.txt_pop_size * frm_options.txt_generations
frm_main.spr_result.MaxRows = n_runs
SSTab1.Tab = 2
stop_run = False
frm_main.but_stop_run.Enabled = True
ga_runner True, True
frm_main.but_stop_run.Enabled = False
End Sub Private Sub continue_run_Click()
stop_run = False
ga_runner False, False
End Sub
Private Sub Edit_token_set_Click()
Me.Hide
frm_tokens.Show End Sub
Private Sub exit_Click()

Dim i As Integer
SaveSetting appname:="NM_GA", section:="Startup", _
            Key:="N", setting:=n_files
For i = 1 To n_files
SaveSetting appname:="NM_GA", section:="Startup", _
            Key:="File" & str(i), setting:=start_files(i)
Next i
'SaveSetting appname:="NM_GA", section:="Startup", _
'            Key:="File" & str(1), setting:="c:\570\amy\ga\570b.mdl"
'
'SaveSetting appname:="NM_GA", section:="Startup", _
'            Key:="File" & str(2), setting:="c:\570\amy\ga\570c.mdl"

End
End Sub
Private Sub Form_Load()
```

FIG. 8A-61

```
'ChDir "c:\ga\"
'cur_model_file_name = "c:\ga\gen.mdl"
'get_model cur_model_file_name
'frm_tokens.1st_token_group.ListIndex = 0
'frm_tokens.1st_token_sets.ListIndex = 0

End Sub

Private Sub full_grid_Click()
stop_run = False
grid_search
End Sub
Private Sub ga_Run_Click()
Dim n_runs As Integer
n_runs = frm_options.txt_pop_size * frm_options.txt_generations
frm_main.spr_result.MaxRows = n_runs
SSTab1.Tab = 2
stop_run = False
frm_main.but_stop_run.Enabled = True
ga_runner True, False
frm_main.but_stop_run.Enabled = False
'frm_inter_results.Hide End Sub
Private Sub open_Click()
Me.CommonDialog1.DialogTitle = "Open GA model"
ChDir (home_directory)
Me.CommonDialog1.InitDir = home_directory
Me.CommonDialog1.filename = "*.mdl"
Me.CommonDialog1.ShowOpen
If Me.CommonDialog1.filename = "*.dat" Or Me.CommonDialog1.filename =
"" Or Me.CommonDialog1.filename = "*.mdl" Then
Exit Sub
End If
cur_model_file_name = Me.CommonDialog1.filename
get_model Me.CommonDialog1.filename
frm_tokens.1st_token_group.ListIndex = 0
frm_tokens.1st_token_sets.ListIndex = 0
' get home directory name
Dim pos As Integer
pos = 1
While InStr(pos + 1, cur_model_file_name, "\") > 0
pos = InStr(pos + 1, cur_model_file_name, "\")
Wend
home_directory = Left(cur_model_file_name, pos - 1)
file_name = Right(cur_model_file_name, Len(cur_model_file_name) - pos)
ChDir (home_directory)
home_drive = Left(home_directory, 2)
ChDrive (home_drive)

End Sub

Private Sub save_as_Click()
Dim file_name As String
Me.CommonDialog1.DialogTitle = "Save GA model file"
Me.CommonDialog1.InitDir = home_directory
```

FIG. 8A-62

```
Me.CommonDialog1.Filter = "*.mdl"
Me.CommonDialog1.filename = "*.mdl"
Me.CommonDialog1.ShowSave
file_name = Me.CommonDialog1.filename
If Trim(file_name) = "" Then Exit Sub
If file_name = "" Then
Exit Sub
Else
' set home directory
Dim pos As Integer
pos = 1
While InStr(pos + 1, file_name, "\") > 0
pos = InStr(pos + 1, file_name, "\")
Wend
home_directory = Left(file_name, pos - 1)
ChDir (home_directory)
home_drive = Left(home_directory, 2)
ChDrive (home_drive)
file_name = Right(file_name, Len(file_name) - pos)
ChDrive (home_drive)
cur_model_file_name = file_name
save_model (file_name)
Dim i As Integer, n As Integer
For i = 1 To n_files
   If start_files(i) = home_drive & "\" & home_directory & "\" &
file_name Then
' remove it
      For n = i To n_files - 1 Step 1
         start_files(n) = start_files(n + 1)
      Next n
   n_files = n_files - 1
      start_files(n_files + 1) = ""
      Exit For
   End If
Next i
If n_files < 4 Then n_files = n_files + 1
For i = n_files To 2 Step -1
start_files(i) = start_files(i - 1)
frm_main.files(i).Caption = start_files(i)
Next i
start_files(1) = home_drive & "\" & home_directory & "\" & file_name
frm_main.files(1).Caption = start_files(1)
End If
End Sub Private Sub Save_Click()
save_model (file_name)
End Sub Private Sub settings_Click()
Me.Hide
set_options
frm_options.Show 1, Me
End Sub Private Sub SSTab1_Click(PreviousTab As Integer)
```

FIG. 8A-63

```
If SSTab1.Tab = 2 Then
sort.Enabled = True
Else
sort.Enabled = False
End If
End Sub
```

FIG. 8A-64

File frm_debug.frm

```
VERSION 5.00
Begin VB.Form frm_debug
   Caption         =   "Debug Options"
   ClientHeight    =   4080
   ClientLeft      =   60
   ClientTop       =   345
   ClientWidth     =   5760
   LinkTopic       =   "Form1"
   ScaleHeight     =   4080
   ScaleWidth      =   5760
   StartUpPosition =   3  'Windows Default
   Begin VB.CommandButton but_check_unmatched
      Caption      =   "Check for unmatched tokens"
      Height       =   495
      Left         =   360
      TabIndex     =   5
      Top          =   1200
      Width        =   2535
   End
   Begin VB.Frame Frame1
      Caption      =   "Break"
      Height       =   1215
      Left         =   3240
      TabIndex     =   2
      Top          =   480
      Width        =   1815
      Begin VB.CheckBox chk_debug_control
         Caption   =   "Control files"
         Height    =   255
         Left      =   120
         TabIndex  =   4
         Top       =   720
         Width     =   1575
      End
      Begin VB.CheckBox chk_debug_tokens
         Caption   =   "Tokens"
         Height    =   255
         Left      =   120
         TabIndex  =   3
         Top       =   360
         Width     =   1575
      End
   End
   Begin VB.CommandButton but_scan_numbs
      Caption      =   "Scan for numbers"
      Height       =   495
      Left         =   360
      TabIndex     =   1
      Top          =   360
      Width        =   2535
   End
   Begin VB.CommandButton Command1
      Caption      =   "Done"
      Height       =   495
      Left         =   2280
```

FIG. 8A-65

```
            TabIndex        =   0
            Top             =   3240
            Width           =   975
        End
    End
End
Attribute VB_Name = "frm_debug"
Attribute VB_GlobalNameSpace = False
Attribute VB_Creatable = False
Attribute VB_PredeclaredId = True
Attribute VB_Exposed = False
Option Explicit Private Sub but_scan_numbs_Click()
scan_tokens
End Sub Private Sub Command1_Click()
Me.Hide
End Sub
```

FIG. 8A-66

File frm_edit_token.frm

```
VERSION 5.00
Object = "{F9043C88-F6F2-101A-A3C9-08002B2F49FB}#1.1#0"; "Comdlg32.ocx"
Begin VB.Form frm_edit_token
   Caption         =   "Edit Token"
   ClientHeight    =   5355
   ClientLeft      =   3900
   ClientTop       =   3645
   ClientWidth     =   7065
   LinkTopic       =   "Form1"
   ScaleHeight     =   5355
   ScaleWidth      =   7065
   Begin MSComDlg.CommonDialog CommonDialog1
      Left            =   480
      Top             =   4680
      _ExtentX        =   847
      _ExtentY        =   847
      _Version        =   327680
   End
   Begin VB.TextBox txt_token
      BeginProperty Font
         Name            =   "MS Sans Serif"
         Size            =   12
         Charset         =   0
         Weight          =   400
         Underline       =   0   'False
         Italic          =   0   'False
         Strikethrough   =   0   'False
      EndProperty
      Height          =   3615
      HideSelection   =   0   'False
      Left            =   960
      MultiLine       =   -1  'True
      ScrollBars      =   2   'Vertical
      TabIndex        =   2
      Top             =   480
      Width           =   5655
   End
   Begin VB.CommandButton but_cancel
      Caption         =   "Cancel"
      Height          =   495
      Left            =   4200
      TabIndex        =   1
      Top             =   4320
      Width           =   1095
   End
   Begin VB.CommandButton but_done
      Caption         =   "Done"
      Height          =   495
      Left            =   2040
      TabIndex        =   0
      Top             =   4320
      Width           =   1095
   End
   Begin VB.Label Label1
      Caption         =   "Token"
```

FIG. 8A-67

```
        Height          =   375
        Left            =   120
        TabIndex        =   3
        Top             =   960
        Width           =   855
     End
     Begin VB.Menu file
        Caption         =   "File"
        Begin VB.Menu import
           Caption      =   "Import"
        End
        Begin VB.Menu export
           Caption      =   "Export"
        End
        Begin VB.Menu save
           Caption      =   "Save and close"
        End
        Begin VB.Menu exit
           Caption      =   "Exit (don't save)"
        End
     End
End
Attribute VB_Name = "frm_edit_token"
Attribute VB_GlobalNameSpace = False
Attribute VB_Creatable = False
Attribute VB_PredeclaredId = True
Attribute VB_Exposed = False Private Sub but_done_Click()
If check_token(txt_token) = False Then
Exit Sub
End If
Me.Hide
frm_tokens.Show
End Sub Private Sub import_Click()
Dim code As String, textline As String
Me.CommonDialog1.DialogTitle = "Import token"
Me.CommonDialog1.filename = "*.txt"
Me.CommonDialog1.ShowOpen
If Me.CommonDialog1.filename = "*.txt" Or _
   Me.CommonDialog1.filename = "" Then
   Exit Sub
End If
   Open Me.CommonDialog1.filename For Input As #1
   Do While Not EOF(1)  ' Loop until end of file.
      Line Input #1, textline  ' Read line into variable.
      Debug.Print textline     ' Print to Debug window.
      code = code & textline & vbCrLf
   Loop
Close #1
Me.txt_token = code
End Sub Private Sub export_Click()
```

FIG. 8A-68

```
Dim code As String, textline As String
Dim new_code As String
Me.CommonDialog1.DialogTitle = "Export token"
Me.CommonDialog1.filename = "*.txt"
Me.CommonDialog1.ShowSave
If Me.CommonDialog1.filename = "*.txt" Or _
   Me.CommonDialog1.filename = "" Then
   Exit Sub
End If
   Open Me.CommonDialog1.filename For Output As #1
   code = Me.txt_token
Print #1, code   ' Print text to file.
Close #1
End Sub
```

FIG. 8A-69

File frm_graphics.frm

```
VERSION 5.00
Object = "{B02F3647-766B-11CE-AF28-C3A2FBE76A13}#2.5#0";  "SS32X25.OCX"
Object = "{BDC217C8-ED16-11CD-956C-0000C04E4C0A}#1.1#0";  "TABCTL32.OCX"
Object = "{827E9F53-96A4-11CF-823E-000021570103}#1.0#0";  "GRAPHS32.OCX"
Object = "{F9043C88-F6F2-101A-A3C9-08002B2F49FB}#1.1#0";  "Comdlg32.ocx"
Begin VB.Form frm_graphics
   Caption         =   "Graphics"
   ClientHeight    =   8835
   ClientLeft      =   60
   ClientTop       =   630
   ClientWidth     =   10695
   LinkTopic       =   "Form1"
   ScaleHeight     =   8835
   ScaleWidth      =   10695
   Begin MSComDlg.CommonDialog CommonDialog1
      Left            =   3240
      Top             =   8400
      _ExtentX        =   847
      _ExtentY        =   847
      _Version        =   327680
   End
   Begin TabDlg.SSTab SSTab1
      Height          =   8535
      Left            =   120
      TabIndex        =   0
      Top             =   120
      Width           =   10110
      _ExtentX        =   17833
      _ExtentY        =   15055
      _Version        =   393216
      TabOrientation  =   1
      Tabs            =   1
      TabsPerRow      =   10
      TabHeight       =   520
      TabCaption(0)   =   "Main"
      TabPicture(0)   =   "frm_graphics.frx":0000
      Tab(0).ControlEnabled=   -1  'True
      Tab(0).Control(0)=   "Label2"
      Tab(0).Control(0).Enabled=   0   'False
      Tab(0).Control(1)=   "Label1"
      Tab(0).Control(1).Enabled=   0   'False
      Tab(0).Control(2)=   "spr_data"
      Tab(0).Control(2).Enabled=   0   'False
      Tab(0).Control(3)=   "lst_sort_col"
      Tab(0).Control(3).Enabled=   0   'False
      Tab(0).Control(4)=   "lst_y_axis"
      Tab(0).Control(4).Enabled=   0   'False
      Tab(0).Control(5)=   "lst_x_axis"
      Tab(0).Control(5).Enabled=   0   'False
      Tab(0).Control(6)=   "but_histos"
      Tab(0).Control(6).Enabled=   0   'False
      Tab(0).Control(7)=   "But_done"
      Tab(0).Control(7).Enabled=   0   'False
      Tab(0).Control(8)=   "but_make_plot"
      Tab(0).Control(8).Enabled=   0   'False
```

FIG. 8A-70

```
Tab(0).Control(9)=    "chk_unit_line"
Tab(0).Control(9).Enabled=    0    'False
Tab(0).Control(10)=    "chk_abs_value"
Tab(0).Control(10).Enabled=    0    'False
Tab(0).Control(11)=    "chk_sort_col"
Tab(0).Control(11).Enabled=    0    'False
Tab(0).Control(12)=    "chk_plot_matrix"
Tab(0).Control(12).Enabled=    0    'False
Tab(0).Control(13)=    "chk_ind_y_plots"
Tab(0).Control(13).Enabled=    0    'False
Tab(0).Control(14)=    "chk_ind_sorted_plots"
Tab(0).Control(14).Enabled=    0    'False
Tab(0).Control(15)=    "Graph(0)"
Tab(0).Control(15).Enabled=    0    'False
Tab(0).Control(16)=    "Frame1"
Tab(0).Control(16).Enabled=    0    'False
Tab(0).ControlCount=    17
Begin VB.Frame Frame1
   Height    =    615
   Left    =    360
   TabIndex    =    17
   Top    =    6480
   Width    =    3495
   Begin VB.OptionButton opt_smooth
      Caption    =    "Smooth"
      Enabled    =    0    'False
      Height    =    255
      Left    =    2040
      TabIndex    =    20
      Top    =    240
      Width    =    1095
   End
   Begin VB.OptionButton opt_line
      Caption    =    "Line"
      Enabled    =    0    'False
      Height    =    255
      Left    =    1200
      TabIndex    =    19
      Top    =    240
      Width    =    735
   End
   Begin VB.CheckBox chk_trend_line
      Caption    =    "Trend"
      Height    =    255
      Left    =    120
      TabIndex    =    18
      Top    =    240
      Width    =    855
   End
End
Begin GraphsLib.Graph Graph
   Height    =    255
   Index    =    0
   Left    =    8400
   TabIndex    =    16
   Top    =    6360
   Visible    =    0    'False
```

FIG. 8A-71

```
        Width           =   495
        _Version        =   327680
        _ExtentX        =   873
        _ExtentY        =   450
        _StockProps     =   96
        GraphStyle      =   2
        GraphType       =   9
        LeftTitleStyle  =   1
        RandomData      =   0
        SymbolData      =   "13-13-7-13"
        SymbolSize      =   10
     End
     Begin VB.CheckBox chk_ind_sorted_plots
        Caption         =   "Individual Sorted Plots"
        Height          =   255
        Left            =   7080
        TabIndex        =   15
        Top             =   5870
        Width           =   2175
     End
     Begin VB.CheckBox chk_ind_y_plots
        Caption         =   "Individual Y Plots"
        Height          =   255
        Left            =   3720
        TabIndex        =   14
        Top             =   5870
        Width           =   1815
     End
     Begin VB.CheckBox chk_plot_matrix
        Caption         =   "Plot matrix"
        Height          =   255
        Left            =   3960
        TabIndex        =   13
        Top             =   6720
        Width           =   1095
     End
     Begin VB.CheckBox chk_sort_col
        Caption         =   "Use Sort Item"
        Height          =   255
        Left            =   7080
        TabIndex        =   9
        Top             =   3480
        Width           =   1455
     End
     Begin VB.CheckBox chk_abs_value
        Caption         =   "Use Absolute Value"
        Height          =   255
        Left            =   3720
        TabIndex        =   8
        Top             =   6240
        Width           =   1935
     End
     Begin VB.CheckBox chk_unit_line
        Caption         =   "Unit Line"
        Height          =   255
        Left            =   600
        TabIndex        =   7
```

FIG. 8A-72

```
        Top             =    6240
        Width           =    1215
    End
    Begin VB.CommandButton but_make_plot
        Caption         =    "Make plot"
        Height          =    615
        Left            =    600
        TabIndex        =    6
        Top             =    7320
        Width           =    1575
    End
    Begin VB.CommandButton But_done
        Caption         =    "Done"
        Height          =    615
        Left            =    4080
        TabIndex        =    5
        Top             =    7320
        Width           =    1575
    End
    Begin VB.CommandButton but_histos
        Caption         =    "Make Histos"
        Height          =    615
        Left            =    7320
        TabIndex        =    4
        Top             =    7320
        Width           =    1575
    End
    Begin VB.ListBox lst_x_axis
        Height          =    2010
        Left            =    480
        MultiSelect     =    2    'Extended
        TabIndex        =    3
        Top             =    3720
        Width           =    1935
    End
    Begin VB.ListBox lst_y_axis
        Height          =    2010
        Left            =    3720
        MultiSelect     =    2    'Extended
        TabIndex        =    2
        Top             =    3720
        Width           =    1935
    End
    Begin VB.ListBox lst_sort_col
        Enabled         =    0    'False
        Height          =    2010
        Left            =    7080
        TabIndex        =    1
        Top             =    3720
        Width           =    1935
    End
    Begin FPSpread.vaSpread spr_data
        Height          =    3015
        Left            =    240
        TabIndex        =    10
        Top             =    120
        Width           =    9495
```

FIG. 8A-73

```
        _Version         =   131077
        _ExtentX         =   16748
        _ExtentY         =   5318
        _StockProps      =   64
        BeginProperty Font {0BE35203-8F91-11CE-9DE3-00AA004BB851}
            Name            =   "MS Sans Serif"
            Size            =   8.25
            Charset         =   0
            Weight          =   700
            Underline       =   0   'False
            Italic          =   0   'False
            Strikethrough   =   0   'False
        EndProperty
        SpreadDesigner   =   "frm_graphics.frx":001C
    End
    Begin VB.Label Label1
        Caption          =   "X axis"
        Height           =   255
        Left             =   480
        TabIndex         =   12
        Top              =   3360
        Width            =   1575
    End
    Begin VB.Label Label2
        Caption          =   "Y axis"
        Height           =   255
        Left             =   3720
        TabIndex         =   11
        Top              =   3360
        Width            =   1575
    End
 End
 Begin VB.Menu file
    Caption          =   "File"
    Begin VB.Menu Close
        Caption          =   "Close"
    End
 End
 Begin VB.Menu edit
    Caption          =   "Edit"
    Begin VB.Menu copy
        Caption          =   "&Copy"
        Shortcut         =   ^C
    End
 End
End
Attribute VB_Name = "frm_graphics"
Attribute VB_GlobalNameSpace = False
Attribute VB_Creatable = False
Attribute VB_PredeclaredId = True
Attribute VB_Exposed = False
Option Explicit Private Sub but_done_Click()
Unload frm_graphics
frm_main.Show
End Sub
```

FIG. 8A-74

```
Private Sub but_histos_Click()
Dim i As Integer
With frm_histo.lst_histo
  .clear
For i = 1 To lst_x_axis.ListCount
  .AddItem lst_x_axis.list(i - 1)
Next i
End With
Me.Hide
frm_histo.Show
End Sub Private Sub but_make_plot_Click()
Dim i As Integer, n_tabs As Integer, n_plots As Integer
If lst_x_axis.ListIndex < 0 Then
 MsgBox "Please select one or more x variables"
 Exit Sub
End If
If lst_y_axis.ListIndex < 0 Then
 MsgBox "Please select one or more y variables"
 Exit Sub
End If
If chk_sort_col.value = 1 And lst_sort_col.ListIndex < 0 Then
 MsgBox "Please select a sort variable"
 Exit Sub
End If
' figure out how may x and y selected
Dim n_x As Integer, n_y As Integer, xs(1 To 20) As Integer, ys(1 To 20)
As Integer For i = 0 To lst_x_axis.ListCount - 1
  If lst_x_axis.Selected(i) = True Then
    n_x = n_x + 1
    xs(n_x) = i
  End If
Next i
For i = 0 To lst_y_axis.ListCount - 1
  If lst_y_axis.Selected(i) = True Then
    n_y = n_y + 1
    ys(n_y) = i
  End If
Next i
n_tabs = SSTab1.Tabs
n_plots = Graph.count - 1 ' index starts at 0, but we don't use 0
' single x, single y, single plot
If n_x = 1 And n_y = 1 And chk_plot_matrix.value = 0 And chk_sort_col =
0 Then
   n_tabs = n_tabs + 1
   n_plots = n_plots + 1
   SSTab1.Tabs = n_tabs
   SSTab1.Tab = n_tabs - 1
   SSTab1.TabCaption(n_tabs - 1) = lst_x_axis.list(lst_x_axis.ListIndex)
& "/" & lst_y_axis.list(lst_y_axis.ListIndex)
   Load Graph(n_plots)
   make_xy lst_x_axis.ListIndex + 1, lst_y_axis.ListIndex + 1,
Graph(n_plots)
```

FIG. 8A-75

```
End If
' single x, several
If n_x = 1 And n_y > 1 And chk_plot_matrix.value = 0 And chk_sort_col =
0 Then
' one plot, one x, many y
make_multiy xs(1), ys, n_y
End If
If n_x > 1 And chk_plot_matrix.value = 0 And chk_sort_col = 0 Then
make_multi_x xs, ys, n_x, n_y
End If
' plot matrix, one plot
If chk_plot_matrix.value = 1 And chk_sort_col = 0 Then
  plot_matrix xs, ys, n_x, n_y
End If
' sorted, one x, one y
If chk_sort_col = 1 And n_x = 1 And n_y = 1 Then
make_sorted_xy xs(1), ys(1), Me.lst_sort_col.ListIndex
End If End Sub Private Sub make_sorted_xy(X As Integer, y As Integer, sort_col As
Integer)
' NOTE THAT LISTINDICES START AT 0
Dim n_subs As Integer, max_obs As Integer, this_point As Integer
Dim this_sub As Integer, this_graph_point As Integer, this_tab As
Integer
Dim n_data As Integer, i As Integer, this_plot As Integer, this_id As
Integer
' first need to pass through data, and count max obs per subject
n_subs = 1
spr_data.col = sort_col + 1
spr_data.row = 1
this_sub = spr_data.value
For i = 2 To spr_data.MaxRows
  spr_data.row = i
  If spr_data.value <> this_sub Then
    n_subs = n_subs + 1
    this_sub = spr_data.value
  End If
Next i
' add a tab
SSTab1.Tabs = SSTab1.Tabs + 1
this_tab = SSTab1.Tabs
SSTab1.Tab = this_tab - 1
this_plot = Graph.count - 1
this_plot = this_plot + 1
Load Graph(this_plot)
With Graph(this_plot)
   .Visible = True
   .Enabled = True
   .Top = 400
   .Left = 400
   .width = 9200
   .height = 7400
  ' how many data
  n_data = spr_data.MaxRows
```

FIG. 8A-76

```
   .NumSets = n_subs
   .NumPoints = max_obs
   this_sub = 1
   this_graph_point = 1
While this_point < n_data
  spr_data.row = this_point
  spr_data.col = sort_col
  If spr_data.value <> this_id Then
      this_id = spr_data.value
      this_sub = this_sub + 1
      this_graph_point = 1
  Graph(this_plot).ThisSet = this_sub
  Graph(this_plot).ThisPoint = this_graph_point
  spr_data.col = X
    .XPos(i) = Val(spr_data.text)
   spr_data.col = y
    .Data(i) = Val(spr_data.text)
   End If
Wend ' this point < n_data
' loop over data sets and set options
   .SymbolData = 13 ' solid cirle
   .SymbolSize = 30
  spr_data.col = y
  spr_data.row = 0
   .LeftTitle = spr_data.text
  spr_data.col = X
   .BottomTitle = spr_data.text
   .DrawMode = graphDraw
  End With
End Sub Private Sub make_multi_x(xs() As Integer, ys() As Integer, n_x As
Integer, n_y As Integer)
' unique plot for each x, each plot will have all y's
Dim this_plot As Integer
For this_plot = 1 To n_x
make_multiy xs(this_plot), ys, n_y
Next this_plot
End Sub Private Sub plot_matrix(xs() As Integer, ys() As Integer, n_x As
Integer, n_y As Integer)

Dim n_plots As Integer
Dim i As Integer, n As Integer, this_plot As Integer, p As Integer
Dim n_data As Integer
Dim this_tab As Integer, start_plot As Integer, end_plot As Integer
this_tab = SSTab1.Tabs
start_plot = Graph.count - 1 ' keep to specify this plot we're doing
this_plot = start_plot ' current plot #
Const left_margin = 50
Const top_margin = 50
Const gap = 0
Dim width As Integer, height As Integer
Dim max_dim As Integer ' maximum value of row or cols
max dim = n_x
```

FIG. 8A-77

```
If n_y > n_x Then max_dim = n_y
width = (SSTab1.width - left_margin * 2) / max_dim - (max_dim - 1) *
gap
' 400 FOR TAB ROW
' need to adjust height for # of rows of tabs
height = (SSTab1.height - top_margin * 2 - 400) / max_dim - (max_dim -
1) * gap
n_plots = n_x * n_y + start_plot
 n_data = spr_data.MaxRows
While this_plot < n_plots
 this_tab = this_tab + 1
 SSTab1.Tabs = this_tab
 SSTab1.Tab = this_tab - 1
 SSTab1.TabCaption(this_tab - 1) = "Matrix"
    For i = 1 To n_x
      If this_plot = n_plots Then Exit For
      For n = 1 To n_y
      If this_plot = n_plots Then Exit For
      this_plot = this_plot + 1
       Load Graph(this_plot)
       With Graph(this_plot)
        .Visible = True
        .BorderStyle = 0
         .Left = left_margin + (n - 1) * width
         .width = width
         .Top = top_margin + (i - 1) * height
         .height = height
         .BottomTitle = lst_x_axis.list(xs(i))
         .LeftTitle = lst_y_axis.list(ys(n))
         .Enabled = True
          .NumSets = 1
           .NumPoints = n_data
          For p = 1 To n_data
          Dim junk As String
          spr_data.row = p
'          spr_data.col = 0
'          junk = spr_data.text
'          spr_data.col = 1
'          junk = spr_data.text
          spr_data.col = xs(i) + 1
            .XPos(p) = Val(spr_data.text)
          spr_data.col = ys(n) + 1
            .Data(p) = Val(spr_data.text)
          Next p
            .SymbolData = 13  ' solid cirle
            .SymbolSize = 20 + 18 * max_dim If Me.chk_trend_line.value = 1 Then
     If opt_line.value = True Then .LineStats = 8
     If opt_smooth.value = True Then
      .CurveOrder = 2
      .LineStats = 16
      .PatternedLines = 1
      .PatternData = 1
     End If
    End If
         .DrawMode = graphDraw
```

FIG. 8A-78

```
        End With
      Next n
    Next i
Wend

End Sub
Private Sub make_multiy(X As Integer, ys() As Integer, n_y As Integer)
Dim i As Integer, n As Integer, p As Integer, this_tab
Dim n_data As Integer, this_y As Integer, this_plot As Integer
' add a tab
SSTab1.Tabs = SSTab1.Tabs + 1
this_tab = SSTab1.Tabs
SSTab1.Tab = this_tab - 1
n_data = spr_data.MaxRows
this_plot = Graph.count - 1
this_plot = this_plot + 1
Load Graph(this_plot)
With Graph(this_plot)
        .Visible = True
        .Enabled = True
        .Top = 400
        .Left = 400
        .width = 9200
        .height = 7400
        .NumSets = n_y
        .NumPoints = n_data
For this_y = 1 To n_y
        .ThisSet = this_y
          For p = 1 To n_data
          spr_data.row = p
          spr_data.col = X + 1
          .XPos(p) = Val(spr_data.text)
          spr_data.col = ys(this_y) + 1
          .Data(p) = Val(spr_data.text)
          Next p
        .SymbolData = 13 ' solid cirle
        .SymbolSize = 38
        If Me.chk_trend_line.value = 1 Then
           If opt_line.value = True Then .LineStats = 8
           If opt_smooth.value = True Then
              .CurveOrder = 2
              .LineStats = 16
              .PatternedLines = 1
              .PatternData = 1
           End If
        End If
        spr_data.col = ys(this_y) + 1
        spr_data.row = 0
        Dim divider As String
    .LeftTitle = .LeftTitle & divider & spr_data.text
     divider = "/"
      spr_data.col = X + 1
Next this_y
     spr_data.col = X + 1
        spr_data.row = 0
    .BottomTitle = spr_data.text
         .DrawMode = graphDraw
```

FIG. 8A-79

```
End With

SSTabl.TabCaption(this_tab - 1) = spr_data.text
End Sub
Private Sub make_xy(X As Integer, y As Integer, this_graph As Graph)
Dim n_data As Integer, i As Integer
Dim sumx As Double, sumxx As Double, sumy As Double, sumxy As Double,
sumyy As Double
'Dim maxx As Single, minx As Single
Dim slope As Single, intercept As Single, xval As Single, yval As
Single
'SSTabl.TabCaption(SSTabl.Tabs - 1) = lst_x_axis.list(X) & "/" &
lst_y_axis.list(Y)
With this_graph
   .Visible = True
   .Enabled = True
   .Top = 400
   .Left = 400
   .width = 9200
   .height = 7400
   ' how many data
  n_data = spr_data.MaxRows
   .NumSets = 1
   .NumPoints = n_data
'  maxx = -999999999
'  minx = 999999999
  For i = 1 To n_data
  spr_data.row = i
  spr_data.col = X
   xval = Val(spr_data.text)
   .XPos(i) = xval
   sumx = sumx + xval
   sumxx = sumxx + xval * xval
'  If xval > maxx Then maxx = xval
'  If xval < minx Then minx = xval
   spr_data.col = y
   yval = Val(spr_data.text)
   .Data(i) = yval
   sumy = sumy + yval
   sumyy = sumyy + yval * yval
   sumxy = sumxy + yval * xval
  Next i
   .SymbolData = 13   ' solid cirle
   .SymbolSize = 30
  spr_data.col = y
  spr_data.row = 0
   .LeftTitle = spr_data.text
  spr_data.col = X
   .BottomTitle = spr_data.text
   ' add trend line
  If Me.chk_trend_line.value = 1 Then
   If opt_line.value = True Then .LineStats = 8
   If opt_smooth.value = True Then
    .CurveOrder = 2
    .LineStats = 16
    .PatternedLines = 1
    .PatternData = 1
```

FIG. 8A-80

```
  End If
 End If
 Dim rsquare As Double
 Dim denom As Double
  denom = Sqr((n_data * sumxx - sumx * sumx) * (n_data * sumyy - sumy *
sumy))
  If denom > 0.00000000001 Then
  rsquare = (n_data * sumxy - sumx * sumy) / denom
 Else
 rsquare = 1
 End If
    .BottomTitle = .BottomTitle & "  R^2 = " & Format(rsquare, "0.000")
    .DrawMode = graphDraw
  End With
 End Sub Private Sub chk_sort_col_Click()
 If chk_sort_col.value = 1 Then
 1st_sort_col.Enabled = True
 Else
 1st_sort_col.Enabled = False
 End If
 End Sub Private Sub chk_trend_line_Click()
 If chk_trend_line.value = 1 Then
 opt_line.Enabled = True
 opt_smooth.Enabled = True
 Else opt_line.Enabled = False
 opt_smooth.Enabled = False
 End If
 End Sub Private Sub copy_Click()
 MsgBox "Nothing to copy"
 End Sub
```

FIG. 8A-81

File frm_histo.frm

```
VERSION 5.00
Object = "{BDC217C8-ED16-11CD-956C-0000C04E4C0A}#1.1#0"; "TABCTL32.OCX"
Object = "{827E9F53-96A4-11CF-823E-000021570103}#1.0#0"; "GRAPHS32.OCX"
Begin VB.Form frm_histo
   Caption         =   "Make Histograms"
   ClientHeight    =   9045
   ClientLeft      =   60
   ClientTop       =   630
   ClientWidth     =   12120
   LinkTopic       =   "Form1"
   ScaleHeight     =   9045
   ScaleWidth      =   12120
   StartUpPosition =   3  'Windows Default
   Begin VB.TextBox txt_nbins
      Height       =   285
      Left         =   1320
      TabIndex     =   14
      Text         =   "10"
      Top          =   6480
      Width        =   855
   End
   Begin VB.CheckBox chk_autobins
      Caption      =   "Auto select bins"
      Height       =   375
      Left         =   480
      TabIndex     =   12
      Top          =   5880
      Width        =   1695
   End
   Begin VB.Frame Frame4
      Height       =   1095
      Left         =   360
      TabIndex     =   9
      Top          =   4560
      Width        =   1695
      Begin VB.OptionButton opt_lin
         Caption   =   "Linear scale"
         Height    =   255
         Left      =   240
         TabIndex  =   11
         Top       =   240
         Value     =   -1  'True
         Width     =   1215
      End
      Begin VB.OptionButton opt_log
         Caption   =   "log scale"
         Height    =   255
         Left      =   240
         TabIndex  =   10
         Top       =   600
         Width     =   1095
      End
   End
   Begin VB.TextBox txt_n_rows
      Height       =   405
```

FIG. 8A-82

```
        Left            =   1680
        TabIndex        =   8
        Text            =   "1"
        Top             =   3840
        Width           =   495
    End
    Begin VB.Frame Frame3
        Height          =   1095
        Left            =   360
        TabIndex        =   5
        Top             =   3240
        Width           =   1935
        Begin VB.OptionButton opt_matrix
            Caption     =   "Matrix"
            Height      =   195
            Left        =   240
            TabIndex    =   7
            Top         =   600
            Width       =   1575
        End
        Begin VB.OptionButton opt_ind_plots
            Caption     =   "Individual plots"
            Height      =   195
            Left        =   240
            TabIndex    =   6
            Top         =   240
            Value       =   -1  'True
            Width       =   1575
        End
    End
    Begin VB.ListBox lst_histo
        Height          =   2595
        Left            =   480
        TabIndex        =   4
        Top             =   360
        Width           =   1335
    End
    Begin VB.CommandButton but_done
        Caption         =   "Done"
        Height          =   615
        Left            =   720
        TabIndex        =   2
        Top             =   7800
        Width           =   1215
    End
    Begin VB.CommandButton but_make_plot
        Caption         =   "Make Histo"
        Height          =   615
        Left            =   720
        TabIndex        =   1
        Top             =   6960
        Width           =   1215
    End
    Begin TabDlg.SSTab tab_histo
        Height          =   8775
        Left            =   2520
        TabIndex        =   0
```

FIG. 8A-83

```
Top              =   0
Width            =   9495
_ExtentX         =   16748
_ExtentY         =   15478
_Version         =   327681
TabOrientation   =   1
Tabs             =   1
TabsPerRow       =   5
TabHeight        =   520
TabPicture(0)    =   "frm_histo.frx":0000
Tab(0).ControlEnabled=    -1  'True
Tab(0).Control(0)=   "Graph(0)"
Tab(0).Control(0).Enabled=    0   'False
Tab(0).ControlCount=   1
Begin GraphsLib.Graph Graph
    Height       =   375
    Index        =   0
    Left         =   480
    TabIndex     =   3
    Top          =   480
    Visible      =   0   'False
    Width        =   615
    _Version     =   327680
    _ExtentX     =   1085
    _ExtentY     =   661
    _StockProps  =   96
    BorderStyle  =   1
    GraphType    =   3
    RandomData   =   0
End
End
Begin VB.Label Label2
    Caption      =   "n bins"
    Height       =   255
    Left         =   480
    TabIndex     =   13
    Top          =   6480
    Width        =   735
End
Begin VB.Menu file
    Caption      =   "File"
    Begin VB.Menu exit
        Caption      =   "Exit"
    End
End
Begin VB.Menu edit
    Caption      =   "Edit"
    Begin VB.Menu copy
        Caption      =   "&Copy"
        Shortcut     =   ^C
    End
End
End
Attribute VB_Name = "frm_histo"
Attribute VB_GlobalNameSpace = False
Attribute VB_Creatable = False
Attribute VB_PredeclaredId = True
```

FIG. 8A-84

```
Attribute VB_Exposed = False
  Private cur_plot As Integer
Private Sub but_make_plot_Click()
Dim i As Integer, n_tabs As Integer, n_plots As Integer
If lst_histo.ListIndex < 0 Then
  MsgBox "Please select one or more x variables"
  Exit Sub
End If
' figure out how may x and y selected
Dim n_x As Integer, xs(1 To 20) As Integer For i = 0 To lst_histo.ListCount - 1
If lst_histo.Selected(i) = True Then
n_x = n_x + 1
xs(n_x) = i
End If
Next i
n_tabs = tab_histo.Tabs
' only add a tab if this is not the first
n_plots = Graph.Count - 1 ' index starts at 0, but we don't use 0
  If n_plots = 0 Then n_tabs = 0
If n_x = 1 Then
  n_tabs = n_tabs + 1
n_plots = n_plots + 1
tab_histo.Tabs = n_tabs
tab_histo.Tab = n_tabs - 1
tab_histo.TabCaption(n_tabs - 1) = lst_histo.list(lst_histo.ListIndex)
Load Graph(n_plots)
With Graph(n_plots)
   .Visible = True
   .Enabled = True
   .Top = 400
   .Left = 400
   .width = 9200
   .height = 7400
   ' how many data
  n_data = frm_graphics.spr_data.MaxRows
   .NumSets = 1
   .NumPoints = n_data
make_histo lst_histo.ListIndex + 1, Graph(n_plots)

End With
End If

End Sub

Sub make_histo(X As Integer, this_graph As Graph)

End Sub

Private Sub chk_autobins_Click()
If chk_autobins.value = 0 Then
txt_nbins.Enabled = True
Else
txt_nbins.Enabled = False
End If
End Sub
```

FIG. 8A-85

```
Private Sub copy_Click()
If cur_plot = 0 Then
MsgBox "Please select a plot"
Else
Graph(cur_plot).DrawMode = graphCopy
End If
End Sub Private Sub exit_Click()
frm_graphics.Show
Me.Hide
End Sub Private Sub Form_Terminate()
frm_graphics.Show
End Sub Private Sub Graph_Click(Index As Integer)
cur_plot = Index
End Sub
```

FIG. 8A-86

File frm_intermediate_results.frm

```
VERSION 5.00
Object = "{B02F3647-766B-11CE-AF28-C3A2FBE76A13}#2.5#0"; "SS32X25.OCX"
Object = "{02B5E320-7292-11CF-93D5-0020AF99504A}#1.0#0"; "MSCHART.OCX"
Object = "{BDC217C8-ED16-11CD-956C-0000C04E4C0A}#1.1#0"; "TABCTL32.OCX"
Object = "{6B7E6392-850A-101B-AFC0-4210102A8DA7}#1.2#0"; "COMCTL32.OCX"
Begin VB.Form frm_inter_results
   Caption         =   "Intermediate results"
   ClientHeight    =   7290
   ClientLeft      =   3015
   ClientTop       =   4380
   ClientWidth     =   12600
   LinkTopic       =   "Form1"
   ScaleHeight     =   7290
   ScaleWidth      =   12600
   Begin ComctlLib.ProgressBar pgb_ind
      Height          =   210
      Left            =   2280
      TabIndex        =   4
      Top             =   6480
      Width           =   5175
      _ExtentX        =   9128
      _ExtentY        =   370
      _Version        =   327682
      Appearance      =   1
   End
   Begin TabDlg.SSTab SSTab1
      Height          =   6255
      Left            =   120
      TabIndex        =   1
      Top             =   120
      Width           =   12255
      _ExtentX        =   21616
      _ExtentY        =   11033
      _Version        =   393216
      TabOrientation  =   3
      Tabs            =   2
      TabsPerRow      =   2
      TabHeight       =   520
      BeginProperty Font {0BE35203-8F91-11CE-9DE3-00AA004BB851}
         Name            =   "Arial"
         Size            =   11.25
         Charset         =   0
         Weight          =   400
         Underline       =   0   'False
         Italic          =   0   'False
         Strikethrough   =   0   'False
      EndProperty
      TabCaption(0)   =   "Intermediate results"
      TabPicture(0)   =   "frm_intermediate_results.frx":0000
      Tab(0).ControlEnabled=   -1  'True
      Tab(0).Control(0)=   "MSChart1"
      Tab(0).Control(0).Enabled=   0   'False
      Tab(0).ControlCount=   1
      TabCaption(1)   =   "Final Results"
      TabPicture(1)   =   "frm_intermediate_results.frx":001C
```

FIG. 8A-87

```
Tab(1).ControlEnabled=    0    'False
Tab(1).Control(0)=    "spr_result"
Tab(1).ControlCount=   1
Begin MSChartLib.MSChart MSChart1
    Height          =   5655
    Left            =   1200
    OleObjectBlob   =   "frm_intermediate_results.frx":0038
    TabIndex        =   2
    Top             =   120
    Width           =   10335
End
Begin FPSpread.vaSpread spr_result
    Height          =   5895
    Left            =   -74880
    TabIndex        =   3
    Top             =   120
    Width           =   11520
    _Version        =   131077
    _ExtentX        =   20320
    _ExtentY        =   10398
    _StockProps     =   64
    BeginProperty Font {0BE35203-8F91-11CE-9DE3-00AA004BB851}
        Name            =   "MS Sans Serif"
        Size            =   8.25
        Charset         =   0
        Weight          =   700
        Underline       =   0    'False
        Italic          =   0    'False
        Strikethrough   =   0    'False
    EndProperty
    MaxCols         =   14
    ScrollBars      =   2
    ScrollBarShowMax=   0    'False
    SpreadDesigner  =   "frm_intermediate_results.frx":20C4
    UserResize      =   2
    VisibleCols     =   500
    VisibleRows     =   500
End
End
Begin VB.CommandButton but_stop_run
    Caption         =   "Stop Run"
    Height          =   375
    Left            =   9840
    TabIndex        =   0
    Top             =   6600
    Width           =   855
End
Begin ComctlLib.ProgressBar pgb_gen
    Height          =   210
    Left            =   2280
    TabIndex        =   5
    Top             =   6840
    Width           =   5175
    _ExtentX        =   9128
    _ExtentY        =   370
    _Version        =   327682
    Appearance      =   1
```

FIG. 8A-88
```
    End
    Begin VB.Label Label2
        Caption         =   "Generations"
        Height          =   255
        Left            =   840
        TabIndex        =   7
        Top             =   6840
        Width           =   1095
    End
    Begin VB.Label Label1
        Caption         =   "Individuals"
        Height          =   255
        Left            =   840
        TabIndex        =   6
        Top             =   6480
        Width           =   975
    End
End
Attribute VB_Name = "frm_inter_results"
Attribute VB_GlobalNameSpace = False
Attribute VB_Creatable = False
Attribute VB_PredeclaredId = True
Attribute VB_Exposed = False
Option Explicit Private Sub but_stop_run_Click()
stop_run = True
End Sub Private Sub spr_result_Click(ByVal Col As Long, ByVal Row As Long)
If Col > 4 And Col < 13 Then MsgBox "col = " & Col & "  row = " & Row
End Sub
```

FIG. 8A-89

```
File frm_new_group.frm
VERSION 5.00
Begin VB.Form frm_new_group
    Caption         =   "New Token Group"
    ClientHeight    =   3195
    ClientLeft      =   5220
    ClientTop       =   3735
    ClientWidth     =   4680
    LinkTopic       =   "Form1"
    ScaleHeight     =   3195
    ScaleWidth      =   4680
    Begin VB.TextBox txt_stem
        Height      =   375
        Left        =   1440
        TabIndex    =   4
        Top         =   720
        Width       =   1455
    End
    Begin VB.TextBox txt_n_tokens
        Height      =   375
        Left        =   1440
        TabIndex    =   2
        Text        =   "1"
        Top         =   1200
        Width       =   1455
    End
    Begin VB.CommandButton but_cancel
        Caption     =   "Cancel"
        Height      =   495
        Left        =   2400
        TabIndex    =   1
        Top         =   2400
        Width       =   1335
    End
    Begin VB.CommandButton but_done
        Caption     =   "Done"
        Height      =   495
        Left        =   720
        TabIndex    =   0
        Top         =   2400
        Width       =   1335
    End
    Begin VB.Label Label2
        Caption     =   "Stem "
        Height      =   375
        Left        =   240
        TabIndex    =   5
        Top         =   720
        Width       =   975
    End
    Begin VB.Label Label1
        Caption     =   "# of Tokens"
        Height      =   375
        Left        =   240
        TabIndex    =   3
        Top         =   1200
```

FIG. 8A-90

```
        Width           =   975
    End
End
Attribute VB_Name = "frm_new_group"
Attribute VB_GlobalNameSpace = False
Attribute VB_Creatable = False
Attribute VB_PredeclaredId = True
Attribute VB_Exposed = False Private Sub but_cancel_Click()
Me.txt_n_tokens = -999
Me.txt_stem = -999
Me.Hide
frm_tokens.Show
End Sub Private Sub but_done_Click()
Me.Hide
frm_tokens.Show
End Sub
```

FIG. 8A-91

File frm_options.frm

```
VERSION 5.00
Begin VB.Form frm_options
   Caption         =   "Form1"
   ClientHeight    =   7485
   ClientLeft      =   5265
   ClientTop       =   3360
   ClientWidth     =   8625
   LinkTopic       =   "Form1"
   ScaleHeight     =   7485
   ScaleWidth      =   8625
   Begin VB.CheckBox chk_save_best
      Caption         =   "Save best?"
      Height          =   255
      Left            =   4800
      TabIndex        =   43
      Top             =   3960
      Value           =   1  'Checked
      Width           =   3135
   End
   Begin VB.Frame Frame2
      Caption         =   "Random seed"
      Height          =   1455
      Left            =   4680
      TabIndex        =   38
      Top             =   4440
      Width           =   3495
      Begin VB.TextBox txt_rnd_seed
         Enabled         =   0  'False
         Height          =   375
         Left            =   2040
         TabIndex        =   42
         Text            =   "1"
         Top             =   840
         Width           =   615
      End
      Begin VB.OptionButton opt_rnd_user
         Caption         =   "User Defined"
         Height          =   255
         Left            =   240
         TabIndex        =   41
         Top             =   960
         Width           =   1335
      End
      Begin VB.OptionButton opt_rnd_default
         Caption         =   "Use Default"
         Height          =   255
         Left            =   240
         TabIndex        =   40
         Top             =   240
         Value           =   -1  'True
         Width           =   1335
      End
      Begin VB.OptionButton opt_rnd_clock
         Caption         =   "Use Clock"
         Height          =   255
```

FIG. 8A-92

```
        Left            =   240
        TabIndex        =   39
        Top             =   600
        Width           =   1335
    End
End
Begin VB.CheckBox chk_non_diag_omega
    Caption         =   "Include ga for non diagonal OMEGA"
    Height          =   375
    Left            =   4800
    TabIndex        =   37
    Top             =   3480
    Value           =   1  'Checked
    Width           =   2895
End
Begin VB.TextBox txt_frame_shift_prob
    Height          =   285
    Left            =   2760
    TabIndex        =   35
    Text            =   "0.01"
    Top             =   1320
    Width           =   1455
End
Begin VB.CheckBox chk_save_output
    Caption         =   "Save output file"
    Height          =   375
    Left            =   4800
    TabIndex        =   34
    Top             =   3000
    Value           =   1  'Checked
    Width           =   2775
End
Begin VB.CheckBox chk_save_control
    Caption         =   "Save control file"
    Height          =   375
    Left            =   4800
    TabIndex        =   33
    Top             =   2640
    Value           =   1  'Checked
    Width           =   2775
End
Begin VB.TextBox txt_generations
    Height          =   285
    Left            =   2760
    TabIndex        =   31
    Text            =   "20"
    Top             =   6120
    Width           =   1455
End
Begin VB.TextBox txt_succ_crit
    Height          =   285
    Left            =   2760
    TabIndex        =   29
    Text            =   "0.3"
    Top             =   5160
    Width           =   1455
End
```

FIG. 8A-93

```
Begin VB.TextBox txt_corr_crit
    Height      =   285
    Left        =   2760
    TabIndex    =   27
    Text        =   "50"
    Top         =   3720
    Width       =   1455
End
Begin VB.TextBox txt_lower_limit
    Height      =   285
    Left        =   2760
    TabIndex    =   24
    Text        =   "0.3"
    Top         =   4680
    Width       =   1455
End
Begin VB.TextBox txt_upper_limit
    Height      =   285
    Left        =   2760
    TabIndex    =   23
    Text        =   "2"
    Top         =   4200
    Width       =   1455
End
Begin VB.TextBox txt_cov_crit
    Height      =   285
    Left        =   2760
    TabIndex    =   21
    Text        =   "1000"
    Top         =   3240
    Width       =   1455
End
Begin VB.Frame Frame1
    Caption     =   "NONMEM call"
    Height      =   1095
    Left        =   4440
    TabIndex    =   18
    Top         =   360
    Width       =   2535
    Begin VB.OptionButton opt_dll
        Caption     =   "DLL (NT only)"
        Height      =   255
        Left        =   120
        TabIndex    =   20
        Top         =   240
        Width       =   1455
    End
    Begin VB.OptionButton opt_exe
        Caption     =   "EXE (NT or 9?)"
        Height      =   255
        Left        =   120
        TabIndex    =   19
        Top         =   600
        Value       =   -1  'True
        Width       =   1935
    End
End
```

FIG. 8A-94

```
Begin VB.TextBox txt_pop_size
    Height      =   285
    Left        =   2760
    TabIndex    =   16
    Text        =   "50"
    Top         =   5640
    Width       =   1455
End
Begin VB.OptionButton opt_2runs
    Caption     =   "2"
    Height      =   375
    Left        =   6720
    TabIndex    =   14
    Top         =   1920
    Width       =   855
End
Begin VB.OptionButton opt_4runs
    Caption     =   "4"
    Height      =   375
    Left        =   6720
    TabIndex    =   13
    Top         =   2280
    Value       =   -1   'True
    Width       =   855
End
Begin VB.OptionButton opt_1run
    Caption     =   "1"
    Height      =   375
    Left        =   6720
    TabIndex    =   12
    Top         =   1560
    Width       =   855
End
Begin VB.TextBox txt_sigma_crit
    Height      =   285
    Left        =   2760
    TabIndex    =   10
    Text        =   "7.84"
    Top         =   2760
    Width       =   1455
End
Begin VB.TextBox txt_theta_crit
    Height      =   285
    Left        =   2760
    TabIndex    =   7
    Text        =   "7.84"
    Top         =   1800
    Width       =   1455
End
Begin VB.TextBox txt_omega_crit
    Height      =   285
    Left        =   2760
    TabIndex    =   6
    Text        =   "7.84"
    Top         =   2280
    Width       =   1455
End
```

FIG. 8A-95

```
Begin VB.TextBox txt_cross_over_freq
    Height      =   285
    Left        =   2760
    TabIndex    =   4
    Text        =   "0.8"
    Top         =   360
    Width       =   1455
End
Begin VB.TextBox txt_mutation_rate
    Height      =   285
    Left        =   2760
    TabIndex    =   2
    Text        =   "0.001"
    Top         =   840
    Width       =   1455
End
Begin VB.CommandButton but_cancel
    Caption     =   "Cancel"
    Height      =   495
    Left        =   4680
    TabIndex    =   1
    Top         =   6720
    Width       =   1095
End
Begin VB.CommandButton but_done
    Caption     =   "Done"
    Height      =   495
    Left        =   2280
    TabIndex    =   0
    Top         =   6720
    Width       =   1095
End
Begin VB.Label Label8
    Caption     =   "Frame Shift Probability"
    Height      =   255
    Left        =   240
    TabIndex    =   36
    Top         =   1320
    Width       =   1695
End
Begin VB.Label Label14
    Caption     =   "Generation limit"
    Height      =   255
    Left        =   240
    TabIndex    =   32
    Top         =   6120
    Width       =   1455
End
Begin VB.Label Label13
    Caption     =   "Success Criteria"
    Height      =   255
    Left        =   240
    TabIndex    =   30
    Top         =   5160
    Width       =   2055
End
Begin VB.Label Label12
```

FIG. 8A-96

```
        Caption         =   "Penalty for corr > 0.95"
        Height          =   255
        Left            =   240
        TabIndex        =   28
        Top             =   3720
        Width           =   2055
End
Begin VB.Label Label11
        Caption         =   "Lower limit of scaled fitness"
        Height          =   255
        Left            =   240
        TabIndex        =   26
        Top             =   4680
        Width           =   2055
End
Begin VB.Label Label10
        Caption         =   "Upper limit of scaled fitness"
        Height          =   255
        Left            =   240
        TabIndex        =   25
        Top             =   4200
        Width           =   2295
End
Begin VB.Label Label9
        Caption         =   "Covariance criteria"
        Height          =   255
        Left            =   240
        TabIndex        =   22
        Top             =   3240
        Width           =   1335
End
Begin VB.Label Label7
        Caption         =   "Population size"
        Height          =   255
        Left            =   240
        TabIndex        =   17
        Top             =   5640
        Width           =   1095
End
Begin VB.Label Label6
        Caption         =   "Number of threads"
        Height          =   255
        Left            =   4920
        TabIndex        =   15
        Top             =   1800
        Width           =   1695
End
Begin VB.Label Label5
        Caption         =   "Sigma criteria"
        Height          =   255
        Left            =   240
        TabIndex        =   11
        Top             =   2760
        Width           =   1335
End
Begin VB.Label Label4
        Caption         =   "Omega criteria"
```

FIG. 8A-97

```
            Height          =   255
            Left            =   240
            TabIndex        =   9
            Top             =   2280
            Width           =   1335
         End
         Begin VB.Label Label3
            Caption         =   "Theta Criteria"
            Height          =   255
            Left            =   240
            TabIndex        =   8
            Top             =   1800
            Width           =   1695
         End
         Begin VB.Label Label2
            Caption         =   "Cross over Frequency"
            Height          =   255
            Left            =   240
            TabIndex        =   5
            Top             =   240
            Width           =   1695
         End
         Begin VB.Label Label1
            Caption         =   "Mutation rate"
            Height          =   255
            Left            =   240
            TabIndex        =   3
            Top             =   840
            Width           =   975
         End
      End
End
Attribute VB_Name = "frm_options"
Attribute VB_GlobalNameSpace = False
Attribute VB_Creatable = False
Attribute VB_PredeclaredId = True
Attribute VB_Exposed = False Private Sub but_cancel_Click()
Me.Hide
frm_main.Show
End Sub Private Sub but_done_Click()
mutation_rate = Me.txt_mutation_rate
cross_over_freq = Me.txt_cross_over_freq
frame_shift_prob = Me.txt_frame_shift_prob
theta_crit = Me.txt_theta_crit
omega_crit = Me.txt_omega_crit
sigma_crit = Me.txt_sigma_crit
cov_crit = Me.txt_cov_crit
success_crit = Me.txt_succ_crit
generation_limit = Me.txt_generations
lower_fitness_limit = Me.txt_lower_limit
upper_fitness_limit = Me.txt_upper_limit
seed_value = Me.txt_rnd_seed.text
If Me.opt_rnd_clock = True Then seed_type = "clock"
If Me.opt_rnd_default = True Then seed_type = "default"
```

FIG. 8A-98

```
If Me.opt_rnd_user = True Then seed_type = "user"
corr_crit = Me.txt_corr_crit
If opt_dll = True Then call_method = "dll"
If opt_exe = True Then call_method = "exe"
If chk_save_control = 1 Then
save_control = True
Else
save_control = False
End If
If chk_save_best = 1 Then
save_best = True
Else
save_best = False
End If
If chk_save_output = 1 Then
save_output = True
Else
save_output = False
End If
pop_size = Me.txt_pop_size
If pop_size Mod 2 <> 0 Then
MsgBox "Population size must be even number"
Me.txt_pop_size.SelStart = 0
Me.txt_pop_size.SelLength = Len(Me.txt_pop_size)
Me.txt_pop_size.SetFocus
Exit Sub
End If
' need to redimension genome for non diagonal omega
Dim g2dim As Integer
If Me.chk_non_diag_omega = 1 Then
 omega_block = True
 Else
 omega_block = False
 End If
Me.Hide
frm_main.Show
End Sub Private Sub chk_non_diag_omega_Click()
If chk_non_diag_omega = True Then
omega_block = True
Else
omega_block = False
End If
End Sub Private Sub Form_Load()
set_options
End Sub
Private Sub opt_both_limit_Click()
txt_time.Enabled = True
txt_generations.Enabled = True
End Sub Private Sub opt_generations_Click()
   txt_time.Enabled = False
txt_generations.Enabled = True
```

FIG. 8A-99

```
End Sub
Private Sub opt_time_Click()
   txt_time.Enabled = True
txt_generations.Enabled = False
End Sub Private Sub opt_rnd_clock_Click()
seed_type = "clock"
Me.txt_rnd_seed.Enabled = False
End Sub Private Sub opt_rnd_default_Click()
seed_type = "default"
Me.txt_rnd_seed.Enabled = False
End Sub Private Sub opt_rnd_user_Click()
seed_type = "user"
Me.txt_rnd_seed.Enabled = True End Sub Private Sub txt_rnd_seed_lostfocus()
On Error GoTo num_error
seed_value = Me.txt_rnd_seed Exit Sub
num_error:
MsgBox ("Please enter a number")
Me.txt_rnd_seed.SetFocus
Me.txt_rnd_seed.SelStart = 0
Me.txt_rnd_seed.SelLength = Len(Me.txt_rnd_seed.text)

On Error Resume Next
End Sub
```

FIG. 8A-100

File frm_results.frm

```
VERSION 5.00
Object = "{B02F3647-766B-11CE-AF28-C3A2FBE76A13}#2.5#0"; "SS32X25.OCX"
Begin VB.Form frm_results
   Caption         =   "Results"
   ClientHeight    =   8490
   ClientLeft      =   60
   ClientTop       =   345
   ClientWidth     =   13245
   LinkTopic       =   "Form1"
   ScaleHeight     =   8490
   ScaleWidth      =   13245
   StartUpPosition =   3  'Windows Default
   Begin FPSpread.vaSpread spr_result
      Height       =   6255
      Left         =   360
      TabIndex     =   1
      Top          =   480
      Width        =   12480
      _Version     =   131077
      _ExtentX     =   22013
      _ExtentY     =   11033
      _StockProps  =   64
      BeginProperty Font {0BE35203-8F91-11CE-9DE3-00AA004BB851}
         Name          =   "MS Sans Serif"
         Size          =   8.25
         Charset       =   0
         Weight        =   700
         Underline     =   0   'False
         Italic        =   0   'False
         Strikethrough =   0   'False
      EndProperty
      MaxCols          =   12
      ScrollBars       =   2
      ScrollBarShowMax =   0   'False
      SpreadDesigner   =   "frm_results.frx":0000
      UserResize       =   2
      VisibleCols      =   500
      VisibleRows      =   500
   End
   Begin VB.CommandButton but_done
      Caption      =   "Done"
      Height       =   615
      Left         =   6120
      TabIndex     =   0
      Top          =   7680
      Width        =   1095
   End
End
Attribute VB_Name = "frm_results"
Attribute VB_GlobalNameSpace = False
Attribute VB_Creatable = False
Attribute VB_PredeclaredId = True
Attribute VB_Exposed = False
Option Explicit
Private Sub but_done_Click()
```

FIG. 8A-101

```
Me.Hide
End Sub
Private Sub spr_result_Click(ByVal Col As Long, ByVal Row As Long)
If Col > 4 Then MsgBox "col = " & Col & "  row = " & Row
End Sub
```

FIG. 8A-102

File frm_sort_results.frm

```
VERSION 5.00
Begin VB.Form frm_sort_results
   Caption          =   "Sort Results"
   ClientHeight     =   3975
   ClientLeft       =   60
   ClientTop        =   345
   ClientWidth      =   6930
   LinkTopic        =   "Form1"
   ScaleHeight      =   3975
   ScaleWidth       =   6930
   StartUpPosition  =   3  'Windows Default
   Begin VB.CommandButton but_cancel
      Caption       =   "Cancel"
      Height        =   495
      Left          =   3720
      TabIndex      =   7
      Top           =   3240
      Width         =   1095
   End
   Begin VB.CommandButton but_Sort
      Caption       =   "Sort"
      Height        =   495
      Left          =   1920
      TabIndex      =   6
      Top           =   3240
      Width         =   1095
   End
   Begin VB.ListBox lst_third_sort
      Height        =   1230
      ItemData      =   "frm_sort_results.frx":0000
      Left          =   4800
      List          =   "frm_sort_results.frx":0016
      TabIndex      =   4
      Top           =   1320
      Width         =   1335
   End
   Begin VB.ListBox lst_second_sort
      Height        =   1230
      ItemData      =   "frm_sort_results.frx":004E
      Left          =   2640
      List          =   "frm_sort_results.frx":0064
      TabIndex      =   2
      Top           =   1320
      Width         =   1335
   End
   Begin VB.ListBox lst_first_sort
      Height        =   1230
      ItemData      =   "frm_sort_results.frx":009C
      Left          =   600
      List          =   "frm_sort_results.frx":00B2
      TabIndex      =   0
      Top           =   1320
      Width         =   1335
   End
   Begin VB.Label Label3
```

FIG. 8A-103

```
        Caption         =   "Third Sort Variable"
        Height          =   375
        Left            =   4800
        TabIndex        =   5
        Top             =   720
        Width           =   1335
     End
     Begin VB.Label Label2
        Caption         =   "Second Sort Variable"
        Height          =   375
        Left            =   2520
        TabIndex        =   3
        Top             =   720
        Width           =   1815
     End
     Begin VB.Label Label1
        Caption         =   "First Sort Variable"
        Height          =   375
        Left            =   480
        TabIndex        =   1
        Top             =   720
        Width           =   1335
     End
End
Attribute VB_Name = "frm_sort_results"
Attribute VB_GlobalNameSpace = False
Attribute VB_Creatable = False
Attribute VB_PredeclaredId = True
Attribute VB_Exposed = False Private Sub but_cancel_Click()
Me.Hide
Unload Me End Sub Private Sub but_Sort_Click()
Dim max_val As Single, max_dig As Integer, fformat As String
max_val = -99999999
Me.Hide
'setup_data
With frm_main.spr_result
' if using columns 1 or 4, format the data
If Me.lst_first_sort.ListIndex = 0 Or Me.lst_second_sort.ListIndex = 0 _
Or Me.lst_third_sort.ListIndex = 0 Then col_format (1)
If Me.lst_first_sort.ListIndex = 3 Or Me.lst_second_sort.ListIndex = 3 _
Or Me.lst_third_sort.ListIndex = 3 Then col_format (4)
If Me.lst_first_sort.ListIndex = 4 Or Me.lst_second_sort.ListIndex = 4 _
Or Me.lst_third_sort.ListIndex = 4 Then col_format (8)
If Me.lst_first_sort.ListIndex = 5 Or Me.lst_second_sort.ListIndex = 5 _
Or Me.lst_third_sort.ListIndex = 5 Then col_format (9)
Dim key1 As Integer, key2 As Integer, key3 As Integer
    If Me.lst_first_sort.ListIndex = -1 Then
```

FIG. 8A-104

```
MsgBox ("Please select one or more sort keys")
Exit Sub
End If
key1 = Me.lst_first_sort.ListIndex + 1
If key1 = 5 Then key1 = 8
If key1 = 6 Then key1 = 9
key2 = Me.lst_second_sort.ListIndex + 1
If key2 = 5 Then key2 = 8
If key2 = 6 Then key2 = 9
key3 = Me.lst_third_sort.ListIndex + 1
If key3 = 5 Then key3 = 8
If key3 = 6 Then key1 = 9

.col = 1
.Col2 = 9
.row = 1
.Row2 = run_number
.SortKey(1) = key1
.SortKeyOrder(1) = 1
If key2 > 0 Then
.SortKey(2) = key2
.SortKeyOrder(2) = 1
End If
If key3 > 0 Then
.SortKey(3) = key3
.SortKeyOrder(3) = 1
End If
' we need to format columns 1 and 4
If key1 = 2 Or key1 = 3 Then .SortKeyOrder(1) = 2
If key2 = 2 Or key2 = 3 Then .SortKeyOrder(2) = 2
If key3 = 2 Or key3 = 3 Then .SortKeyOrder(3) = 2
.SortBy = 0
.Action = 25
If Me.lst_first_sort.ListIndex = 0 Or Me.lst_second_sort.ListIndex = 0
_
Or Me.lst_third_sort.ListIndex = 0 Then col_unformat (1)
If Me.lst_first_sort.ListIndex = 3 Or Me.lst_second_sort.ListIndex = 3
_
Or Me.lst_third_sort.ListIndex = 3 Then col_unformat (4)
If Me.lst_first_sort.ListIndex = 4 Or Me.lst_second_sort.ListIndex = 4
_
Or Me.lst_third_sort.ListIndex = 4 Then col_unformat (8)
If Me.lst_first_sort.ListIndex = 5 Or Me.lst_second_sort.ListIndex = 5
_
Or Me.lst_third_sort.ListIndex = 5 Then col_unformat (9)
End With
Unload Me
End Sub
Sub col_format(col1 As Integer)
Dim this_row As Integer, max_val As Single, max_dig As Integer
max_val = -99999999
With frm_main.spr_result
  .col = col1
For this_row = 1 To run_number
  .row = this_row
  If Val(.text) > max_val Then max_val = Val(.text)
Next this_row
```

FIG. 8A-105

```
    If max_val <> 0 Then
max_dig = Log(max_val) / Log(10)
Else
MsgBox ("results cannot be sorted")
Exit Sub
End If
fformat = String(max_dig + 1, "0") & "." & String(8 - max_dig, "#")
' and format all the data
For this_row = 1 To run_number
.row = this_row
.text = Format(Val(.text), fformat)
Next this_row
End With
End Sub
Sub setup_data()
Dim this_row As Integer
With frm_main.spr_result
frm_main.SSTab1.Tab = 2
For this_row = 1 To 40
.row = this_row
.col = 1
.text = (Rnd() * 4) ^ 3
.col = 2
.text = this_row Mod 2
.col = 3
.text = this_row Mod 3
.col = 4
.text = (Rnd() * 4) ^ 3
.col = 8
.text = this_row - (this_row Mod 10)
.col = 9
.text = this_row Mod 10
Next this_row
End With
End Sub
Sub col_unformat(col As Integer)
With frm_main.spr_result
.col = col
For this_row = 1 To run_number
.row = this_row
.text = Val(.text)
Next this_row
End With
End Sub
Sub new_sort()
Dim max_val As Single, max_dig As Integer, fformat As String
max_val = -9999999
Me.Hide
With frm_main.spr_result
For this_row = 1 To 1000
.col = 1
  .row = this_row
  .text = (Rnd() * 10) ^ 3
  If Val(.text) > max_val Then max_val = Val(.text)
.col = 2
  .text = this_row Mod 2
Next this_row
```

FIG. 8A-106

```
max_dig = Log(max_val) / Log(10)
fformat = String(max_dig, "0") & "." & String(10 - max_dig, "#")
' and format all the data
For this_row = 1 To 1000
.col = 1
.row = this_row
.text = Format(Val(.text), fformat)
.col = 2
.text = Format(Val(.text), fformat)
Next this_row
.col = 1
.Col2 = 2
.row = 1
.Row2 = 1000
' read data into array
.SortKey(1) = 2
.SortKey(2) = 1
.SortKeyOrder(1) = 2
.SortKeyOrder(2) = 1
.Action = 25
' and put it back For this_row = 1 To 1000
.col = 1
.row = this_row
.text = Val(.text)
.col = 2
.text = Val(.text)
Next this_row
End With
Unload Me
End Sub
```

FIG. 8A-107

File frm_text.frm

```
VERSION 5.00
Object = "{F9043C88-F6F2-101A-A3C9-08002B2F49FB}#1.1#0"; "Comdlg32.ocx"
Begin VB.Form frm_text
   Caption         =   "Form1"
   ClientHeight    =   10830
   ClientLeft      =   300
   ClientTop       =   630
   ClientWidth     =   15075
   LinkTopic       =   "Form1"
   ScaleHeight     =   10830
   ScaleWidth      =   15075
   Begin MSComDlg.CommonDialog CommonDialog1
      Left            =   2520
      Top             =   1680
      _ExtentX        =   847
      _ExtentY        =   847
      _Version        =   327680
   End
   Begin VB.TextBox txt_text
      BeginProperty Font
         Name            =   "Courier"
         Size            =   9.75
         Charset         =   0
         Weight          =   400
         Underline       =   0    'False
         Italic          =   0    'False
         Strikethrough   =   0    'False
      EndProperty
      Height          =   10815
      Left            =   0
      Locked          =   -1   'True
      MultiLine       =   -1   'True
      ScrollBars      =   3    'Both
      TabIndex        =   0
      Top             =   0
      Width           =   15000
   End
   Begin VB.Menu file
      Caption         =   "File"
      Begin VB.Menu copy
         Caption         =   "Copy"
      End
      Begin VB.Menu exit
         Caption         =   "Exit"
      End
   End
   Begin VB.Menu edit
      Caption         =   "Edit"
      Begin VB.Menu font
         Caption         =   "Font"
      End
   End
End
Attribute VB_Name = "frm_text"
Attribute VB_GlobalNameSpace = False
```

FIG. 8A-108

```vb
Attribute VB_Creatable = False
Attribute VB_PredeclaredId = True
Attribute VB_Exposed = False
Private Sub Command1_Click()
Me.Hide
frm_main.Show
End Sub Private Sub copy_Click()
Dim copy_string As String
If txt_text.SelStart = 0 Then
MsgBox "No text selected"
Exit Sub
End If
copy_string = Mid(txt_text, txt_text.SelStart, txt_text.SelLength)
Clipboard.SetText copy_string      ' Put text on Clipboard.
End Sub Private Sub exit_Click()
Me.Hide
frm_main.Show
End Sub Private Sub font_Click()
CommonDialog1.FontBold = txt_text.FontBold
CommonDialog1.FontItalic = txt_text.FontItalic
CommonDialog1.FontName = txt_text.FontName
CommonDialog1.FontSize = txt_text.FontSize
    CommonDialog1.CancelError = True
      On Error GoTo ErrHandler
      ' Set the Flags property
      CommonDialog1.Flags = cdlCFEffects Or cdlCFBoth
      ' Display the Font dialog box
      CommonDialog1.ShowFont
      txt_text.Font.Name = CommonDialog1.FontName
      txt_text.Font.Size = CommonDialog1.FontSize
      txt_text.Font.Bold = CommonDialog1.FontBold
      txt_text.Font.Italic = CommonDialog1.FontItalic
      txt_text.Font.Underline = CommonDialog1.FontUnderline
      txt_text.FontStrikethru = CommonDialog1.FontStrikethru
      txt_text.ForeColor = CommonDialog1.Color
      Exit Sub
ErrHandler:
      ' User pressed the Cancel button
      Exit Sub 'CommonDialog1.FontBold = txt_text.FontBold
'CommonDialog1.FontItalic = txt_text.FontItalic
'CommonDialog1.FontName = txt_text.FontName
'CommonDialog1.FontSize = txt_text.FontSize
'CommonDialog1.ShowFont
'txt_text.FontName = CommonDialog1.FontName
'txt_text.FontBold = CommonDialog1.FontBold
'txt_text.FontItalic = CommonDialog1.FontItalic
'txt_text.FontSize = CommonDialog1.FontSize
End Sub
```

FIG. 8A-109

```
Private Sub Form_Terminate()
Me.Hide
frm_main.Show
End Sub

Private Sub Form_Unload(Cancel As Integer)
Me.Hide
frm_main.Show
End Sub
```

FIG. 8A-110

File frm_test.frm

```
VERSION 5.00
Begin VB.Form frm_test
   Caption         =   "test"
   ClientHeight    =   5655
   ClientLeft      =   60
   ClientTop       =   345
   ClientWidth     =   6705
   LinkTopic       =   "Form1"
   ScaleHeight     =   5655
   ScaleWidth      =   6705
   StartUpPosition =   3  'Windows Default
   Begin VB.CommandButton Command1
      Caption      =   "done"
      Height       =   255
      Left         =   1680
      TabIndex     =   1
      Top          =   5400
      Width        =   975
   End
   Begin VB.TextBox Text1
      Height       =   4935
      Left         =   480
      MultiLine    =   -1  'True
      TabIndex     =   0
      Text         =   "frm_test.frx":0000
      Top          =   360
      Width        =   6015
   End
End
Attribute VB_Name = "frm_test"
Attribute VB_GlobalNameSpace = False
Attribute VB_Creatable = False
Attribute VB_PredeclaredId = True
Attribute VB_Exposed = False
Private Sub Command1_Click()
Me.Hide
'Unload Me
End Sub
```

FIG. 8A-111

File frm_tokens.frm

```
VERSION 5.00
Begin VB.Form frm_tokens
   Caption         =   "Tokens"
   ClientHeight    =   6360
   ClientLeft      =   1620
   ClientTop       =   1890
   ClientWidth     =   11910
   LinkTopic       =   "Form1"
   ScaleHeight     =   6360
   ScaleWidth      =   11910
   Begin VB.ListBox lst_token_group
      Height          =   3375
      Left            =   9240
      TabIndex        =   10
      Top             =   960
      Width           =   2175
   End
   Begin VB.CommandButton but_remove_group
      Caption         =   "Remove Token Group"
      Height          =   495
      Left            =   10200
      TabIndex        =   9
      Top             =   4680
      Width           =   1575
   End
   Begin VB.CommandButton but_new_group
      Caption         =   "New Token Group"
      Height          =   495
      Left            =   8640
      TabIndex        =   8
      Top             =   4680
      Width           =   1455
   End
   Begin VB.CommandButton but_new_set
      Caption         =   "New Token set"
      Height          =   495
      Left            =   4200
      TabIndex        =   5
      Top             =   4680
      Width           =   1455
   End
   Begin VB.CommandButton but_remove_set
      Caption         =   "Remove Token set"
      Height          =   495
      Left            =   6240
      TabIndex        =   3
      Top             =   4680
      Width           =   1575
   End
   Begin VB.ListBox lst_token_sets
      Height          =   3375
      Left            =   3240
      TabIndex        =   2
      Top             =   960
      Width           =   5295
```

FIG. 8A-112

```
End
Begin VB.ListBox lst_tokens
    Height          =   3375
    Left            =   360
    TabIndex        =   1
    Top             =   960
    Width           =   2535
End
Begin VB.CommandButton but_done
    Caption         =   "Done"
    Height          =   495
    Left            =   4920
    TabIndex        =   0
    Top             =   5760
    Width           =   1695
End
Begin VB.Label Label3
    Caption         =   "Token Groups"
    BeginProperty Font
        Name            =   "MS Sans Serif"
        Size            =   12
        Charset         =   0
        Weight          =   400
        Underline       =   0   'False
        Italic          =   0   'False
        Strikethrough   =   0   'False
    EndProperty
    Height          =   375
    Left            =   8400
    TabIndex        =   11
    Top             =   120
    Width           =   1695
End
Begin VB.Label Label2
    Caption         =   "Token Sets"
    BeginProperty Font
        Name            =   "MS Sans Serif"
        Size            =   12
        Charset         =   0
        Weight          =   400
        Underline       =   0   'False
        Italic          =   0   'False
        Strikethrough   =   0   'False
    EndProperty
    Height          =   375
    Left            =   4800
    TabIndex        =   7
    Top             =   120
    Width           =   1335
End
Begin VB.Label Label1
    Caption         =   "Tokens"
    BeginProperty Font
        Name            =   "MS Sans Serif"
        Size            =   12
        Charset         =   0
        Weight          =   400
```

FIG. 8A-113

```
            Underline       =   0    'False
            Italic          =   0    'False
            Strikethrough   =   0    'False
         EndProperty
         Height          =   375
         Left            =   1080
         TabIndex        =   6
         Top             =   0
         Width           =   1335
      End
      Begin VB.Label lbl_token_name
         Height          =   375
         Left            =   4560
         TabIndex        =   4
         Top             =   480
         Width           =   1935
      End
End
Attribute VB_Name = "frm_tokens"
Attribute VB_GlobalNameSpace = False
Attribute VB_Creatable = False
Attribute VB_PredeclaredId = True
Attribute VB_Exposed = False
Dim curr_group As String
Dim curr_position As Integer ' which token group
Dim curr_token As Integer ' which token
Dim curr_token_set As Integer ' which token set
Private Sub but_done_Click()
Me.Hide
frm_main.Show
End Sub
'
Private Sub but_new_group_Click()
Me.Hide
frm_new_group.txt_n_tokens = ""
frm_new_group.txt_n_tokens = "1"
frm_new_group.Show modal:=1, ownerform:=Me
' n_tokens is set to -999 by cancel
If frm_new_group.txt_n_tokens = "-999" And frm_new_group.txt_stem = "-
999" Then
Exit Sub
End If
n_token_groups = n_token_groups + 1
Dim curr_stem As String
curr_stem = frm_new_group.txt_stem
token_collection(n_token_groups).stem = curr_stem
token_collection(n_token_groups).n_tokens = frm_new_group.txt_n_tokens
lst_token_group.AddItem curr_stem
Me.lbl_token_name = curr_stem
curr_group = curr_stem
curr_position = n_token_groups
lst_token_group.ListIndex = curr_position - 1
'token_collection(curr_position).n_token_sets = 0
token_collection(curr_position).get_token_set lst_token_sets
lst_tokens.clear
End Sub
```

FIG. 8A-114

```
Private Sub but_new_set_Click()
If curr_position > 0 Then
token_collection(curr_position).add_token_set lst_token_sets
curr_token_set = lst_token_sets.ListCount
token_collection(curr_position).get_tokens lst_tokens, curr_token_set
lst_token_sets.ListIndex = lst_token_sets.ListCount - 1
End If
End Sub Private Sub but_remove_group_Click()
Dim this_group As Integer
If lst_token_group.ListIndex > -1 Then
n_token_groups = n_token_groups - 1
 For this_group = lst_token_group.ListIndex + 1 To n_groups - 1
  Set token_collection(this_group) = token_collection(this_group + 1)
 Next this_group
 Set token_collection(n_groups) = Nothing
 lst_token_group.RemoveItem (lst_token_group.ListIndex)
 token_collection(curr_position).get_token_set lst_token_sets
 If lst_token_group.ListCount > 0 Then
 lst_token_group.ListIndex = 0
 Else
 lst_token_group.ListIndex = -1
 lst_token_sets.clear
 End If
  curr_position = 1
  token_collection(curr_position).get_token_set lst_token_sets
 If lst_token_sets.ListCount > 0 Then
 lst_token_sets.ListIndex = 0
 Else
 lst_token_sets.ListIndex = -1
 lst_tokens.clear
 End If
End If
End Sub Private Sub but_remove_set_Click()
If lst_token_sets.ListIndex > -1 Then
token_collection(curr_position).remove_token_set
(lst_token_sets.ListIndex + 1)
token_collection(curr_position).get_token_set lst_token_sets
curr_position = lst_token_group.ListIndex + 1
token_collection(curr_position).get_token_set lst_token_sets
If lst_token_sets.ListCount > 0 Then
lst_token_sets.ListIndex = 0
Else
lst_token_sets.ListIndex = -1
lst_tokens.clear
End If
curr_token_set = lst_token_sets.ListIndex + 1
token_collection(curr_position).get_tokens lst_tokens, curr_token_set
End If
End Sub
```

FIG. 8A-115

```
Private Sub Form_Load()
curr_position = 1
curr_token_set = 1
curr_token = 1
End Sub Private Sub lst_token_group_Click()
curr_group = lst_token_group.list(lst_token_group.ListIndex)
curr_position = lst_token_group.ListIndex + 1
token_collection(curr_position).get_token_set lst_token_sets curr_token_set = 1
If lst_token_sets.ListCount > 0 Then
lst_token_sets.ListIndex = curr_token_set - 1
End If
token_collection(curr_position).get_tokens lst_tokens, curr_token_set
End Sub Private Sub lst_token_sets_Click()
curr_token_set = lst_token_sets.ListIndex + 1
token_collection(curr_position).get_tokens lst_tokens, curr_token_set
End Sub Private Sub lst_tokens_dblClick()
curr_token = lst_tokens.ListIndex + 1
frm_edit_token.txt_token =
token_collection(curr_position).get_token_with_lines(curr_token_set,
curr_token)
Me.Hide frm_edit_token.Show modal:=1, ownerform:=Me
' first change the token in the token set
token_collection(curr_position).set_token curr_token_set, curr_token,
frm_edit_token.txt_token
' update the tokenn list
token_collection(curr_position).get_tokens lst_tokens, curr_token_set
' update token set list
token_collection(curr_position).get_token_set lst_token_sets
End Sub
```

UNSUPERVISED MACHINE LEARNING-BASED MATHEMATICAL MODEL SELECTION

CROSS-REFERENCE TO PROVISIONAL APPLICATION

This application claims the benefit of Provisional Application Ser. No. 60/210,672, filed 10 Jun. 2000, entitled "Unsupervised Machine Learning-Based Mathematical Model Identification", the disclosure of which is hereby incorporated by reference in its entirety as if set forth fully herein.

FIELD OF THE INVENTION

The invention relates to methods, systems and computer program products that are used to identify optimal or near optimal mathematical models. In a preferred embodiment, the mathematical models describe pharmacological concentrations (pharmacokinetic models) or effects of drugs (pharmacodynamic models).

BACKGROUND OF THE INVENTION

Mathematical/statistical models are standard tools in determining how to best use drugs. Models are developed of the time course of the concentration of drugs (referred to as pharmacokinetic models) in various tissues, and the effects of drugs (referred to as pharmacodynamic models). There models are then used to understand the most appropriate dose and dosing interval, as well as whether and how to adjust doses for special populations (elderly, pediatric, patients with various diseases). In addition, these models can be used to simulate a variety of clinical applications (e.g., treatment of different population, different algorithms for adjusting doses and evaluating patient responses), in order to evaluate clinical trial designs (clinical trial simulation) or clinical practice. The current method for identification of the mathematical model that best describes the data (the optimal model) is a complex process based on knowledge of the properties of the drug and trial and error. The current process is best described as a manual binary tree search using forward addition.

NONMEM (Non linear Mixed Effect Model) is a software package developed by the University of California at San Francisco. This software is used to develop mathematical models. Typically these models are of biological response, particularly pharmacokinetic and pharmacodynamic models. NONMEM was the first, and remains the industry standard for developing complex pharmacokinetic/pharmacodynamic models.

Since NONMEM was introduced, a number of other software applications have been developed that have similar capabilities. These include WinNonMix (Pharsight Corporation), Kinetica 2000 Population (Innaphase Corporation), and a procedure in SAS (SAS Institute) called NLMIXED. These applications do essentially the same thing as NONMEM (mixed effect modeling), and the method described herein could be applied to those as well. In addition, these methods could be applied to non-linear regression and logistic regression.

The process of defining a near optimal model in mixed effect non linear regression, non linear regression and logistic regression is commonly called model building. In pharmacokinetic/pharmacodynamic modeling, data from the system of interest (usually a population of patients or normal subjects) is used to estimate the parameters of a mathematical model. Occasionally, attempts are made to break the system of interest down into smaller parts, each of which is then used to estimate the parameters of a model. NONMEM is the industry standard software for estimating parameters for a model, given a data set and a "model". The model is a set of equations (algebraic or differential) that are intended to describe the system of interest. Once the set of equations is identified, the parameters of those equations are estimated (by "fitting") by NONMEM or similar software. The "model building" part consists of an often long process of testing various models (sets of equations) for their ability to describe the observed data. The model is then modified, or rejected and a new model is tested. An example is described below.

Example of Pharmacokinetic Model Building

A study is done in which a single dose of a drug is given to 24 subjects. Plasma samples are collected over the subsequent 24 hours, and the plasma is assayed to determine the concentration of drug. A typical plot of the data from a single subject is shown in FIG. 1. Other subjects might have quite different plots. A mathematical model is sought to describe these data. Specifically, the model that best describes these data (defined as, among other factors the model with the smallest residual error) is sought. The standard pharmacokinetic models for such data consist of a series of linear differential equations. These equations describe the mass transfer of drug from and to one or more "compartments". Compartments in a pharmacokinetic model are hypothetical volumes that contain drug. The differential equations describe the quantity (mass) of drug in the compartment as a function of time. The quantity of drug in a compartment is rarely observed. Rather, the concentration is observed by collecting a sample of a representative tissue (usually blood or plasma) and assaying that sample for the drug.

The model is then used to predict the concentration in the compartment by dividing the quantity of drug by the volume of distribution of the compartment. The volume of distribution of the compartment is a parameter estimated by fitting a model to observed data, using non-linear regression. The compartments used in these models may or may not correspond to any physiologic tissue. The "central compartment" describes the volume from which a plasma sample is collected. This central compartment may correspond to the blood volume, for some drugs (i.e, gentamicin). For other drugs, the central compartment may be larger and correspond to the blood and tissues that equilibrate rapidly with the blood (i.e., mass transfer rate constants are large). The central compartment and any peripheral compartments are defined by the equations that describe the time course of the concentration of drug, not by any physiologic properties.

If the data shown in FIG. 1 are plotted on a log scale, it is noted that a linear plot results. This plot is characteristic of a one compartment model, described by the differential equation:

$$\frac{dA}{dt} = -k \cdot A$$

Where A is the amount of drug in the (single) compartment and k is the mass transfer rate constant out of this compartment (hence the– sign).

The observed plasma concentration then is given as A/V where V is the volume of distribution of this hypothetical compartment. Integrating the equation above, and dividing by V to get the observed drug concentration gives:

$$Concentration = \frac{Dose}{V} \cdot e^{-kt}$$

Where Dose is the administered dose of drug (units of mass), and t is time. This model has two parameters, k and V. NONMEM provides estimates of these parameters, given a data set, and this model.

Other drugs may show two compartment pharmacokinetics. Two compartment pharmacokinetics are described by the differential equations given below.

$$\frac{dA(1)}{dt} = -k \cdot A(1) - k12 \cdot A(1) + k21 \cdot A(2)$$

$$\frac{dA(2)}{dt} = k12 \cdot A(1) - k21 \cdot A(2)$$

This system of two compartments has two volumes, one for the central compartment (1) and one for the peripheral compartment (2). Typically, only the concentration in the central compartment can be observed, since it is, by definition, in rapid equilibrium with the blood. Peripheral compartments may correspond physiological to muscle, adipose tissue, brain tissue etc, or some combination of these.

The two compartment system has five parameters, k (mass transfer rate constant out of compartment 1), k12 (mass transfer rate constant from compartment 1 to 2), k21 (mass transfer rate constant from compartment 2 to 1), V(1) (volume of compartment 1) and V(2) (volume of compartment 2). Other, more complex system (3, 4 or occasionally more compartments) may be appropriate to describe other drugs. In addition to the selection of the number of compartments, a sub-model may best describe each parameter of the model. For example, it is frequently observed that the volume distribution is well described by a linear function of weight, of the form Volume=Θ•weight where Θ is a constant. If this is found to be the case, the equation for a one compartment model becomes:

$$Concentration = \frac{Dose}{\theta \cdot weight} \cdot e^{-kt}$$

Where Θ is a constant describing the relationship between weight and volume.

Similarly, the elimination rate constant (k) may be best described by an expression that includes renal function, liver function, age, race and/or gender. These relationships can be important in understanding how best to administer drugs to special populations such as the elderly, children, or to modify doses to target therapeutic concentrations. In a typical trial, standard demographic descriptors are collected including gender, age, weight, race, as well as clinical laboratory data describing renal function and liver function. Each of these descriptors is typically examined as a potential predictor of at least some of the parameters of the model.

Occasionally, pharmacokinetic data are not well described by a system of linear equations, and non linear equations are employed. As with linear models, there are a finite number of nonlinear models, each with a set of parameters. Again, each parameter is typically examined for a relationship with demographic and laboratory values descriptors (referred to as covariates in the model). Typical non linear kinetics are described by a Michaelis-Menton relationship.[i] This relationship describes a saturable elimination of the drug, with clearance follow the formula:

$$Clearance = \frac{Vmax \cdot Concentration}{Km + Concentration}$$

Where Vmax is the maximum amount of drug that can be eliminated, and Km (Michaelis constant) is the concentration at which one half of the maximum clearance is observed. Vmax and Km may then be functions of covariate (age, weight, renal or liver function).

Linear pharmacokinetic models may be parameterized in more than one way. The simplest may be as rate constants and volumes. Commonly, a clearance can be described instead. Clearance is defined as the product of the volume and the rate constant. Units of clearance are volume/time. The one compartment pharmacokinetic model, parameterized in clearance and volume is given below:

$$Concentration = \frac{Dose}{V} \cdot e^{-(CL/V) \cdot t}$$

Where CL is clearance (units of volume/time) and t is time.

Occasionally, a clearance may be found to correspond to a physiologic process that eliminates drug. For example, gentamicin is eliminated essentially entirely by the kidney. Gentamicin clearance is found to correlate very well with a physiologic flow in the kidney known as the glomerular filtration rate. Other drugs have a clearance essentially equal to kidney blood flow, or liver blood flow. However, in general clearances are regarded as simply parameters that are estimated in fitting a pharmacokinetic model to data.

The equations discussed above describe the "structural model", that is the model that takes a set of inputs (dose, time, weight, age, race etc) and results in a prediction for the observed value (a drug concentration for a pharmacokinetic model). The models described above are mutually exclusive, exactly one can be used in a given model. Presumably, exactly one will be the best of the group. For practical purposes, a number of useful models are enumerated in current pharmacokinetic software (e.g., NONMEM, WinNonMix). NONMEM for example has 12 libraries of pharmacokinetic models. These include one compartment, one compartment with first order absorption, two compartment, two compartment with first order absorption, three compartment, three compartment with first order absorption, a general linear model (1–10 compartments) and a general nonlinear (1–10 compartments) and Michaelis-Menten kinetics.

In practice, the predicted value is rarely equal to the observed value. Rather, the predicted value differs from the observed value by a random variable known in the statistical literature as the residual error (referred to as intra individual error in NONMEM documentation). The mean of all the residual errors (one for each observation) is by definition zero. That is, on average the prediction is equal to the observed value. However, any individual observed value may be higher or lower than the predicted value. Thus, the residual error will be greater or less than zero, but the average of all residual errors will be zero. A statistical model is used to describe the distribution of the residual errors. Typically, for statistical reasons in model fitting, the residual error is assumed to be normally distributed. However, the actual distribution of residual error from the data may be more consistent with other (e.g., skewed) distributions. Thus, it is usually necessary to examine a number models for the residual error as well. Five models of residual error represent the vast majority of work done in pharmacokinetic/pharmacodynamic modeling. These are the additive error, the constant coefficient of variation (CCV), the log normal error, the power model and a combination of the additive and log normal. The functional forms of these models are:

| Model | Functional form |
|---|---|
| Additive | $Y = F + \epsilon$ |
| CCV | $Y = F \cdot (1 + \epsilon)$ |
| Log normal | $Y = F \cdot e^\epsilon$ |
| Power model | $Y = F + \epsilon \cdot \sqrt{(1 + \Theta \cdot F^2)}$ |
| Combined Additive/log | $Y = F \cdot e^{\epsilon(1)} + \epsilon(2)$ |

Where Y is the observed value, F is the predicted value $\Theta$ is an estimated parameter and $\epsilon$ is a random variable with mean zero. The first three models have a single parameter to be fitted, the variance of $\epsilon$, the fourth model has two parameters to be estimated $\Theta$ and the variance of $\epsilon$, and the fifth has two parameters to be fitted, the variance of $\epsilon(1)$ and the variance of $\epsilon(2)$. Additionally, models for autocorrelated residuals can be implemented.

NONMEM is an acronym for NON linear Mixed Effect Model. The mixed effect part of the software refers to the combination of random and fixed effects. In practice this means that the values of parameters are permitted to vary from on person to another. This random effect is statistically entirely analogous to the random effect associated with the residual error. Physiologically, it means that the parameters can vary from one subject in a clinical trial to another. That is, one person will have a larger than average value for the volume of distribution, and another will have a smaller than average value. Frequently some, but not all of this variation is explained by differences in demographic variables (e.g., weight). Similar distributions of parameters can be applied to all the parameters of the model.

Three of the standard models that are applied to the residual error can be applied to this error, referred to in NONMEM as the inter (between individual) error. Unlike residual error however, the observed data may be consistent with no inter individual variability. Therefore, there may be four possible models of inter individual variability.

| Model | Functional form |
|---|---|
| No variability | $P = \tilde{P}$ |
| Additive | $P = \tilde{P} + \eta$ |
| CCV | $P = \tilde{P} \cdot (1 + \eta)$ |
| Log normal | $P = \tilde{P} \cdot e^\eta$ |

Where P is the parameter value for a given individual in the population and $\tilde{P}$ is the mean value for the population. The random variable $\eta$ (ETA) again has a mean of zero and a single parameter, the variance.

The variances of the ETAs are described by the variance-covariance matrix, called OMEGA in NONMEM. This matrix may be diagonal (all off diagonal elements constrained to be 0) or non-diagonal, with some or all the off diagonal elements estimated. Off diagonal elements of OMEGA describe the covariance of the individual parameter values between subjects.

Pharmacodynamic modeling is approached in a similar fashion to pharmacokinetic modeling. A model is sought that describes a given set of observed data. These observed data will include measurements such as blood pressure, cholesterol, HIV viral counts or other quantity that are effected by the administration of drugs. Often, a model consistent with current understanding of the physiology of the drug is sought. However, the underlying goal of the process is to describe the observed data. While some degree of creativity is more frequently observed with pharmacodynamic modeling, a well-defined set of standard model is found to adequately describe the vast majority of continuous systems. These models are:

| Model | Type | Functional form |
|---|---|---|
| Linear | Algebraic | $Y = M \cdot C + B$ |
| Log | Algebraic | $Y = M \cdot Log(C)$ |
| Sigmoid Emax | Algebraic | $Y = (Emax \cdot C^H)/(EC50^H + C^H)$ |
| Indirect response model 1[ii] | Differential | $dY/dt = Kin \cdot (1 - (C/ic50 + C)) - Kout \cdot Y$ |
| Indirect response model 2 | Differential | $dY/dt = Kin - Kout* (1 - (C/(ic50 + C)) \cdot Y$ |
| Indirect response model 3 | Differential | $dY/dt = Kin \cdot (1 + (Emax*C)/(EC50 + C)) - Kout \cdot Y$ |
| Indirect response model 4 | Differential | $dY/dt = Kin - Kout*(1 + (Emax*C)/(EC50 + C)) \cdot Y$ |

Where Y is the observed response, C is the drug concentration, t is time and all other variables are fitted parameters. It may be observed that each of these responses may be modeled as mediated through an "effect compartment". An effect compartment provides a mechanism to describe the commonly observed time delay in drug effects. The concentration (C in the equations) is not the concentration observed in the plasma of blood, but rather the concentration in a hypothetical effect compartment, whose time course is delayed by a linear rate constant compared to the central compartment. The differential equation that describes this is $$\frac{dC_e}{dt} = k \cdot C - k \cdot C_e$$

Where $C_e$ is the hypothetical concentration in the effect compartment, and C is the concentration in the blood or plasma.

Traditional "Model Building"

The literature documents a well-defined process to "build" these models. The conventional process is a very linear process, with one hypothesis tested at a time, and that hypothesis either accepted or rejected, then the next hypothesis tested, as is described by the techniques of forward addition and backwards elimination.[iii] Combinations of features are typically not tested together. This process consists of various plots to examine the raw data, as well as diagnostics (statistical and graphical) to select likely models and covariate relationships to examine. This process is very time consuming and labor intensive, often requiring weeks or months of work from an experienced practitioner.

A traditional approach to model building includes the techniques of forward-addition-backward elimination. This consists of starting with a base model, usually a simple model, and adding features to it, one at a time and testing whether each feature are statistically supportable (usually P<0.05 or P<0.01). This is widely applied to linear regression, logistic regression and forms the basis for the standard model building approach in mixed effects non linear regression. For example, in multiple linear regression, one might start with a base case or no linear effects, that is $$Y = b$$

Then a single linear effect is added:

$$Y=m(1) \cdot x(1)+b$$

Where m(1) is an estimated parameters and x(1) is the first element of the x vector. A formal statistical test is done to determine if this is statistically significant. If it is, this term (feature) remains in the model and another element of x is added:

$$Y=m(1) \cdot x(1)+m(2) \cdot x(2)+b$$

This is forward addition. Another technique is backward elimination. In this method, all candidate features are added in the base model. Each is removed, one at a time and the significance is assessed.

Pharmacokinetic/pharmacodynamic models have traditionally been developed using the forward addition approach, by starting with simple models (e.g., one compartment) and adding features.[iv,v,vi,vii]. For example, a data set would become available that included the data (time, dose, observed concentration) as well as potentially relevant covariates (age, weight, gender, race, renal and liver function). A one compartment model would be fitted to the data. Once this was done, graphics would be created to examine the data for other relationships that might be added to the model. For example, a plot of time vs residual error might be created. This plot would be examined for patterns characteristic of more complex time course of concentration (e.g., two compartment models).

Alternatively, a two compartment model could simply be fitted to the data as well and compared to the results of the one compartment fit. The comparison would be made based on (among other factors) a statistical test known as the log likelihood test. The log likelihood test requires that twice the log likelihood value (a measure of the goodness of fit) change by at least 3.84 unit for each parameter added to the model for the addition of that parameter to be statistically significant at the $P<0.05$ level. The addition of a pharmacokinetic compartment adds two parameters, a rate constant to describe the transfer of drug into the compartment and one to describe the transfer of drug out of the compartment. Therefore, the log likelihood value for a two compartment model must be at least 7.68 units ($2 \cdot 3.84$) less than log likelihood value for the one compartment model. Additional compartments can be tested in the same way. Other features (absorption lag time, for example) can be tested similarly.

In order to apply the log likelihood test the models must be hierarchical. For models to be hierarchical, the smaller, less complex model must be a special case of the larger model. A one compartment model is a special case of a two compartment model, where the rate constants for transfer to and from the second compartment are equal to zero (or infinity). Therefore one and two compartment models are hierarchical. For models that are not hierarchical, other statistics can be used for comparison of models. These criteria include the Akaike information criteria and the Schwartz criteria.[viii,ix]

Covariate relationships can be developed similarly. Graphics can be developed to examine relationships between post hoc estimates of parameters and demographics.[x] Post hoc estimates of parameters are estimates of individual's parameter values, based on Bayesian inference. Examination of these plots may suggest to the modeler that a relationship exists, which can then be incorporated into the model and formally tested. For example, one might find that a plot suggests that the volume of distribution is larger in people who have a greater body weight. This would then be modeled as:

$$Volume=THETA(1)+THETA(2)*Weight$$

Where THETA(1) and THETA(2) are estimated parameters.
Note that this is a hierarchical model in comparison to $$Volume=THETA(1)$$

If the value for THETA(2) is set to 0, the larger model becomes the simpler model. Therefore, the addition of this feature to the model can be tested for statistically significance.

Random effects (interindividual and intraindividual) can also be examined. There are no specific graphics to be examined for random interindividual effects. Typically there are relatively few of these to be tested (one for each basic parameter, e.g., rate constants and volumes). The initial model often includes a log normal inter individual error on each basic parameter. Based on the estimates of these, and how well they are estimated (the standard error of the estimate), they may be eliminated or retained in the model.

One can apply a less rigorous test to the addition of random effects, by comparing the Akaike information criteria to the model. The Akaike information criteria (AIC) is the log likelihood objective function+$2 \cdot$(# of estimated parameters). Each random effect adds one estimated parameter to the model (the variance of the distribution). Therefore, a decrease in the objective function ($-2 \cdot$log likelihood) of 2 when a single random effect is added would lead one to prefer that model. This is not a formal test of hypothesis however.

The literature contains one effort to automate this process.[xi] This work is derived from the technique of plotting post hoc estimates for parameters vs covariate values. Similarly to the current invention, each potential covariate relationship must be explicitly listed. The automated algorithm of Jonsson et al. then examines relationships between post hoc estimates of parameters and covariates. Each potential relationship is examined numerically. The most likely relationship is then incorporated in the next candidate model using the forward addition technique.

Limitations of Current Model Building Approach

Traditional statistical model selection in linear regression is based on backwards elimination. In backwards elimination, all postulated effects are entered into the model and then removed one at a time and tested for significance. This approach is not practical in NONMEM, for several reasons. First, some of the models are mutually exclusive. One may describe the relationship between weight and volume of distribution as linear or log-linear, it cannot be both. So, both effects cannot be in the model at one time. In traditional, linear regression, all effects are simple linear effects, no alternatives are available, and so the effect is either present or not present. Second, non-linear regression is computationally much more difficult than linear regression. Such a large model (with all possible effects) would invariably lead to computational difficulties. As a result of these problems using backwards elimination in NONMEM, forward addition is invariably used. The primary limitation being that it has been shown that the forward addition approach to model building has the potential to miss important interactions between effects, when effects are added one at a time[xii].

SUMMARY OF THE INVENTION

It is the object of the present invention to provide improved methods, systems and computer program products for identifying the optimal or near optimal model of the concentrations or pharmacological effects of a drug or drugs. The central concept is to identify a candidate model search space, then search that space. The candidate model search space will be defined as having n dimensions where a dimension is a mutually exclusive set of model features. The dimensions of the search space have discrete values. For example, a parameter either is (value=1) or is not (value=0) a specific function of a demographic variable (covariate). This dimension has two values, 0 and 1. A value of 1.5 is not possible.

Several methods have been identified to search such an n dimensional discrete space. These include a full grid search, comprising the examination of every possible model in the candidate model space, genetic algorithm, which is a attempt to reproduce the process of evolution, simulated annealing, which is an attempt to reproduce the process of annealing of metals, scatter search/path relinking, neural networks, tabu search and integer programming.

Thus, in one aspect, the invention provides a method, system and computer program product for selecting a near optimal or optimal mathematical model from a set of candidate models, comprising:

a) defining a candidate search space having n dimensions, wherein n is a positive integer and each dimension represents a set of mutually exclusive features from which exactly one of said mutually exclusive features is chosen from each set of mutually exclusive features for each candidate model; and b) searching said space for a near optimal or optimal model by a method selected from the group consisting of: full grid search, simulated annealing, integer programming, scatter search/path relinking, neural networks, tabu search and genetic algorithm.

In another aspect, the invention provides a method, system and computer program product for automated generation of NONMEM/NMTRAN control files, comprising:

a) selecting exactly one feature from each of n sets of candidate features, wherein n is a positive integer; and b) substituting text associated with each selected feature into a control file template.

In still another aspect, the invention provides a method, system and computer program product, for automated evaluation of the optimality of a model comprising:

minimizing an overall objective function, wherein the overall objective function is computed by combining $-2*\log$ likelihood value with a penalty for each parameter estimated, a penalty for each element of the interindividual variance matrix estimated, a penalty for each element of the intraindividual variance matrix estimated, a penalty imposed if the minimization does not conclude successfully, a penalty if the standard errors of the parameter estimates cannot be obtained, a penalty if the correlation matrix of the estimates has any element >0.95 and a "niche" penalty for being similar to other models in the population (within a "niche radius" of other models.

In a further aspect, the invention provides a method, system and computer program product for selecting a near optimal or optimal mathematical model from a set of candidate models, comprising:

a) defining a candidate search space having n dimensions, wherein n is a positive integer and each dimension represents a set of mutually exclusive features from which exactly one of said mutually exclusive features is chosen from each set of mutually exclusive features for each candidate model; and b) selecting an initial set of candidate models by selecting one feature from each set of mutually exusive features by a uniform random process for each candidate model and representing each model by a bit string;

c) computing a goodness of fit (fitness) of each model in terms of the log likelihood using a pharmacokinetic and/or pharmacodynamic model;

d) calculating for each model an overall objective function given by the expression:

fitness+theta penalty·ntheta+random effect penalty·nrand+success·success penalty+covariance·covariance penalty+correlation·correlation penalty, wherein fitness is $-2*\log$ likelihood of the observed data given a pharmacokinetic and/or pharmacodynamic model, theta penalty is the penalty for each fitted parameter, ntheta is the number of parameters, random effect penalty is the penalty for each random effect, nrand is the number of random effects, success is 0 if the minimization was successful and 1 if not, success penalty is the penalty if the minimization is not successful, covariance is 0 if the covariance step was successful and 1 if not, covariance penalty is the penalty if the covariance step is not successful, correlation is 0 if no estimation correlations are >0.95 and 1 if at least one is >0.95 and correlation penalty is the penalty for a correlation >0.95;

e) optionally, scaling the overall objective function of each model to be between and upper limit R and a lower limit S wherein the ratio of R to S is between 2:1 and 100:1;

f) providing a number y of models to be in a subsequent generation;

g) selecting with replacement y number of parents of the said subsequent generation from the current generation, wherein the probability of selection of a model in the current generation is proportional to said fitness or optionally to said scaled fitness;

h) associating said parents into m groups comprising p parents where p is an integer greater than 1;

i) optionally, selecting some fraction of the m groups of parents to undergo at least one cross over;

j) optionally, crossing over said selected fraction at a random location on said bit string to create two new individuals for said subsequent generation;

k) assigning bit strings in current generation that are not selected for cross over to said subsequent generation;

l) optionally, randomly mutating bits of said subsequent generation bit strings wherein said mutation comprises changing a bit value 0 to a bit value of 1 or changing a bit value of 1 to a bit value of 0; and m) repeating the steps of c through l until further decrease in the lowest value of the overall objective function (improvement in maximum fitness) no longer occurs.

Preferably, the initial population is a random population. In one embodiment, fitness is assessed by calculating some statistic of the goodness of fit of the model to the data and adding cost associated with desirable attributes of the model, including parsimony (fewer parameters). Preferably, the goodness of fit of the model to the data is the log likelihood of the data, given the model.

Preferably, the ratio of R to S is between 10:1 and 50:1. In one embodiment, the number of models in the subsequent generation is equal to the number of models in the current generation. In another embodiment, p=2.

Preferably, the fraction to undergo at least one cross over is selected randomly. More preferably, the fraction to undergo at least one cross over is between 0.4 to 1.0

In one embodiment, sets of mutually exclusive features comprise one or more members of the group consisting of:

the number of pharmacokinetic compartments, the presence of non-linear elimination, the presence of non-linear absorption, the presence of interindividual variability on each parameter, the function describing the interindividual variability of each parameter, the function describing the residual variability, the structure of the interindividual covariance matrix, emax pharmacodynamic model, linear pharmacodynamic model, types 1 through 4 indirect response pharmacodynamic model, the presence of an effect compartment, the relationship between drug elimination and age, the relationship between drug elimination and renal function, the relationship between drug elimination and liver function, the relationship between drug elimination and gender, the relationship between drug elimination and weight, the relationship between drug volume of distribution and age, the relationship between drug volume of distribution and gender, the relationship between drug volume of distribution and weight, the relationship between drug volume of distribution and cardiac function, the relationship between drug volume of distribution and renal function, the relationship between drug volume of distribution and liver function, the relationship between drug bioavailability and age, the relationship between drug bioavailability and gender, the relationship between drug bioavailability and weight, the relationship between drug bioavailability and liver function, the relationship between drug bioavailability and renal function.

In yet another aspect, the invention provides a method, system and computer program product for selecting a near optimal or optimal mathematical model from a set of candidate models, comprising:

a) defining a candidate search space having n dimensions, wherein n is a positive integer and each dimension represents a set of mutually exclusive features from which exactly one of said mutually exclusive features is chosen from each set of mutually exclusive features for each candidate model; and b) selecting an initial set of candidate models by selecting one feature from each set of mutually excusive features by a uniform random process for each candidate model and optionally representing each model by a bit string;

c) computing a goodness of fit (fitness) of each model in terms of the log likelihood using a pharmacokinetic and/or pharmacodynamic model;

d) calculating for each model an overall objective function given by the expression:
fitness+theta penalty·ntheta+random effect penalty·nrand+success·success penalty+covariance·covariance penalty+correlation·correlation penalty, wherein fitness is −2*log likelihood of the observed data given a pharmacokinetic and/or pharmacodynamic model, theta penalty is the penalty for each fitted parameter, ntheta is the number of parameters, random effect penalty is the penalty for each random effect, nrand is the number of random effects, success is 0 if the minimization was successful and 1 if not, success penalty is the penalty if the minimization is not successful, covariance is 0 if the covariance step was successful and 1 if not, covariance penalty is the penalty if the covariance step is not successful, correlation is 0 if no estimation correlations are >0.95 and 1 if at least one is >0.95 and correlation penalty is the penalty for a correlation >0.95;

e) searching the candidate search space using simulated annealing, wherein simulated annealing comprises the steps of:

i) randomly selecting one model from the candidate set of models;

ii) selecting an initial value for temperature (T) wherein T represents the tolerance of a minimization process for retaining a model that results in a higher energy; and T is defined as a change in value of the overall objective function;

iii) assessing the energy of the initial model, wherein energy is defined as the value of the overall objective function;

iv) randomly changing the model to generate a subsequent model;

v) assessing the energy of the subsequent model using the methods of steps c) and d) above;

vi) retaining the subsequent model as the current model if the energy is lower than the current model;

vii) if the energy of the subsequent model is higher than the energy of the current model, computing the probability of retaining it as:

$$e^{\Delta E/KT}$$

where T is the temperature, ΔE is the change in energy (current model energy−subsequent model energy), and k is Boltzman's constant; or Otherwise, rejecting the subsequent model;

viii) reducing the value of T;

ix) randomly selecting one model from the candidate set of models; and x) repeating the steps of iv through ix until further reduction in energy (overall objective function) no longer occurs.

In still another aspect, the invention provides a method, system and computer program product for selecting a near optimal or optimal mathematical model from a set of candidate models, comprising:

a) defining a candidate search space having n dimensions, wherein n is a positive integer and each dimension represents a set of mutually exclusive features from which exactly one of said mutually exclusive features is chosen from each set of mutually exclusive features for each candidate model; and b) searching the candidate search space using full grid search wherein full grid comprises the evaluation of every possible model in the search space.

In yet another aspect, the invention provides a method, system and computer program product for selecting a near optimal or optimal mathematical model from a set of candidate models, comprising:

a) defining a candidate search space having n dimensions, wherein n is a positive integer and each dimension represents a set of mutually exclusive features from which exactly one of said mutually exclusive features is chosen from each set of mutually exclusive features for each candidate model; and b) selecting an initial set of candidate models by selecting one feature from each set of mutually excusive features by a uniform random process for each candidate model and optionally representing each model by a bit string;

c) computing a goodness of fit (fitness) of each model in terms of the log likelihood using a pharmacokinetic and/or pharmacodynamic model;

d) calculating for each model an overall objective function given by the expression:
fitness+theta penalty·ntheta+random effect penalty·nrand+success·success penalty+covariance·covariance penalty+correlation·correlation penalty, wherein fitness is −2*log likelihood of the observed data given a pharmacokinetic and/or pharmacodynamic model, theta penalty is the penalty for each fitted parameter, ntheta is the number of parameters, random effect penalty is the penalty for each random effect, nrand is the number of random effects, success is 0 if the minimization was successful and 1 if not, success penalty is the penalty if the minimization is not successful, covariance is 0 if the covariance step was successful and 1 if not, covariance penalty is the penalty if the covariance step is not successful, correlation is 0 if no estimation correlations are >0.95 and 1 if at least one is >0.95 and correlation penalty is the penalty for a correlation >0.95;

e) initializing the search with a call to OCL setup in the OptQuest callable library and initialize a population of models with a call to OCLInitpop;

f) initializing each search dimension with a call to OCLdefinevar in the OptQuest callable library;

g) selecting an initial model from the candidate search space using scatter search/path relinking and tabu search as implemented in the OptQuest Callable library from OptTek systems by calling the function Octretsolution;

h) searching the candidate search space using Scatter search/path relinlking/Tabu search using the OptQuest Callable library wherein Scatter search/path relinking/Tabu search comprises the steps of:

i) evaluating the overall objective function of the current model;

ii) adding the value of the overall objective function of the current model to the OptQuest Callable library database with a call to the function OCL putSolution;

iii) finding the overall objective function of the best model thus far evaluated with a call to the function OCLGetBest in the OptQuest Callable Library;

iv) getting the subsequent model with a call to the function OCLGetSolution; and v) repeating steps i–iv until either the required number of evaluations or convergence is seen; and i) deleting current problem from memory with a call to OCLGoodBye.

The methods, systems and computer program products of the invention are particularly useful for selecting models that represent pharmacokinetics or pharmacodynamics.

BRIEF DESCRIPTION OF THE DRAWINGS

FIG. 4 is a list of the eight possible models that would exist in a three dimensional candidate model search space, where each dimension had two possible values.

FIG. 8 is a program for searching a search space of candidate NONMEM models using genetic algorithms.

DETAILED DESCRIPTION OF THE INVENTION

The present invention and the preferred embodiments are described more fully below. The invention may, however, be embodied in many different forms and should not be construed as limited to the embodiments set forth herein.

As will be appreciated by one of skill in the art, the present invention may be embodied as methods, computer systems and/or computer program products. Thus, the invention may take the form of a hardware embodiment, a software embodiment running on hardware, or a combination thereof. Also, the invention may be embodied as a computer program product on a computer-usable storage medium having computer-usable program coded embodied in the medium. Any suitable computer readable medium may be utilized including disks, CD-ROMs, optical storage devices, magnetic storage devices, and the like.

Computer program code for carrying out operations of the invention may be written in Visual Basic, (Microsoft Corporation, Redmond Wash.) and the like. However, the embodiments of the invention do not depend upon the use of a particular programming language. The program code may be executed on one or more servers or computers.

The invention is described with reference to flowchart illustrations of methods, systems and computer program products. The flowchart illustrations can be implemented by computer program instructions. Such instructions may be provided to a processor of a computer and may also be stored in computer readable memory that can direct a computer to function in a particular manner, such that the instructions stored in the computer-readable memory are an article of manufacture.

The present invention requires a redefinition of the problem in order to automate a very time consuming, labor intensive task. It can be argued that the process of "model building" in pharmacokinetic/pharmacodynamic modeling is in reality "model searching", with a large, but finite number of candidate models being considered in an effort to find the one or ones that best describes the data. Note that none of these models is "correct", that is truly representative of the underlying physiology. The models are simply used to empirically describe the observed data.

Figure 1:
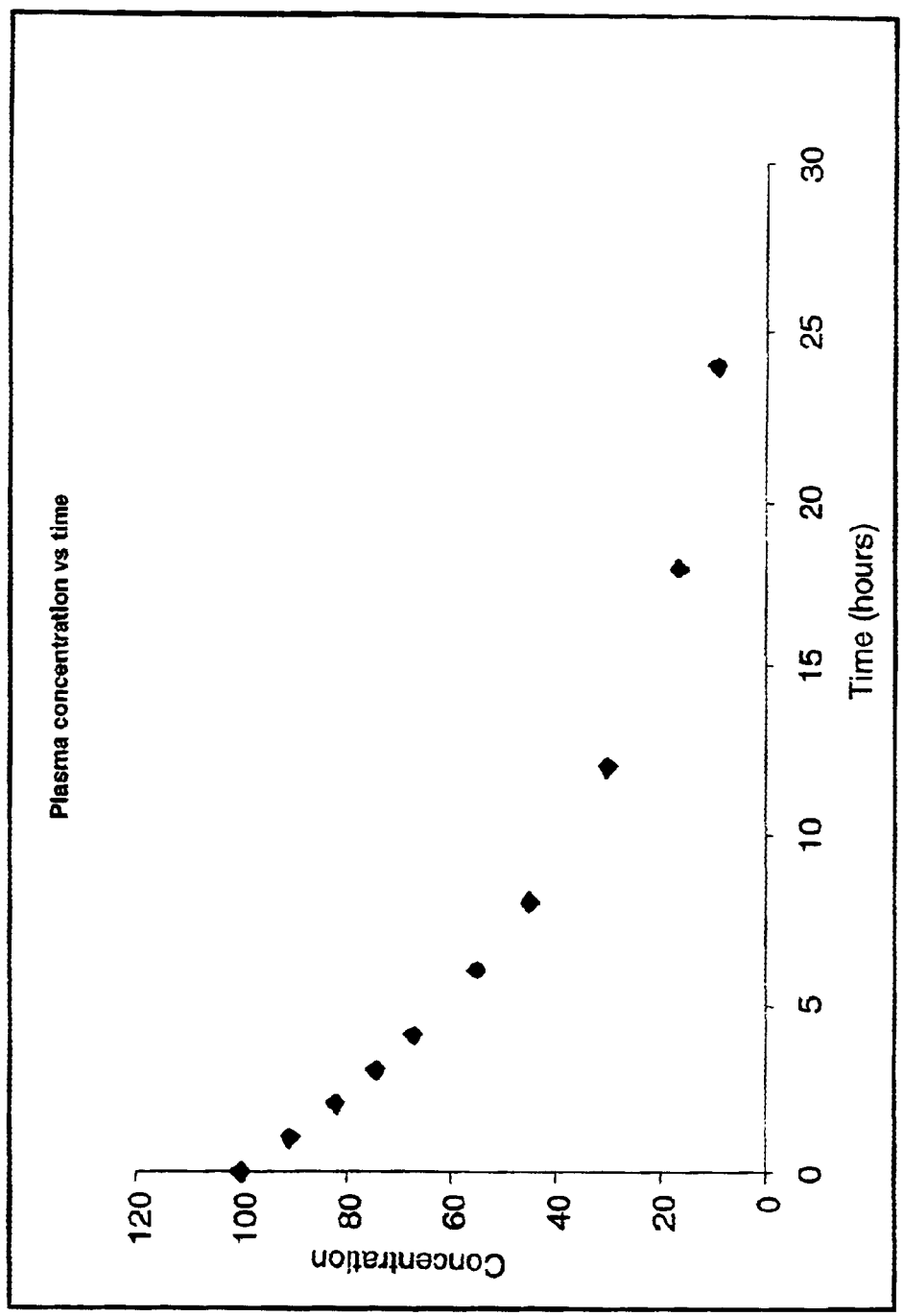
FIG. 1 is a representation of pharmacokinetic data (concentration vs time).
Figure 2:
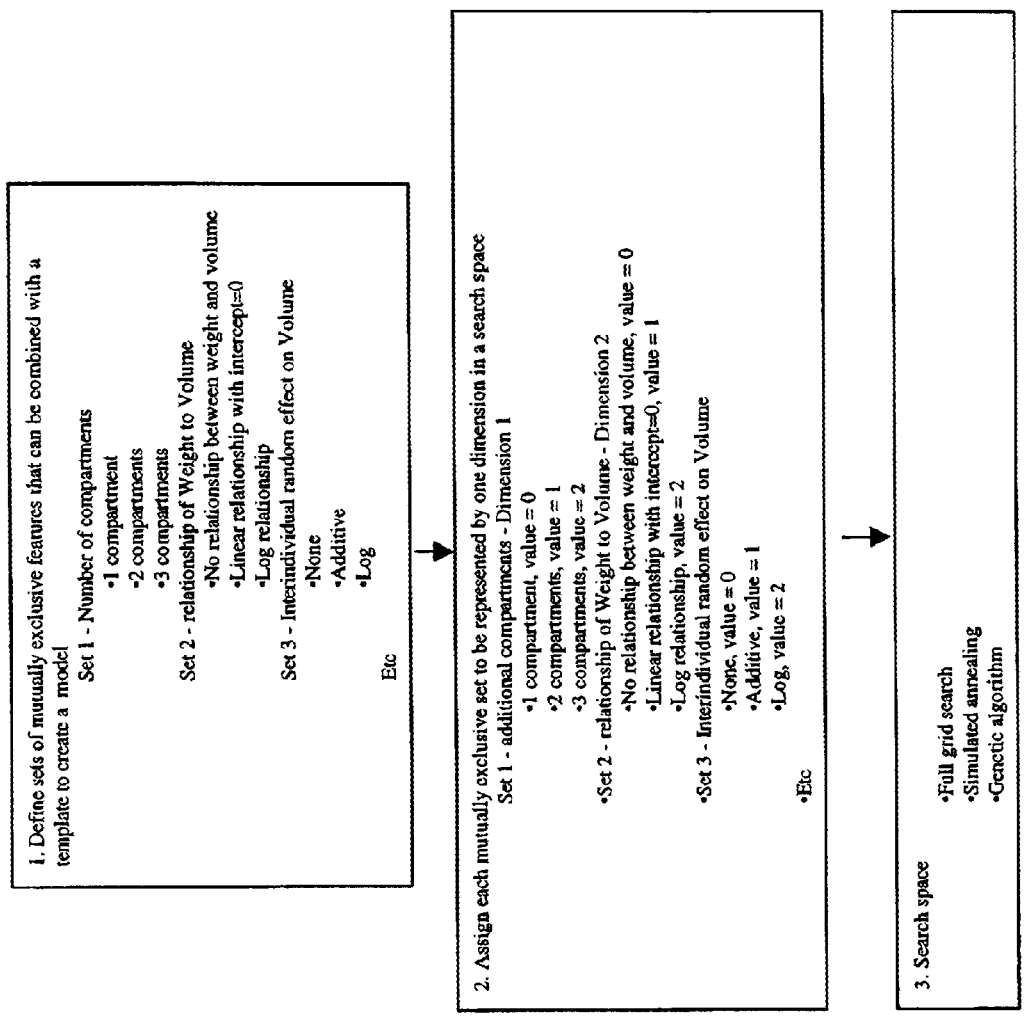
FIG. 2 is a flow chart of the creation of the candidate model search space. N sets of mutual exclusive model features are identified, such as the number of compartments and relationships between parameters of the model and demographic variables. Each set of model features is assigned to exactly one dimension. So, there would a number of compartments dimension. Then each feature within that feature set is assigned a value, resulting in an n dimensional candidate search space. This candidate search space can then be searched.

An important novel aspect of this present invention is to redefine the process of identifying the optimal or near optimal model as a search of a candidate model search space rather than model building. FIG. 2 describes the process of creating that search space. First, a set of model feature sets is identified. The user might be interested in including the number of pharmacokinetic compartments in the search. If so, a dimension of the search space would be defined for that feature set. Possible values in this feature set include one compartment, two compartments and three compartments. Any given model will have exactly one of these values, it cannot be both one compartment and two compartment.

Figure 3:
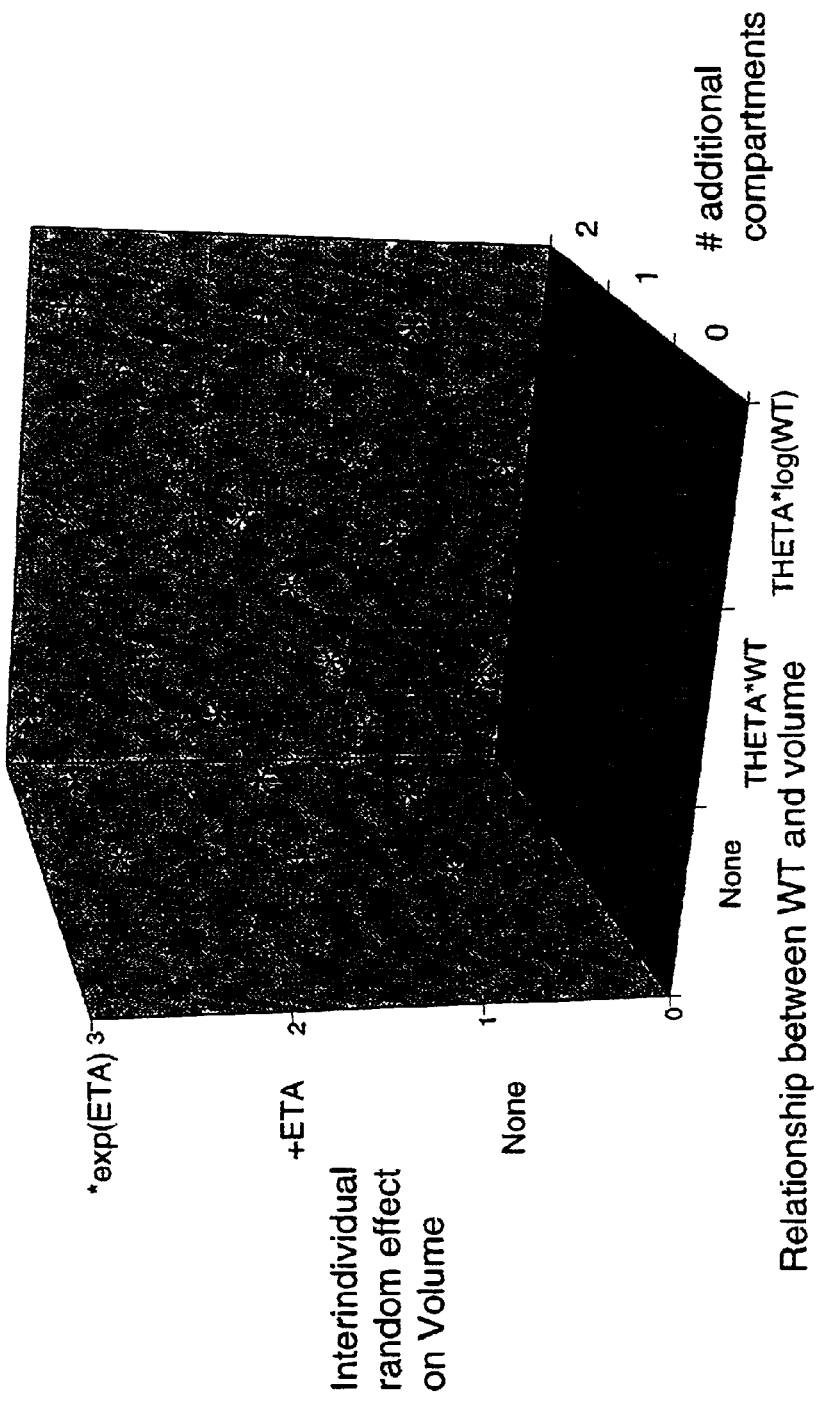
FIG. 3 is a depiction of the 3 dimensional candidate search space described in FIG. 2, with the 27 possible models identified.

FIG. 3 is a depiction of a simple three dimensional search space, with 27 possible models. All possible combinations of each of the 3 candidate features in each of 3 dimensions define the 27 possible models ($3^3$). FIG. 4 shows all possible combinations for a simpler, three dimensional search space, with each dimension having only two possible values (0,1). This large, but finite set of candidate models could in theory be examined exhaustively (a full grid search). The grid search would proceed over each dimension of mutually exclusive candidate model features. That is, each model could be fitted to the observed data, and well-defined statistical tests applied to select the model that is "best". In reality, the number of potential models is frequently very large. If one fits only a two compartment model, with five parameters (Ka, volume of distribution, K32, K23 and lag time), and fits each of 6 potential covariates (age, weight, gender, race, renal function, liver function) to each using only a single relationship of the covariate to the parameter, one has $2^{30}=1.07E9$ combinations.

Note that the set of potential models can be described as a multi dimensional space. The number of compartments (1, 2, 3, 4) is mutually exclusive and defines one dimension. This dimension has four strictly discrete (i.e., not ordered discrete) values, 1, 2, 3 and 4. Another dimension is whether volume of compartment 1 is related to weight, and how. This dimension might have three possible values, specifically:

| Value | Relationship to weight |
|---|---|
| 1 | *1 (no relationship) |
| 2 | +Θ*weight |
| 3 | $e^{(Θ*weight)}$ |

Where Θ is a parameter of the model.

The candidate relationships between weight and volume define another dimension of the candidate search space. Analogous discrete values can be listed for other dimensions, and models.

Representation of the Variance Covariance Matrix as an n Dimensional Space

The variance-covariance matrix describes the inter subject (between people) variation of the parameters. If this matrix is diagonal (i.e., all off diagonal elements are set to 0), then the diagonal elements are simply the inter subject variance. If the matrix is not diagonal, then the off diagonal elements are the covariances between the subjects values. In NONMEM, the inter subject variability may permit covariances between specific parameters and not others. Thus, if volume and clearance were to be permitted to covary, but neither would be permitted to covary with KA the variance covariance matrix would be represented as:

|  | Volume | Clearance | Ka |
|---|---|---|---|
| Volume | X | X | 0 |
| Clearance | X | X | 0 |
| Ka | 0 | 0 | X |

Where X is an element that may vary (and is estimated by NONMEM), and 0 is an element fixed to 0. In the NONMEM code this would be represented with the code:

```
$OMEGA    BLOCK(2)
0.3
0.01 0.3
$OMEGA
0.3
```

This approach is general (i.e., permitting any elements to covary with any other, and have zero covariance with any other) only if the sequence of the ETAs in the code can be changed. In the above example, it is assume that Volume is associated with ETA(1), Clearance with ETA(2) and Ka with ETA(3). For this sequence and associations, it would not be possible to permit KA to covary with Volume, but not with Clearance. For that combination of covariances, it would be necessary to resequence the ETA's as Volume associated with ETA(1), Ka associated with ETA(2) and Clearance associated with ETA(3). Thus, for a completely general solution, it is most convenient to represent both the structure of the matrix, and the sequence of the ETAs in the NONMEM code.

The structure of the matrix can be represented as follows. For a matrix of dimension n (for n ETAs) n−1 bits are defined. Each i bit (i=1 to n−1) determines whether the i+1 row of the matrix is composed entirely of 0's (except the diagonal element) or if it is included in a non-diagonal matrix above it. For example, assume n=3. This will require n−1=2 bits. The matrix is represented below:

A
B C
D D E

A, C and E are required to be non-zero. If the first bit (i=1) is 1 then B (row i+1) is non zero, and estimated. If the first bit is 0 (i=0) then B is fixed as 0. If the second bit is (i=2) is 1 then the third row (the 2 D's) is non-zero and estimated. If the second bit is 0, then the values for D are fixed to zero. The four possible combinations are given below:

| (0, 0) | | | (1, 0) | | |
|---|---|---|---|---|---|
| A | | | A | | |
| 0 | C | | B | C | |
| 0 | 0 | E | 0 | 0 | E |
| (0, 1) | | | (1, 1) | (full matrix) | |
| A | | | A | | |
| 0 | C | | B | C | |
| 0 | D | E | D | D | E |

Each bit in this bit string (length=2 in this example) is a dimension of the candidate model space.

Second, the sequence of ETA's in the model is defined. For n ETA's there are n! possible sequences. The first ETA in the model will have n possible values, the second n−1 etc. In the genetic algorithm implementation, this will require n−1 "genes". The first will have n possible values, the second n−1 etc.

The integer describing the ETA in each position, except the last, which is fixed is a dimension in the candidate model search space Application of Genetic Algorithm to Pharmacokinetic/Pharmacodynamic Model Building in NONMEM According to Goldberg "Genetic algorithms are search algorithms based on the mechanics of natural selection and natural genetics".[1] Genetic algorithm is chosen over the other methods for a demonstration of this invention for a number of reasons. Traditional optimization techniques are limited to continuous parameters, that is, the parameters can take any value. The descriptions of a model however, is discrete, either a feature is present in a model or it isn't, and the model may be one compartment or two compartments, but not 1.5 compartments. There are seven methods for optimization of discrete systems. These are:

Exhaustive search
Genetic algorithm
Simulated annealing
Scatter search/path relinking[xiv]
Neural Networks
Tabu search[xv]
Integer programming[xvi]

While neural networks can be applied to discrete system, they are better suited to continuous systems. Integer programming is best applied to system of ordered categorical variables. That is, parameters that take values where each can be described as more or less than the others (i.e., 1, 2, 3 or small, medium, large). The same is true for Tabu search[xvii]. This does not apply to this model selection process, except for the number or compartments. An expression for volume of distribution as a linear function of weight is not greater or less than one with volume described as a linear function of age. Simulated annealing is a search algorithm based on the mathematics of the annealing of metals with slow cooling, and is likely well suited to this approach.[xviii] A feature of genetic algorithm called epistasis is likely to be more efficient than simulated annealing. Epistasis is the property that features in the genetic algorithm tend to form groups that are preserved in the process. For example, the optimal combination of genes for the clearance may "evolve" in one set of individuals, while the optimal combination for volume of distribution may evolve in another. These features, described by a series of loci, tend to be preserved, as crossing over is less likely to occur in loci that are close to each other. This will be described in more detail later.

Figure 5:
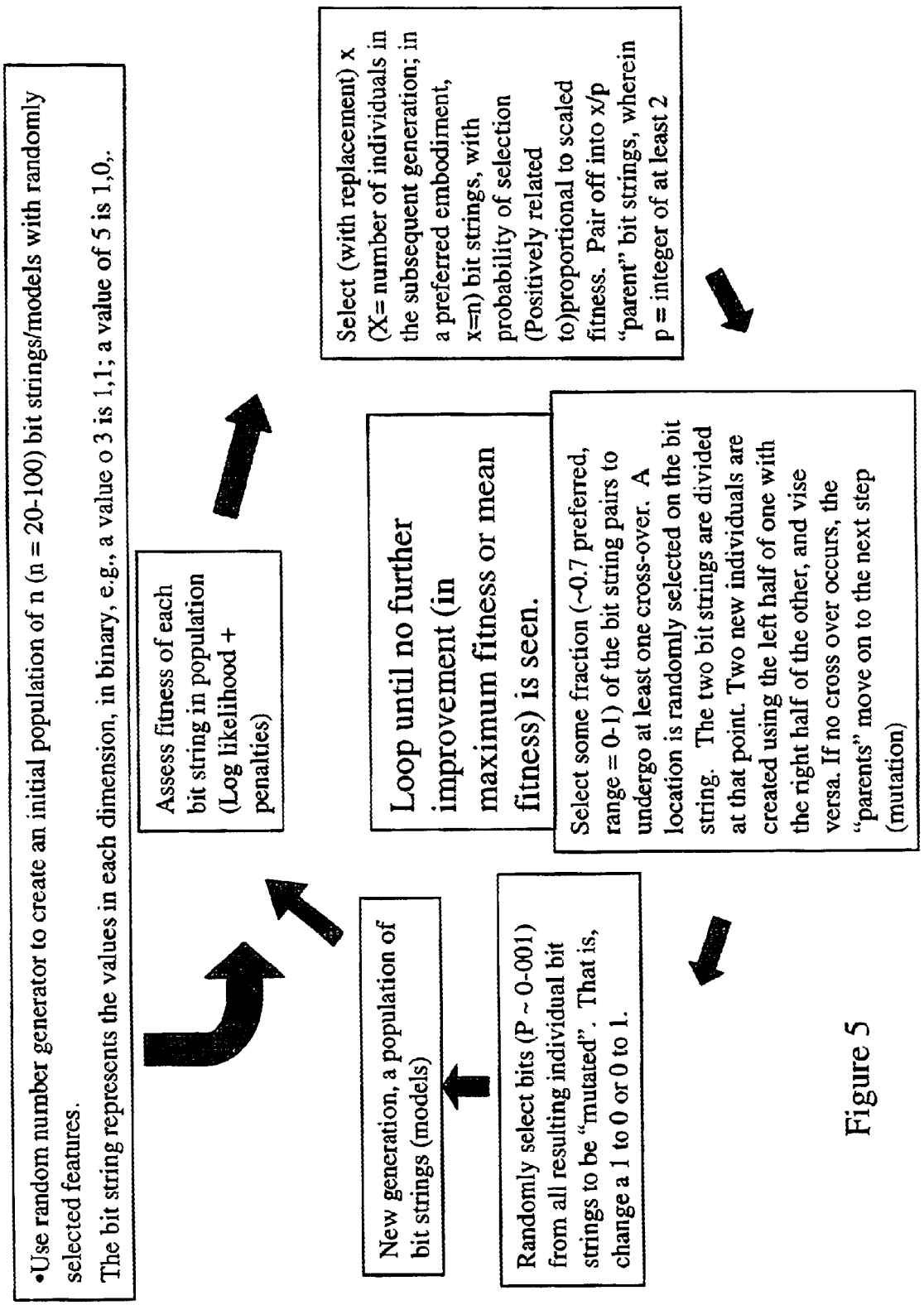
FIG. 5 is a flow chart of the process of genetic algorithm.

FIG. 5 is a flow chart of the overall process of searching the candidate model search space using genetic algorithm. The most convenient way to implement genetic algorithm, is to describe the system (the model in this case) as a string of discrete variables. Typically, these variables are Boolean (0 or 1). This is a deviation from true genetic evolution, which has variables with four possible values (A, C, T, G). If a feature of the model can have only two values (e.g, volume as a linear function of weight, or unrelated to weight), only one loci is required. If the feature can have 3 or 4 values (i.e., volume as a linear function of weight, volume as a log function of weight), 2 loci will be needed. These variables (loci) are formed into a "gene" which describes the feature. The genes are then formed into a single string. An example is given below:

| Feature | Gene Values | Description | Code describing relationship |
|---|---|---|---|
| Relationship of renal function to clearance. (2 candidate models) | 0 | No relationship | Clearance = THETA(1) |
| | 1 | Linear in renal function | Clearance = THETA(1) + THETA(2) · Renal function |
| Relationship of weight to volume (4 candidate models) | (0,0) | No relationship | Volume = THETA(1) |
| | (0,1) | Linear in weight | Volume = THETA(1) + THETA(2) · Weight |
| | (1,0) | Linear in weight, intercept 0 | Volume = THETA(1) · Weight |
| | (1,1) | Log linear in weight | Volume = THETA(1) + THETA(2) · Log(Weight) |

In this scenario, a model with Clearance as a function of renal function, and volume as a linear function of weight (slope and intercept) would be represented by the string (1,0,1).

To initiate the process, a population of models (individuals in a population) is created, usually by a random number generator. This population may consist of perhaps 30 individuals. The fitness of each model in population is assessed. This requires the uncoding of each genome (string) into a syntactically correct NONMEM model. The parameters for that set of equations (the model) are then estimated using NONMEM (referred to as "fitting the model to the data"), and the goodness of the fit, as well as other factors used to calculate the "fitness" of that individual.

The objective function in NONMEM is a measure of the goodness of fit. This number is equal to −2 times the log likelihood of the observed data, given the model. In addition to the objective function value, which describes the goodness of the fit of the model to the data, parsimonious model are generally preferred, that is, we would like the simplest model that describes the data well. Therefore, a cost (or penalty) is typically applied for each parameter that is fitted in the model. The user may assign this value, but a commonly used value is 7.84, based on the log likelihood test. Random effects in the model are typically addressed in conventional model building. The parameters for one person will vary from those of another person. For example, a parameter might be weight. Typically, weight can be directly measured, but assume for a moment that we are trying to estimate as a parameter of a model. Weight will vary from one person to another, with some population mean and standard deviation. The mean and standard deviation of this distribution is a random effect model. Further, the shape of the distribution is specified in the model. Shapes of distributions include normal (Gaussian), log-normal, beta etc. These again, are discrete features that might be included in the models. The Akaike information criterion suggests that a value of 2 may be appropriate for each random effect entered into the model.

In addition there are several other desirable attributes of a model fit. First, that the minimization conclude successfully. That is, the requested number of significant digits is obtained. Second, that the covariance step be executed successfully, so that standard errors of the estimate can be obtained. Finally, the estimation correlations between parameters are all less than 0.95. The user of the algorithm can enter value for the penalty for these. For an adequate model, all these attributes are typically required to be present. Therefore, a large penalty for each of these (~400) will typically be used.

The calculation of the overall objective function is:

Overall objective function=fitness+theta penalty·ntheta+random effect penalty·nrand+success·success penalty+covariance·covariance penalty+correlation·correlation penalty, wherein fitness is −2*log likelihood of the observed data given a pharmacokinetic and/or pharmacodynamic model, theta penalty is the penalty for each fitted parameter, ntheta is the number of parameters, random effect penalty is the penalty for each random effect, nrand is the number of random effects, success is 0 if the minimization was successful and 1 if not, success penalty is the penalty if the minimization is not successful, covariance is 0 if the covariance step was successful and 1 if not, covariance penalty is the penalty if the covariance step is not successful, correlation is 0 if no estimation correlations are >0.95 and 1 if at least one is >0.95 and correlation penalty is the penalty for a correlation >0.95.

Additionally, provision should be made if numerical errors occur, and none of these values are available. In this case, a value slightly lower than any of the models that did not have numerical error is used. Other penalties could be added to this fitness measure, such as the estimated value of a parameter must be more than twice the value of the standard error of the estimate from some null value if the p value is to be <0.05.

Next, it has been found to be useful to apply a technique called "niching" to the search. Niching adds a penalty to the fitness for the distance of an individual from its neighbors in the search space. The biological analogy is that a given area of a forest has limited resource (either in geography or in a specific resource). As such, when individuals are closer together, there is less for each of them. Practically, in genetic algorithm, this helps maintain adequate diversity in the population, so that all individuals don't "bunch up" together and prematurely converge.

A niching penalty can be calculated in a variety of ways, such as fitness sharing and implicit sharing[2]. In this application, we have chosen a novel method. In method, the user defines the number of niches to be defined in the population, and the niche radius. (niche radius is simply the number of loci that the two individuals differ at). The most fit individual is then selected. All individuals within 1 niche radius of that individual are considered to be in that niche. The next most fit individual, not currently in a niche is then selected, and the next most fit niche is defined as those individuals within one niche radius of that individual. This process is repeated for the number of user defined niches. Those individuals not selected are considered not to be in a niche. Then a user defined "niche penalty" is added to each individual not in a niche. Typically, this niche penalty will be a fraction (perhaps 80%) of the difference between the most fit individual in the niche and the most fit individual that is not in a niche. This niche penalty is then divided between all the members of a given niche.

For example, if a niche penalty of 100 were chosen, each individual not in a niche would have 100 added to their fitness. If there were 4 individuals in the first niche, then 25 (100/4) would be added to each of their fitnesses.

When the overall objective functions are calculated, it is often helpful, if they are scaled. The upper and lower limits of the scaled overall objective functions are defined by the user. Common values are 3 (for upper) and 0.2 (for lower). This is done to improve the numerical stability of the model. In this application, linear regression is performed between the points (mean of overall objective function−2 sd of overall objective function, lower limit of overall objective function) and (mean of overall objective function+2 sd of overall objective function, upper limit of overall objective function)

and the unscaled overall objective function values linearly transformed by this linear relationship. Value greater than or less than the mean +/−2 standard deviations are assigned the upper or lower limit of overall objective function, respectively. The scaling process prevents very large or very small values of overall objective function from driving the selection.

From these scaled overall objective function values, a new generation of individuals (models) is created. Note that, contrary to the usual definition of fitness in genetic algorithm, a lower value is better in this application (lower value for −2 log likelihood corresponds to a higher likelihood of the data, given the parameters). In the scaling process, this relationship is reversed, so that a more fit individual is assigned a higher fitness, and therefore a higher probability of entering into the next generation gene pool. Individuals from the old generation are randomly selected, with replacement to enter into the next generation gene pool. The probability of selection is proportional to the scaled fitness.

The individuals are then paired off. A probability of crossing over is defined by the user (typically about 0.8). A random number is generated, to determine if this pair undergoes cross-over. If so, a position in the genome string is randomly selected, and the two strings are "crossed over". For example, if string 1 is (0,1,0,1,0,1) and string 2 is (0,0,0,1,1,1), and the position selected for cross over is three, the left three bit values from string 1 (0,1,0) is exchanged with the left 3 bit values from string 2 (0,0,0). The two new strings formed are (0,1,0,1,1,1) and (0,0,0,1,0,1). If no cross over is done, the two selected strings are simply copied to the next generation. This process of selecting individuals (with replacement), pairing the off and crossing over is repeated until the next generation has the same number of individuals.

Next, mutations are introduced into the genome strings. The probability of mutation is defined by the user, typically between 0.01 and 0.001. The strings are looped over, a random number between 0 and 1 is generated for each loci on each string. If the value of the random number is less than the probability of mutation, the value at that locus is reversed (1 changed to 0, 0 changed to 1). Finally, a more large-scale change in the genome can be introduced by a frame shift mutation. A frame shift mutation consists of moving the values of all loci in a sub string of the genome one loci left or right. Given that this dramatically changes the resulting model, the probability of it occurring is typically very low (0.01). If an individual is (randomly) selected two loci in that string are randomly selected. The values between those loci are shifted left to right or right to left, depending on whether the first or second loci is to the left.

In a deviation from the natural system, the best individual from the population can be assured of being retained in the subsequent population. This prevents the loss of the best genome, (which would typically be lost if the crossover frequency is greater than 0.5), and improves convergence of the process.

This completes the creation of the next generation of models. This process is repeated until further decrease in the lowest value of the overall objective function (improvement in maximum fitness) no longer occurs. Performance of the process can be improved if a record is kept of each model (the bit string), and if that model is generated again, the NONMEM run is not done, the output from the previous run of the same model is copied onto the current model. Near the end of the search process, the same model will appear many times. Not re-running the NONMEM model can save considerable time.

Creation of NMTRAN Model/Control File

To implement any of the search algorithm and automated method for creating the code and evaluating the resulting output if required. The model in NONMEM is specified by a text file called the NMTRAN control file. In this application, the NMTRAN control file is generated in an automated way from three components. The overall structure of the model is given by the GA control file template. The GA control file template is based on the syntax used for a NMTRAN control file. NMTRAN[xx] is a software application that provides an interface to NONMEM. NONMEM[xxi] provides the capability for non linear mixed effect modeling. The NMTRAN control file is a text file that is translated into Fortran code, providing a set of subroutines required by NONMEM. An example of the GA control file template is given below,

```
$PROB test
$SUBS ADVAN2
$INPUT ID DATE=DROP TIME AMT DV EVID CR AGE GEN RC HT WT BSA TRT
;TRT = 1 – form 1
;TRT = 0 – form 2
$DATA c:>a est÷ata2.prn IGNORE=#
$PK
CRC1 = (140–AGE)*WT/(0.81*CR)*(1–0.15*(1–GEN))
CRCLH = CRC1*60/1000
KA = 1.42*(1–TRT)+0.79*TRT
;CRCLH IS CCLH (CRCL IN H) EFFECT ON TVCL
TVCL1 = THETA(1) CRCL(1) AGCL(1)
TVCL2 = TVCL1 GNCL(1) RCCL(1)
TVCL = TVCL1 WTCL(1) TRCL(1)
CL = TVCL CLER(1)
S21 = THETA(2) AGS2(1) GNS2(1)
S22 = S21 RCS2(1) WTS2(1)
TVS2 = S22 BSS2(1) TRS2(1)
S2 = TVS2 S2ER(1)
K = CL/S2
F1 = TRT +(1–TRT)*0.694
;drug form is 69.4% of drug form 2
$ERROR
IPRD = F
Y = IPRD ERR(1)
$THETA
(0,1) ; BASELINE CL
(0,1); BASELINE S
CRCL(2)
AGCL(2)
GNCL(2)
RCCL(2)
WTCL(2)
TRCL(2)
AGS2(2)
GNS2(2)
RCS2(2)
WTS2(2)
BSS2(2)
TRS2(2)
$OMEGA
CLER(2)
S2ER(2)
$SIGMA
ERR(2)
$EST METHOD = 0 MAXEVAL = 9999 SIG = 3
$COV
```

The features of the model that are dependent on the genome string are described by the variables with parentheses (e.g., CRCL( ), AGCL( ), but not THETA( ), ETA( ) or EPS( ), which have special meaning in NONMEM). For example, CRCL( ) represents possible values for the relationship between creatinine clearance (a measure of renal function) and drug clearance. The structure of the NMTRAN control file requires that these values include a number of tokens. For example, if the model for CRCL effect includes one THETA then an initial estimate/upper and lower bounds for that THETA is usually given. So, two text strings must be inserted, one for CRCL(1), the second for CRCL(2). If the model requires two THETAs, initial estimates for two THETAs must be provided. The text string (or tokens) for CRCL(1) might be: Note, text after a ";" is a comment in NONMEM.

|  | Text to be substituted into control file template |
|---|---|
| First value for CRCL(1) | *1; NO EFFECT |
| Second value for CRCL(1) | +THETA(1) * CRCLH |

Where CRCLH is the creatinine clearance, in liters/hour

And the corresponding CRCL(2) text string (tokens) would be

|  | Text to be substituted into control file template |
|---|---|
| First value for CRCL(2) | ; no THETA NEEDED FOR VALUE OF 1 |
| Second value for CRCL(2) | (0,1); initial estimate for THETA(1) |

It is a syntactic error in the NONMEM control file to combine the first text string for CRCL(1) with the second text string for CRCL(2). Further, since a variable number of THETAs may be used, the number can be assigned to those THETAs only after the values for each are known.

Therefore, in the actual tokens, the THETAs are assigned only sequential letters. After the genome is known, the number of THETAs used in the existing code is determined, and sequential THETA values assigned to the letters.

In the application, an arbitrary number of tokens can be in a token set and an arbitrary number of token sets in a token group. Typically two tokens are required in a token set, but occasionally more are needed.

Thus the token set is comprised of a three level hierarchy. Token groups correspond to the prefix describing the feature, e.g., creatinine clearance relationship to drug clearance—CRCL. The token groups correspond to genes. Within each token group are token sets. A token set is a collection of text strings. The first string is substituted into the control file for the string prefix(1), where "prefix" is the token group prefix (e.g., CRCL), and the second string of the token set is substituted for prefix(2) etc. Each token set corresponds to a specific value of the gene. The number of token sets determines the number of bits in that gene. That is, if there are only two token sets, (only two possible values for that feature), only one bit is needed (0 or 1). If there are three values for that feature, there will be three token sets, and two bits will be needed. This results in some redundancy in the genetic code. That is, (0,1) and (1,0) may represent the same values for the gene. This is addressed by mapping the values of the genes to more than one value of the binary string if needed.

Finally, the individual tokens, consisting of the actual text strings that are substituted into the GA control file resulting in a syntactically correct NONMEM control file. The log of previously run models is checked to see if this model corresponding to this bit string has already been run. If the model has already been run, the previous run results are copied to the current run. If it has not previously been run, the NONMEM control is then processed (by NMTRAN) into the required NONMEM files. NONMEM is then executed and the results examined.

It will also be necessary to implement an automated method for calculating the optimality of a given model. In the present invention, this is done by altering the NONMEM code to output all of the relevant parameters (objective function value, number of THETAs number of elements of OMEGA that are estimated, number of elements of SIGMA that are estimated, whether the minimization was successful, whether the covariance step was successful, and the correlation matrix of the estimates) to a text file. These values are then read in, and the calculation (objective function value+ penalty for each theta+penalty for each element of omega and sigma+penalty if minimization was not successful+ penalty if covariance was not successful+penalty if correlation in correlation matrix of estimate>0.95) is performed.

Results

The initial test run consisted of a one compartment model, with first order absorption. The structure of the model was well known from extensive previous work. The feature sets (and feature values) to be tested included:
1. The relationship of creatinine clearance to clearance (no effect, linear model with slope and intercept).
2. The relationship of age to clearance (no effect, linear with slope and intercept).
3. The relationship of gender to clearance (no effect, effect).
4. The relationship of age to clearance (no effect, effect).
5. The relationship of weight to clearance (no effect, linear with slope and intercept).
6. The relationship of treatment to clearance (no effect, linear with slope and intercept).
7. Intersubject variability in clearance (no variability, additive error, log normal error).
8. The relationship of age effect to Volume of distribution (no effect, linear with slope and intercept).
9. The relationship of gender to Volume of distribution (no effect, effect).
10. The relationship of race to Volume of distribution (no effect, effect).
11. The relationship of weight to Volume of distribution (no effect, linear with slope and intercept).
12. The relationship of body surface area to Volume of distribution (no effect, linear with slope and intercept).
13. The relationship of treatment to Volume of distribution (no effect, linear with slope and intercept).
14. Intersubject variability in Volume of distribution1 (no variability, additive error, log normal error).
15. Residual error (additive, log normal, combined additive and log normal).

This therefore was a 15 dimensional space (n=15) to be searched. For this model building, the following options were used:

| | |
|---|---|
| Cross over frequency | 0.9 |
| Mutation rate | 0.001 |
| Frame shift probability | 0.0 |
| Penalty for each THETA | 7.84 |
| Penalty for each random effect | 3 |
| Penalty for failing covariance | 200 |
| Penalty for estimation correlation > 0.95 | 100 |
| Penalty for no successful minimization | 200 |
| Upper limit of scaled fitness | 3 |
| Lower limit of scaled fitness | 0.2 |

Figure 6:
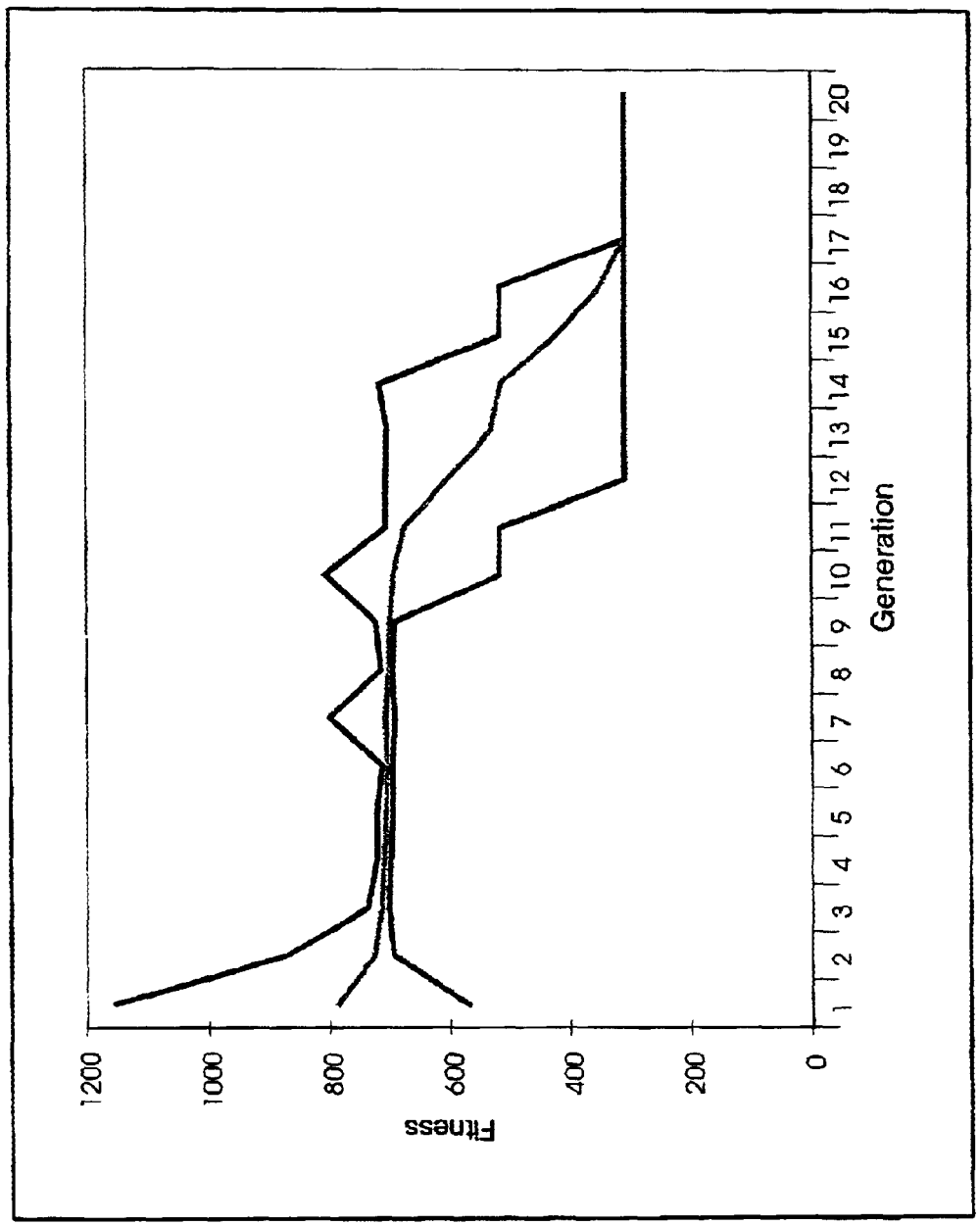
FIG. 6 shows the progress of an optimization search.

This model was allowed to run for 20 generations, with 20 individuals (models) in each generation. FIG. 6 is a plot of the results. The horizontal axis is the generation, the vertical axis is the unscaled fitness. The uppermost line is the maximum value of fitness for any individual in the population, the middle line is the mean fitness and the lower line is the lowest value of fitness. Note that the entire population converges on a minimal value (best fit) for fitness in 17 generations, and that the minimal value model (individual) first appears in 12 generations.

This model suggested that clearance was indeed a function of creatinine clearance (CRCLH, as previous work has indicated), and treatment (TRT). Intersubject variability in clearance is described by a log normal error. Volume of distribution (S2) is a function of age, gender and treatment. Intersubect variability was not supported by the model. Residual variability was best explained by a log normal error as well. The final NONMEM control file, generated by the software, is given below.

---

$PROB test
$SUBS ADVAN2
$INPUT ID DATE=DROP TIME AMT DV EVID CR AGE GEN RC HT WT BSA TRT

```
-continued
;TRT = 1 - form 1
;TRT = 0 - form 2
$DATA c:>a est÷ata2.prn IGNORE =#
$PK
CRC1 =(140-AGE)*WT/(0.81*CR)*(1-0.15*(1-GEN))
CRCLH = CRC1*60/1000
KA = 1.42*(1-TRT)+0.79*TRT
;CRCLH IS CCLH (CRCL IN H) EFFECT ON TVCL
TVCL1 = THETA(1) +(THETA(3)*CRCLH) *1
TVCL2 = TVCL1 *1 *1
TVCL = TVCL1 *1 *EXP(THETA(4)*TRT)
CL = TVCL *EXP(ETA(1))
S21 = THETA(2) *EXP(THETA(5)*(AGE-40)) *EXP(THETA(6)*GEN)
S22 = S21 *1 *1
TVS2 = S22 *1 *EXP(THETA(7)*TRT)
S2 = TVS2 *1
K = CL/S2
F1 = TRT +(1-TRT)*0.694
;drug form is 69.4% of drug form 2
$ERROR
IPRD = F
Y = IPRD *EXP(EPS(1))
$THETA
(0,1) ; BASELINE CL
(0,1); BASELINE S
(0,0.1,5); CRCLH EFFECT ON CL;{$THETA(3)=
;AGE ON CL NO EFFECT
;NO EFFECT OF GENDER
;NOEFFECT OF RACE ON CL
;NO EFFECT OF WT ON CL
(-1,0.01,1);{$THETA(4)=
(-1,0.01,1);{$THETA(5)=
(-1,0.01,1);{$THETA(6)=
;NO EFFECT OF RACE ON S2
;NO EFFECT OF WT ON S2
;NO EFFECT OF BSA ON S2
(-1,0.01,1);{$THETA(7)=
$OMEGA
(0.2);{$ETA(1)=
;NO ETA ON S2
$SIGMA
(0.1);{$EPS(1)=
$EST METHOD = 0 MAXEVAL = 9999 SIG = 3
$COV
```

Figure 7:
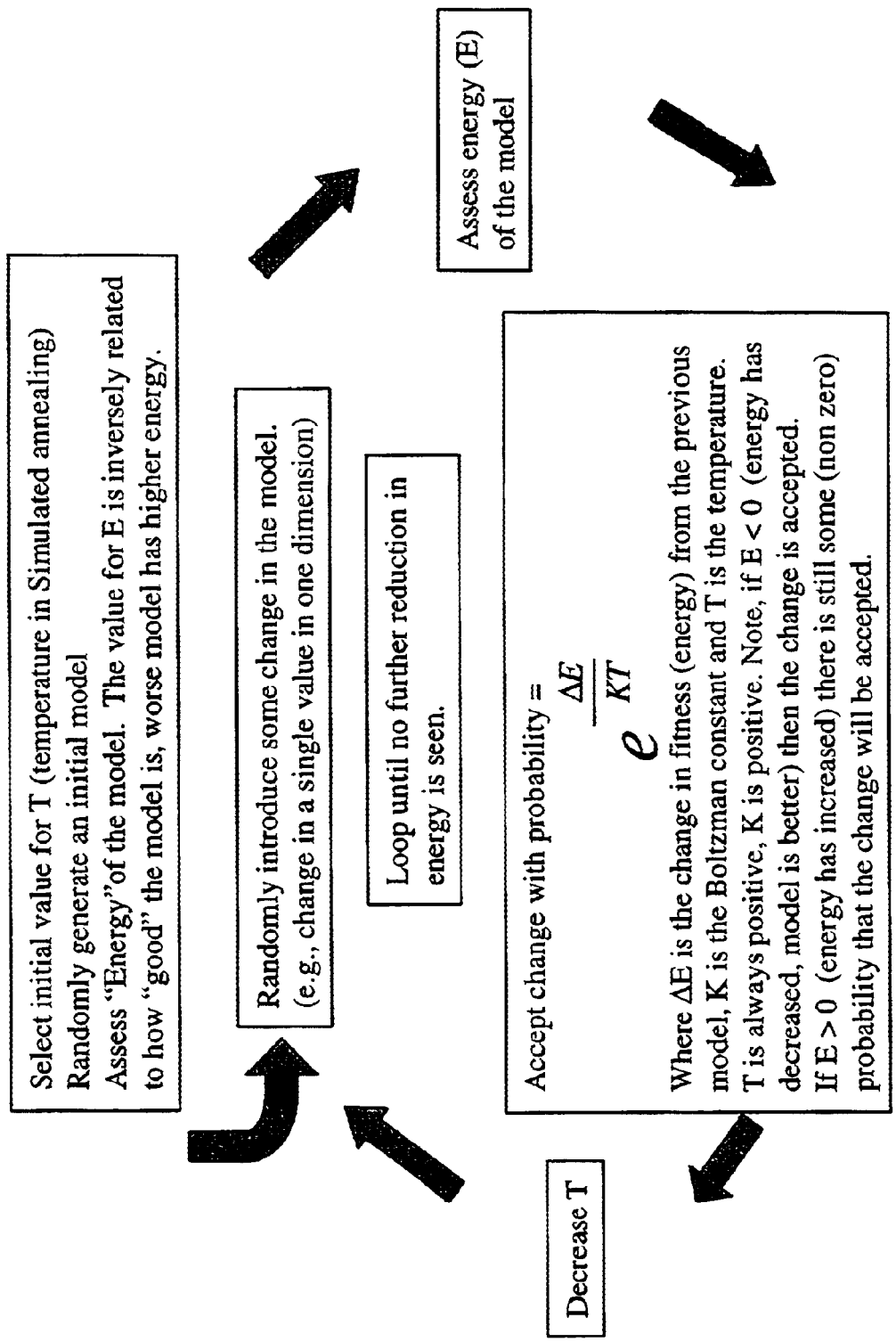
FIG. 7 is a flow chart of the process of simulated annealing.

Application of Simulated Annealing to Searching the Candidate Model Search Space Simulated annealing is an attempt to mathematically reproduce another natural optimization process. The overall iterative process of simulated annealing is depicted in FIG. 7. Simulated Annealing attempt to reproduce the process of the slow cooling of a metal that results in a crystal structure with low energy state. Atoms of a metal are constantly moving. The amount of movement increases as temperature increases. At a high temperature (near the melting point) the atoms are moving sufficiently that no crystal structure can exist. When a metal is cooled quickly from a high temperature (e.g., by plunging into water) the atoms are suddenly "frozen" in that non-crystal, amorphous condition. When a metal is cooled slowly the atoms gradually slow down, and are able the find the lower energy state (the crystal structure) and have some probability of remaining there as the temperature falls.

An analogy is the shaking of a box containing irregular shapes. If the box is shaken vigorously then the shaking stops, the shapes are likely to be very randomly arranged, with a high energy. However, if the box is initially shaken vigorously, the slowly the vigor of the shaking is reduced, the shapes will tend to arrange themselves in a low energy state—they will "settle", in a structure that is relatively low (lower having less potential energy).

This is applied to the search for an optimal model as follows: An initial random model is created. An initial high temperature is defined. The "energy" is calculated. The energy in simulated annealing is same as the overall objective function in genetic algorithm. We want to minimize the overall objective function (the energy) and maximize the fitness. The temperature is defined as change in the overall objective function that is acceptable. A random change is introduced into the model. This may be by change of the value in one or more dimensions. The energy of the new model is calculated. If the energy of the new model is lower (the model is better), the change is retained. If the energy of the new model is higher, the model may be retained. If the energy is higher, the new model is retained with probability:

$$P = e^{\frac{-\Delta E}{kT}}$$

Where $\Delta E$ is the change in energy (negative being the new model is lower energy than the previous model), K is the Boltzman constant and T is the temperature.

Note that if $\Delta E$ is negative, the value of this expression is greater than one, and the change will always be retained. If $\Delta E$ is positive (the new model is not as good as the former model), the change may still be retained, depending on the value of $\Delta E$ and T. As T decreases, the probability of retaining a change that results in a worse model decreases, the model becomes "frozen".

After the change is accepted or rejected, the value of T is decreased (typically by 1 to 5%). This cycle of introduction of a random change, evaluation of ΔE, rejecting or retaining the change and lowering of T is repeated until no further improvement is seen.

Application of Scatter Search/Path Relinking and Tabu Search to Searching the Candidate Model Search Space A library that implements tabu search and scatter search/path relinking is commercially available (OptQuest callable library from OptTek Systems Inc, Boulder, Colo.). The implementation of this would be very similar to the implementation of genetic algorithm, except that a call to the function OCLGetSolution would be made to generate the next individual and the resulting fitness would be added to the data set using the function OCLPutSolution.

What is claimed is:

1. A computer implemented method for selecting a near optimal or optimal mathematical model from a set of candidate models, comprising:
   a) defining a candidate model search space having n dimensions, wherein n is a positive integer and each dimension represents a set of mutually exclusive features from which exactly one of said mutually exclusive features is chosen from each set of mutually exclusive features for each candidate model;
   b) selecting an initial set of candidate models by selecting one feature from each set of mutually excusive features by a uniform random process for each candidate model;
   c) computing a goodness of fit (fitness) of each model in terms of the log likelihood using a pharmacokinetic and/or pharmacodynamic model;
   d) calculating for each model an overall objective function given by the expression:

fitness+theta penalty·ntheta+random effect penalty·nrand+success·success penalty+covariance·covariance penalty+correlation·correlation penalty, wherein fitness is −2*log likelihood of the observed data given a pharmacokinetic and/or pharmacodynamic model, theta penalty is the penalty for each fitted parameter, ntheta is the number of parameters, random effect penalty is the penalty for each random effect, nrand is the number of random effects, success is 0 if the minimization was successful and 1 if not, success penalty is the penalty if the minimization is not successful, covariance is 0 if the covariance step was successful and 1 if not, covariance penalty is the penalty if the covariance step is not successful, correlation is 0 if no estimation correlations are >0.95 and 1 if at least one is >0.95 and correlation penalty is the penalty for a correlation >0.95;
   e) searching said models using the objective function and a method selected from the group consisting of full grid search, simulated annealing, integer programming, scatter search/path relinking, neural networks, tabu search and genetic algorithm to select the next set of models;
   f) repeating steps c) to e) with the selected method of searching and next set of models until no further improvement in the lowest value of overall objective functions of models is achieved;
   g) selecting the model with lowest value of the objective function as the optimal or near optimal model.

2. The method of claim 1, wherein NONMEM/NMTRAN control files are generated for each model selected in step b) or step e) by substituting text associated with each selected feature into a control file template;

NONMEM/NMTRAN is run using said control files, and the computed goodness of fit (fitness) is input to an overall objective function generator to compute the overall objective function in step d.

3. The method of claim 1, wherein the overall objective function is computed by combining −2*log likelihood value with a penalty for each parameter estimated, a penalty for each element of the interindividual variance matrix estimated, a penalty for each element of the intraindividual variance matrix estimated, a penalty imposed if the minimization does not conclude successfully, a penalty if the standard errors of the parameter estimates cannot be obtained, a penalty if the correlation matrix of the estimates has any element >0.95 and a "niche" penalty for being similar to other models in the population (within a "niche radius" of other models.

4. A computer implemented method for selecting a near optimal or optimal mathematical model from a set of candidate models, comprising:
   a) defining a candidate search space having n dimensions, wherein n is a positive integer and each dimension represents a set of mutually exclusive features from which exactly one of said mutually exclusive features is chosen from each set of mutually exclusive features for each candidate model;
   b) selecting an initial set of candidate models by selecting one feature from each set of mutually excusive features by a uniform random process for each candidate model and representing each model by a bit string;
   c) computing a goodness of fit (fitness) of each model in terms of the log likelihood using a pharmacokinetic and/or pharmacodynamic model;
   d) calculating for each model an overall objective function given by the expression:

fitness+theta penalty·ntheta+random effect penalty·nrand+success·success penalty+covariance·covariance penalty+correlation·correlation penalty, wherein fitness is −2*log likelihood of the observed data given a pharmacokinetic and/or pharmacodynamic model, theta penalty is the penalty for each fitted parameter, ntheta is the number of parameters, random effect penalty is the penalty for each random effect, nrand is the number of random effects, success is 0 if the minimization was successful and 1 if not, success penalty is the penalty if the minimization is not successful, covariance is 0 if the covariance step was successful and 1 if not, covariance penalty is the penalty if the covariance step is not successful, correlation is 0 if no estimation correlations are >0.95 and 1 if at least one is >0.95 and correlation penalty is the penalty for a correlation >0.95;
   e) optionally, scaling the overall objective function of each model to be between an upper limit R and a lower limit S wherein the ratio of R to S is between 2:1 and 100:1;
   f) providing a number y of models to be in a subsequent generation;
   g) selecting with replacement y number of parents of the said subsequent generation from the current generation, wherein the probability of selection of a model in the current generation is proportional to said fitness or optionally to said scaled fitness;
   h) associating said parents into m groups comprising p parents where p is an integer greater than 1;

i) optionally, selecting some fraction of the m groups of parents to undergo at least one cross over;

j) optionally, crossing over said selected fraction at a random location on said bit string to create two new individuals for said subsequent generation;

k) assigning bit strings in current generation that are not selected for cross over to said subsequent generation;

l) optionally, randomly mutating bits of said subsequent generation bit strings wherein said mutation comprises changing a bit value 0 to a bit value of 1 or changing a bit value of 1 to a bit value of 0; and m) repeating the steps of c through l until further decrease in the lowest value of the overall objective function (improvement in maximum fitness) no longer occurs.

5. The method of claim 4 wherein the ratio of R to S is between 10:1 and 50:1.

6. The method of claim 4, wherein the number of models in the subsequent generation is equal to the number of models in the current generation.

7. The method of claim 4 wherein p=2.

8. The method of claim 4 wherein said fraction to undergo at least one cross over is selected randomly.

9. The method of claim 4 wherein said fraction to undergo at least one cross over is between 0.4 to 1.0.

10. The method of claim 4 wherein said models represent pharmacokinetic models and/or pharmacodynamic models.

11. The method of claim 10 wherein said sets of mutually exclusive features comprise one or more members of the group consisting of: the number of pharmacokinetic compartments, the presence of non-linear elimination, the presence of non-linear absorption, the presence of interindividual variability on each parameter, the function describing the interindividual variability of each parameter, the function describing the residual variability, the structure of the interindividual covariance matrix, emax pharmacodynamic model, linear pharmacodynamic model, types 1 through 4 indirect response pharmacodynamic model, the presence of an effect compartment, the relationship between drug elimination and age, the relationship between drug elimination and renal function, the relationship between drug elimination and liver function, the relationship between drug elimination and gender, the relationship between drug elimination and weight, the relationship between drug volume of distribution and age, the relationship between drug volume of distribution and gender, the relationship between drug volume of distribution and weight, the relationship between drug volume of distribution and cardiac function, the relationship between drug volume of distribution and renal function, the relationship between drug volume of distribution and liver function, the relationship between drug bioavailability and age, the relationship between drug bioavailability and gender, the relationship between drug bioavailability and weight, the relationship between drug bioavailability and liver function, the relationship between drug bioavailability and renal function.

12. A computer implemented method for selecting a near optimal or optimal mathematical model from a set of candidate models, comprising:

a) defining a candidate search space having n dimensions, wherein n is a positive integer and each dimension represents a set of mutually exclusive features from which exactly one of said mutually exclusive features is chosen from each set of mutually exclusive features for each candidate model; and b) selecting an initial set of candidate models by selecting one feature from each set of mutually excusive features by a uniform random process for each candidate model and representing each model by a bit string;

c) computing a goodness of fit (fitness) of each model in terms of the log likelihood using a pharmacokinetic and/or pharmacodynamic model;

d) calculating for each model an overall objective function given by the expression:

fitness+theta penalty·ntheta+random effect penalty·nrand+ success·success penalty+covariance·covariance penalty+ correlation·correlation penalty, wherein fitness is −2*log likelihood of the observed data given a pharmacokinetic and/or pharmacodynamic model, theta penalty is the penalty for each fitted parameter, ntheta is the number of parameters, random effect penalty is the penalty for each random effect, nrand is the number of random effects, success is 0 if the minimization was successful and 1 if not, success penalty is the penalty if the minimization is not successful, covariance is 0 if the covariance step was successful and 1 if not, covariance penalty is the penalty if the covariance step is not successful, correlation is 0 if no estimation correlations are >0.95 and 1 if at least one is >0.95 and correlation penalty is the penalty for a correlation >0.95;

e) searching the candidate search space using simulated annealing, wherein simulated annealing comprises the steps of:

i) randomly selecting one model from the candidate set of models;

ii) selecting an initial value for temperature (T) wherein T represents the tolerance of a minimization process for retaining a model that results in a higher energy; and T is defined as a change in value of the overall objective function;

iii) assessing the energy of the initial model, wherein energy is defined as the value of the overall objective function;

iv) randomly changing the model to generate a subsequent model;

v) assessing the energy of the subsequent model using the methods of steps c) and d) above;

vi) retaining the subsequent model as the current model if the energy is lower than the current model;

vii) if the energy of the subsequent model is higher than the energy of the current model, computing the probability of retaining it as:

$$e^{\Delta E/KT}$$

where T is the temperature, $\Delta E$ is the change in energy (current model energy−subsequent model energy), and k is Boltzman's constant; or Otherwise, rejecting the subsequent model;

viii) reducing the value of T;

ix) randomly selecting one model from the candidate set of models; and x) repeating the steps of iv through ix until further reduction in energy (overall objective function) no longer occurs.

13. The method of claim 12 wherein said sets of mutually exclusive features comprise one or more members of the group consisting of: the number of pharmacokinetic compartments, the presence of non-linear elimination, the presence of non-linear absorption, the presence of interindividual variability on each parameter, the function describing the interindividual variability of each parameter, the function describing the residual variability, the structure of the interindividual covariance matrix, emax pharmacodynamic model, linear pharmacodynamic model, types 1 through 4 indirect response pharmacodynamic model, the presence of an effect compartment, the relationship between drug elimination and age, the relationship between drug elimination and renal function, the relationship between drug elimination and liver function, the relationship between drug elimination and gender, the relationship between drug elimination and weight, the relationship between drug volume of distribution and age, the relationship between drug volume of distribution and gender, the relationship between drug volume of distribution and weight, the relationship between drug volume of distribution and cardiac function, the relationship between drug volume of distribution and renal function, the relationship between drug volume of distribution and liver function, the relationship between drug bioavailability and age, the relationship between drug bioavailability and gender, the relationship between drug bioavailability and weight, the relationship between drug bioavailability and liver function, the relationship between drug bioavailability and renal function.

14. A computer implemented method for selecting a near optimal or optimal mathematical model from a set of candidate models, comprising:
  a) defining a candidate search space having n dimensions, wherein n is a positive integer and each dimension represents a set of mutually exclusive features from which exactly one of said mutually exclusive features is chosen from each set of mutually exclusive features for each candidate model; and
  b) selecting an initial set of candidate models by selecting one feature from each set of mutually excusive features by a uniform random process for each candidate model and representing each model by a bit string;
  c) computing a goodness of fit (fitness) of each model in terms of the log likelihood using a pharmacokinetic and/or pharmacodynamic model;
  d) calculating for each model an overall objective function given by the expression:

fitness+theta penalty·ntheta+random effect penalty·nrand+ success·success penalty+covariance·covariance penalty+ correlation·correlation penalty, wherein fitness is −2*log likelihood of the observed data given a pharmacokinetic and/or pharmacodynamic model, theta penalty is the penalty for each fitted parameter, ntheta is the number of parameters, random effect penalty is the penalty for each random effect, nrand is the number of random effects, success is 0 if the minimization was successful and 1 if not, success penalty is the penalty if the minimization is not successful, covariance is 0 if the covariance step was successful and 1 if not, covariance penalty is the penalty if the covariance step is not successful, correlation is 0 if no estimation correlations are >0.95 and 1 if at least one is >0.95 and correlation penalty is the penalty for a correlation >0.95;
  e) initializing the search with a call to OCL setup in the OptQuest callable library and initializing a population of models with a call to OCLInitpop;
  f) initializing each search dimension with a call to OCLDefineVar in the OptQuest callable library;
  g) selecting an initial model from the candidate search space using scatter search/path relinking and tabu search as implemented in the OptQuest Callable library from OptTek systems by calling the function OCLGetSolution;
  h) searching the candidate search space using Scatter search/path relinking/Tabu search using the OptQuest Callable library wherein Scatter search/path relinking/Tabu search comprises the steps of:
  i) evaluating the overall objective function of the current model; ii) adding the value of the overall objective function of the current model to the OptQuest Callable library database with a call to the function OCLPutSolution,
  iii) finding the overall objective function of the best model thus far evaluated with a call to the function OCLGetBest in the OptQuest Callable Library;
  iv) getting the subsequent model with a call to the function OCLGetSolution; and
  v) repeating steps i–iv until either the required number of evaluations or convergence is seen; and
  i) deleting current problem from memory with a call to OCLGoodBye.

15. The method of claim 14 wherein said sets of mutually exclusive features comprise one or more members of the group consisting of: the number of pharmacokinetic compartments, the presence of non-linear elimination, the presence of non-linear absorption, the presence of interindividual variability on each parameter, the function describing the interindividual variability of each parameter, the function describing the residual variability, the structure of the interindividual covariance matrix, emax pharmacodynamic model, linear pharmacodynamic model, types 1 through 4 indirect response pharmacodynamic model, the presence of an effect compartment, the relationship between drug elimination and age, the relationship between drug elimination and renal function, the relationship between drug elimination and liver function, the relationship between drug elimination and gender, the relationship between drug elimination and weight, the relationship between drug volume of distribution and age, the relationship between drug volume of distribution and gender, the relationship between drug volume of distribution and weight, the relationship between drug volume of distribution and cardiac function, the relationship between drug volume of distribution and renal function, the relationship between drug volume of distribution and liver function, the relationship between drug bioavailability and age, the relationship between drug bioavailability and gender, the relationship between drug bioavailability and weight, the relationship between drug bioavailability and liver function, the relationship between drug bioavailability and renal function.

16. A computer program product comprising computer usable storage medium having computer executable instructions which when executed on a computer perform a process for selecting a near optimal or optimal mathematical model from a set of candidate models, the process comprising:
  a) defining a candidate model search space having n dimensions, wherein n is a positive integer and each dimension represents a set of mutually exclusive features from which exactly one of said mutually exclusive features is chosen from each set of mutually exclusive features for each candidate model;
  b) selecting an initial set of candidate models by selecting one feature from each set of mutually excusive features by a uniform random process for each candidate model;

c) computing a goodness of fit (fitness) of each model in terms of the log likelihood using a pharmacokinetic and/or pharmacodynamic model;

d) calculating for each model an overall objective function given by the expression:

fitness+theta penalty·ntheta+random effect penalty·nrand+ success·success penalty+covariance·covariance penalty+ correlation·correlation penalty, wherein fitness is −2*log likelihood of the observed data given a pharmacokinetic and/or pharmacodynamic model, theta penalty is the penalty for each fitted parameter, ntheta is the number of parameters, random effect penalty is the penalty for each random effect, nrand is the number of random effects, success is 0 if the minimization was successful and 1 if not, success penalty is the penalty if the minimization is not successful, covariance is 0 if the covariance step was successful and 1 if not, covariance penalty is the penalty if the covariance step is not successful, correlation is 0 if no estimation correlations are >0.95 and 1 if at least one is >0.95 and correlation penalty is the penalty for a correlation >0.95;

e) searching said models using the objective function and a method selected from the group consisting of full grid search, simulated annealing, integer programming, scatter search/path relinking, neural networks, tabu search and genetic algorithm to select the next set of models;

f) repeating steps c) to e) with the selected method of searching and next set of models until no further improvement in the lowest value of overall objective functions of models is achieved;

g) selecting the model with lowest value of the objective function as the optimal or near optimal model.

17. A computer program product comprising computer usable storage medium having computer executable instructions which when executed on a computer perform a process for selecting a near optimal or optimal mathematical model from a set of candidate models, the process comprising:

a) defining a candidate model search space having n dimensions, wherein n is a positive integer and each dimension represents a set of mutually exclusive features from which exactly one of said mutually exclusive features is chosen from each set of mutually exclusive features for each candidate model;

b) selecting an initial set of candidate models by selecting one feature from each set of mutually excusive features by a uniform random process for each candidate model and representing each model by a bit string;

c) computing a goodness of fit (fitness) of each model in terms of the log likelihood using a pharmacokinetic and/or pharmacodynamic model;

d) calculating for each model an overall objective function given by the expression:

fitness+theta penalty·ntheta+random effect penalty·nrand+ success·success penalty+covariance·covariance penalty+ correlation·correlation penalty, wherein fitness is −2*log likelihood of the observed data given a pharmacokinetic and/or pharmacodynamic model, theta penalty is the penalty for each fitted parameter, ntheta is the number of parameters, random effect penalty is the penalty for each random effect, nrand is the number of random effects, success is 0 if the minimization was successful and 1 if not, success penalty is the penalty if the minimization is not successful, covariance is 0 if the covariance step was successful and 1 if not, covariance penalty is the penalty if the covariance step is not successful, correlation is 0 if no estimation correlations are >0.95 and 1 if at least one is >0.95 and correlation penalty is the penalty for a correlation >0.95;

e) optionally, scaling the overall objective function of each model to be between an upper limit R and a lower limit S wherein the ratio of R to S is between 2:1 and 100:1;

f) providing a number y of models to be in a subsequent generation;

g) selecting with replacement y number of parents of the said subsequent generation from the current generation, wherein the probability of selection of a model in the current generation is proportional to said fitness or optionally to said scaled fitness;

h) associating said parents into m groups comprising p parents where p is an integer greater than 1;

i) optionally, selecting some fraction of the m groups of parents to undergo at least one cross over;

j) optionally, crossing over said selected fraction at a random location on said bit string to create two new individuals for said subsequent generation;

k) assigning bit strings in current generation that are not selected for cross over to said subsequent generation;

l) optionally, randomly mutating bits of said subsequent generation bit strings wherein said mutation comprises changing a bit value 0 to a bit value of 1 or changing a bit value of 1 to a bit value of 0; and m) repeating the steps of c through l until further decrease in the lowest value of the overall objective function (improvement in maximum fitness) no longer occurs.

* * * * *